US012490651B2

(12) United States Patent
Kang et al.

(10) Patent No.: US 12,490,651 B2
(45) Date of Patent: Dec. 2, 2025

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Moon Sung Kang, Cheonan-si (KR); Jung Geun Lee, Cheonan-si (KR); Sang Yong Park, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 19/219,335

(22) Filed: May 27, 2025

(65) Prior Publication Data

US 2025/0287833 A1 Sep. 11, 2025

Related U.S. Application Data

(63) Continuation of application No. 19/057,277, filed on Feb. 19, 2025.

(30) Foreign Application Priority Data

Feb. 19, 2024 (KR) ........................ 10-2024-0023290
Apr. 11, 2024 (KR) ........................ 10-2024-0048775

(51) Int. Cl.

| | |
|---|---|
| ***H10K 85/60*** | (2023.01) |
| ***C07C 211/61*** | (2006.01) |
| ***C07D 209/88*** | (2006.01) |
| ***C07D 263/60*** | (2006.01) |
| ***C07D 307/91*** | (2006.01) |

(Continued)

(52) U.S. Cl.

CPC .......... *H10K 85/633* (2023.02); *C07C 211/61* (2013.01); *C07D 209/88* (2013.01); *C07D 263/60* (2013.01); *C07D 307/91* (2013.01); *C07D 319/24* (2013.01); *C07D 333/76* (2013.01); *C07D 409/04* (2013.01); *H10K 85/636* (2023.02); *C07B 2200/05* (2013.01); *C07C 2601/14* (2017.05); *C07C 2602/10* (2017.05); *C07C 2602/42* (2017.05);

(Continued)

(58) Field of Classification Search

CPC .. C07C 211/61; C07B 2200/05; H10K 85/633
See application file for complete search history.

(56) References Cited

U.S. PATENT DOCUMENTS

2024/0431199 A1* 12/2024 Parham ................ H10K 85/633

FOREIGN PATENT DOCUMENTS

CN 115850093 A * 3/2023
KR 10-2021-0015615 A 2/2021

(Continued)

OTHER PUBLICATIONS

Machine-generated English-language translation of KR 10-2611998-B1.*

(Continued)

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound of Formula 1 that can improve the luminous efficiency, stability, and lifespan of an organic electronic element using the same, the organic electronic element and an electronic device thereof.

11 Claims, 2 Drawing Sheets

(51) Int. Cl.

| | |
|---|---|
| ***C07D 319/24*** | (2006.01) |
| ***C07D 333/76*** | (2006.01) |
| ***C07D 409/04*** | (2006.01) |
| ***H10K 50/11*** | (2023.01) |
| ***H10K 50/19*** | (2023.01) |

(52) U.S. Cl.

CPC ...... *C07C 2603/18* (2017.05); *C07C 2603/40* (2017.05); *C07C 2603/48* (2017.05); *C07C 2603/74* (2017.05); *C07C 2603/97* (2017.05); *H10K 50/11* (2023.02); *H10K 50/19* (2023.02); *H10K 85/615* (2023.02); *H10K 85/622* (2023.02); *H10K 85/626* (2023.02); *H10K 85/6574* (2023.02); *H10K 85/6576* (2023.02)

(56) References Cited

FOREIGN PATENT DOCUMENTS

| | | | | | |
|---|---|---|---|---|---|
| KR | 10-2023-0061616 | A | | 5/2023 | |
| KR | 10-2611998 | B1 | | 12/2023 | |
| KR | 2611998 | B1 | * | 12/2023 | |
| WO | WO-2023072976 | A1 | * | 5/2023 | ............ H10K 50/15 |

OTHER PUBLICATIONS

Machine-generated English-language translation of CN 115850093-A.*

* cited by examiner

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to compounds for organic electronic elements, organic electronic elements using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer etc.

A material used as an organic material layer in an organic electronic element may be classified into a light emitting material and a charge transport material, such as a hole injection material, a hole transport material, an electron transport material, an electron injection material etc. depending on its function.

The most problematic issues with organic electroluminescent devices are lifespan and efficiency, and as displays become larger in size, these efficiency and lifespan issues must be resolved.

Efficiency, lifespan and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase.

However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Further, recently, in organic electroluminescent devices, in order to solve the emission problem in the hole transport layer, an emitting-auxiliary layer must be present between the hole transport layer and an emitting layer, and it is necessary to develop different emitting-auxiliary layers according to each of the emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value, therefore the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic element are lowered and the life span is shortened. Therefore, it is urgently required to develop an emitting-auxiliary layer having a high T1 value and a HOMO level between the HOMO energy level of the hole transport layer and the HOMO energy level of the emitting layer.

Meanwhile, it is necessary to develop a hole injection layer material having stable characteristics, that is, a high glass transition temperature, against Joule heating generated when the device is driven, while delaying penetration of the metal oxide from the anode electrode (ITO), which is one of the causes of shortening the lifespan of the organic electronic element, into the organic layer. The low glass transition temperature of the hole transport layer material has a characteristic that when the device is driven, the uniformity of the surface of the thin film is lowered, which has been reported to have a great influence on the lifespan of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electronic element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electronic element has not been sufficiently developed yet. Therefore, the development of new materials continues to be required, and in particular, the development of materials for the emitting-auxiliary layer is urgently required.

DETAILED DESCRIPTION OF THE INVENTION

Summary

In order to solve the problems of the background art described above, the present invention has revealed a compound having a novel structure, and that when the compound is applied to an organic electronic element, the luminous efficiency, stability and lifespan of the element are greatly improved.

Accordingly, it is an object of the present invention to provide a novel compound, an organic electronic element using the same, and an electronic device thereof.

Technical Solution

The present invention provides a compound represented by Formula 1.

Formula 1

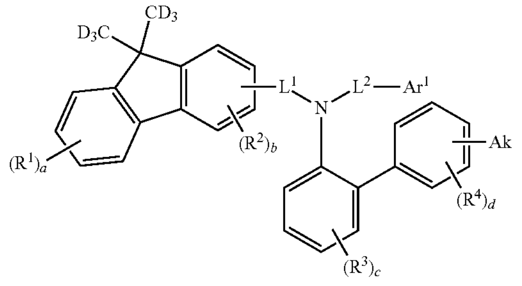

In another aspect, the present invention provides an organic electronic element comprising a compound represented by Formula 1 and an electronic device thereof.

Effects of the Invention

By using the compound according to the present invention, it is possible to achieve a high luminous efficiency, a low driving voltage, and a high heat resistance of the element, and can greatly improve the color purity and lifespan of the element.

DESCRIPTION OF THE NUMERALS IN THE DRAWINGS

Figure 1:
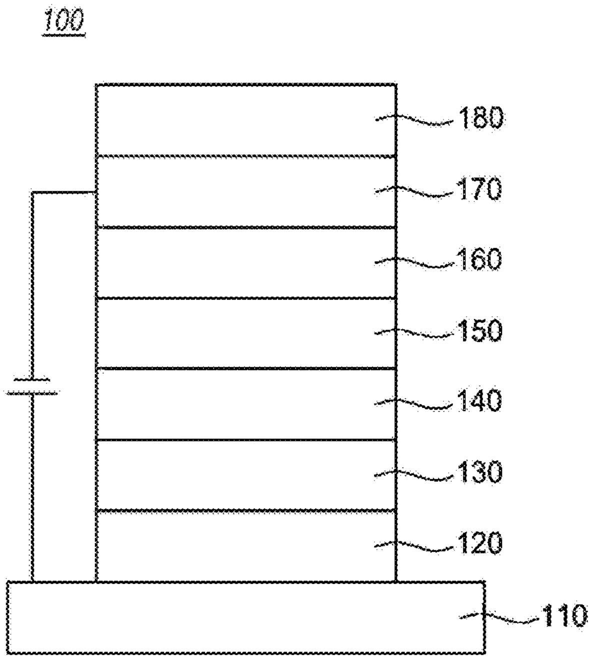
FIG. 1 to FIG. 3 illustrate an example of an organic electronic element according to the present invention.

| | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine (F), bromine (Br), chlorine (Cl), or iodine (I).

Unless otherwise stated, the term "alkyl" or "alkyl group", as used herein, has a single bond of 1 to 60 carbon atoms, 1 to 30 carbon atoms, 1 to 25 carbon atoms, 1 to 18 carbon atoms, or 1 to 12 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, 2 to 30 carbon atoms, 2 to 25 carbon atoms, 2 to 18 carbon atoms, 2 to 12 carbon atoms, but is not limited thereto, and includes a linear or a branched chain group.

Unless otherwise stated, the term "cycloalkyl", as used herein, means alkyl forming a ring having 3 to 60 carbon atoms, 3 to 30 carbon atoms, 3 to 25 carbon atoms, 3 to 18 carbon atoms, 3 to 12 carbon atoms, but is not limited thereto.

Unless otherwise stated, the term "alkoxyl group", "alkoxy group" or "alkyloxy group", as used herein, means an alkyl group bonded to oxygen radical, but is not limited thereto, and has 1 to 60 carbon atoms, 1 to 30 carbon atoms, 1 to 25 carbon atoms, 1 to 18 carbon atoms, or 1 to 12 carbon atoms.

Unless otherwise stated, the term "aryloxyl group" or "aryloxy group", as used herein, means an aryl group bonded to oxygen radical, but is not limited thereto, and has 6 to 60 carbon atoms, 6 to 30 carbon atoms, 6 to 25 carbon atoms, 6 to 18 carbon atoms, or 6 to 12 carbon atoms.

Unless otherwise specified, the terms "aryl group" and "arylene group" used in the present invention have 6 to 60 carbon atoms, 6 to 30 carbon atoms, 6 to 25 carbon atoms, 6 to 18 carbon atoms, or 6 to 12 carbon atoms, respectively, but are not limited thereto. In the present invention, an aryl group or arylene group refers to an aromatic group of a single ring or multiple rings, and comprises an aromatic ring formed by combining adjacent substituents or participating in a reaction. For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, and has 2 to 60 carbon atoms, 2 to 30 carbon atoms, 2 to 25 carbon atoms, 2 to 18 carbon atoms, 2 to 12 carbon atoms, and comprises any one of a single ring or multiple ring, and may include heteroaliphatic ring and heteroaromatic ring. Also, the heterocyclic group may also be formed in conjunction with an adjacent group.

Unless otherwise stated, the term "heteroatom", as used herein, represents at least one of N, O, S, P, or Si.

Additionally, a "heterocyclic group" may also comprise a ring including $SO_2$ instead of ring-forming carbon. For example, a "heterocyclic group" includes the following compound.

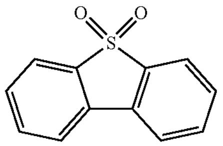 [SMILES: O=S1(=O)c2ccccc2-c2ccccc21]

Unless otherwise stated, the term "fluorenyl group", "fluorenylene group" or "fluorentriyl group" as used herein, means a monovalent or divalent functional group, in which R, R' and R" are all hydrogen in the following structures, and the term "substituted fluorenyl group" or "substituted fluorenylene group" means that at least one of the substituents R, R' and R" is a substituent other than hydrogen, and comprise those in which R and R' are bonded to each other to form a spiro compound together with the carbon to which they are bonded.

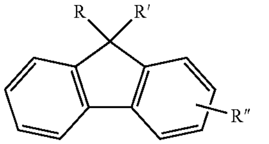

The term "spiro compound", as used herein, has a 'spiro union', and a spiro union means a connection formed by 2 rings sharing only one atom. Wherein, the atoms shared between the 2 rings are called 'spiro atoms', and depending on the number of spiro atoms contained in a compound, they are called 'monospiro-', 'dispiro-', and 'trispiro-' compounds, respectively.

Unless otherwise stated, the term "aliphatic" as used herein means an aliphatic hydrocarbon having 1 to 60 carbon atoms, 1 to 30 carbon atoms, 1 to 25 carbon atoms, 1 to 18 carbon atoms or 1 to 12 carbon atoms, and "aliphatic ring" means an aliphatic hydrocarbon ring having 3 to 60 carbon atoms, 3 to 30 carbon atoms, 3 to 25 carbon atoms, 3 to 18 carbon atoms or 3 to 12 carbon atoms.

Unless otherwise stated, the term "ring", as used herein, means an aliphatic ring having 3 to 60 carbon atoms, 3 to 30 carbon atoms, 3 to 25 carbon atoms, 3 to 18 carbon atoms or 3 to 12 carbon atoms; or an aromatic ring having 6 to 60 carbon atoms, 6 to 30 carbon atoms, 6 to 25 carbon atoms, 6 to 18 carbon atoms, or 6 to 12 carbon atoms; or a heterocyclic having 2 to 60 carbon atoms, 2 to 30 carbon atoms, 2 to 25 carbon atoms, 2 to 18 carbon atoms, 2 to 12 carbon atoms, or a fused ring formed by the combination thereof, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

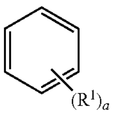

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

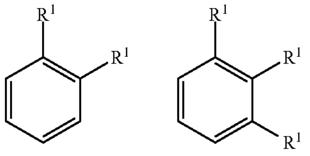

(a = 2) (a = 3)

Hereinafter, a compound according to one aspect of the present invention and an organic electronic element comprising the same will be described.

The present invention provides a compound represented by Formula 1.

Formula 1

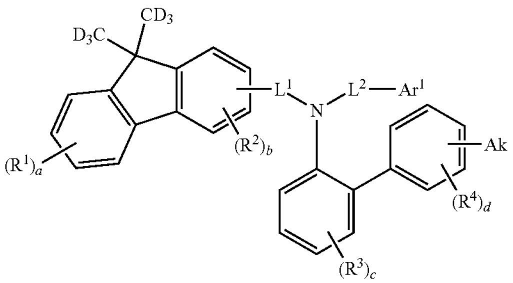

Wherein:

$R^1$, $R^2$, $R^3$ and $R^4$ are independently the same or different from each other and are independently selected from the group consisting of a hydrogen; deuterium; an $C_6$-$C_{60}$ aryl group; fluorenyl group; a $C_2$-$C_{60}$ heterocyclic group including at least one heteroatom of O, N, S, Si or P; a fused ring group of a $C_3$-Coo aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and a $C_3$-$C_{30}$ aliphatic ring; or a plurality of adjacent groups may be bonded to each other to form a ring, Wherein when $R^1$, $R^2$, $R^3$ and $R^4$ are an aryl group, preferably an $C_6$-$C_{30}$ aryl group, more preferably an $C_6$-$C_{25}$ aryl group, an $C_6$-$C_{18}$ aryl group or an $C_6$-$C_{12}$ aryl group, such as phenyl, biphenyl, terphenyl, naphthalene, phenanthrene, etc.

Wherein when $R^1$, $R^2$, $R^3$ and $R^4$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc.

Wherein when $R^1$, $R^2$, $R^3$ and $R^4$ are a fused ring group, preferably a fused ring group of an $C_5$-$C_{30}$ aliphatic ring and an $C_6$-$C_{30}$ aromatic ring, more preferably a fused ring group of an $C_5$-$C_{25}$ aliphatic ring and an $C_6$-$C_{25}$ aromatic ring.

Wherein when $R^1$, $R^2$, $R^3$ and $R^4$ are an aliphatic ring group, preferably a $C_3$-$C_{30}$ aliphatic ring group, more preferably a $C_3$-$C_{25}$ aliphatic ring group, a $C_3$-$C_{18}$ aliphatic ring group, and a $C_3$-$C_{12}$ aliphatic ring group, and specifically, cyclobutane, cyclopentane, cyclohexane, cyclohexacene, bicycloheptane, adamantyl, etc.

Wherein when $R^1$, $R^2$, $R^3$ and $R^4$ are an alkyl group, preferably a $C_1$-$C_{30}$ alkyl group, more preferably a $C_1$-$C_{25}$ alkyl group, a $C_1$-$C_{18}$ alkyl group or a $C_1$-$C_{12}$ alkyl group, such as a methyl group, ethyl group, propyl group, isopropyl group, butyl group, t-butyl group, pentyl group, etc.

Wherein when $R^1$, $R^2$, $R^3$ and $R^4$ are an alkoxyl group, preferably a $C_1$-$C_{25}$ alkoxyl group.

Wherein when $R^1$, $R^2$, $R^3$ and $R^4$ are an aryloxy group, preferably a $C_6$-$C_{25}$ aryloxy group.

$L^1$ and $L^2$ are each independently selected from the group consisting of a single bond; a $C_6$-$C_{60}$ arylene group; a fluorenylene group; a $C_2$-$C_{60}$ heterocyclic group including at least one heteroatom of O, N, S, Si or P;

Wherein when $L^1$ and $L^2$ are an arylene group, preferably an $C_6$-$C_{30}$ arylene group, more preferably an $C_6$-$C_{25}$ arylene group, an $C_6$-$C_{18}$ arylene group or an $C_6$-$C_{12}$ arylene group, such as phenylene, biphenylene, naphthylene, terphenylene, anthracenylene, etc.

Wherein when $L^1$ and $L^2$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, benzocarbazole, naphthobenzofuran, naphthobenzothiophene, etc.

$Ar^1$ is an $C_6$-$C_{60}$ aryl group; a fluorenyl group; a $C_2$-$C_{60}$ heterocyclic group including at least one heteroatom of O, N, S, Si or P;

Wherein when $Ar^1$ is an aryl group, preferably an $C_6$-$C_{30}$ aryl group, more preferably an $C_6$-$C_{25}$ aryl group, an $C_6$-$C_{18}$ aryl group or an $C_6$-$C_{12}$ aryl group, such as phenyl, biphenyl, terphenyl, naphthalene, phenanthrene, triphenylene, etc.

Wherein when $Ar^1$ is a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, benzocarbazole, naphthobenzofuran, naphthobenzothiophene, etc.

Ak is a $C_1$~$C_{50}$ alkyl group; or a $C_3$~$C_{30}$ aliphatic ring group;

Wherein when Ak is an alkyl group, preferably a $C_1$-$C_{30}$ alkyl group, more preferably a $C_1$-$C_{25}$ alkyl group, a $C_1$-$C_{18}$ alkyl group or a $C_1$-$C_{12}$ alkyl group, such as a methyl group, ethyl group, propyl group, isopropyl group, butyl group, t-butyl group, pentyl group, etc.

Wherein when Ak is an aliphatic ring group, preferably a $C_3$-$C_{30}$ aliphatic ring group, more preferably a $C_3$-$C_{25}$ aliphatic ring group, a $C_3$-$C_{18}$ aliphatic ring group, and a $C_3$-$C_{12}$ aliphatic ring group, and specifically, cyclobutane, cyclopentane, cyclohexane, cyclohexacene, bicycloheptane, adamantyl, etc.

a, c and d are independently integers from 0 to 4, b is an integer from 0 to 3, wherein the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; a $C_3$-$C_{20}$ aliphatic ring; a $C_7$-$C_{20}$ arylalkyl group; a $C_8$-$C_{20}$ arylalkenyl group; and a $C_7$-$C_{20}$ alkylaryl group; also the hydrogen of these substituents may be further substituted with one or more deuterium, and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Additionally, Formula 1 is represented by any one of the following Formulas 1-1 to 1-4.

Formula 1-1

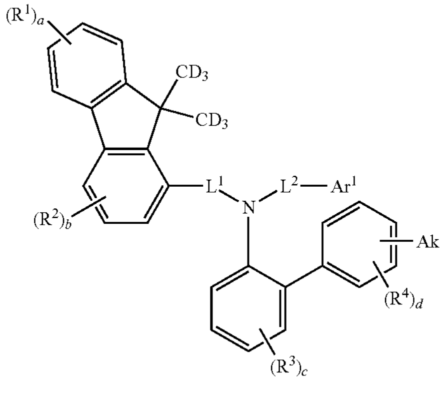

Formula 1-2

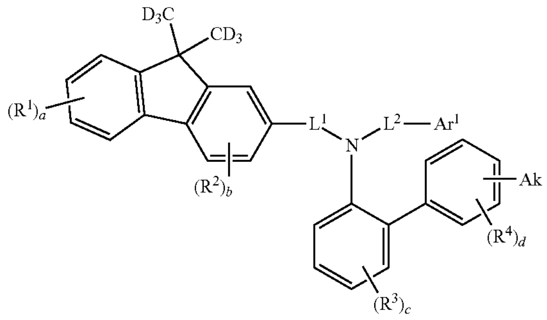

-continued

Formula 1-3

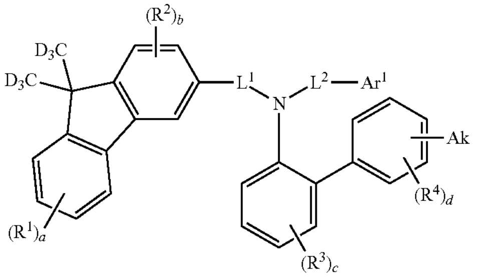

Formula 1-4

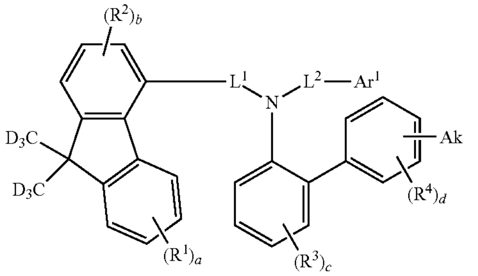

Wherein $R^1$, $R^2$, $R^3$, $R^4$, a, b, c, d, $L^1$, $L^2$, $Ar^1$ and Ak are the same as defined in Formula 1.

Additionally, Ak is represented by any one of the following Formulas Ak-1 to Ak-8.

Formula Ak-1

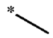

Formula Ak-2

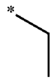

Formula Ak-3

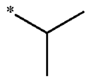

Formula Ak-4

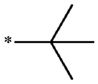

Formula Ak-5

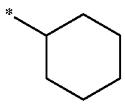

Formula Ak-6

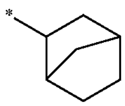

Formula Ak-7

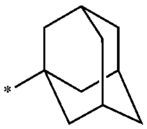

-continued

Formula Ak-8

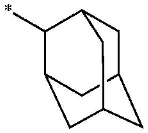

Wherein,

*indicates a position to be bonded,

Formulas Ak-1 to Ak-8 may be further substituted with one or more deuterium.

Additionally, $Ar^1$ is represented by any one of the following Formulas Ar-1 to Ar-11.

Formula Ar-1

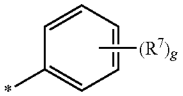

Formula Ar-2

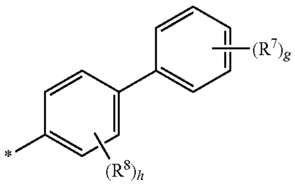

Formula Ar-3

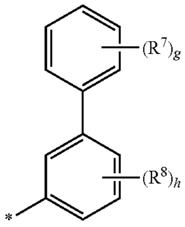

Formula Ar-4

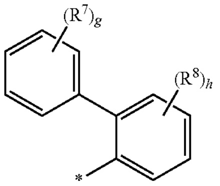

Formula Ar-5

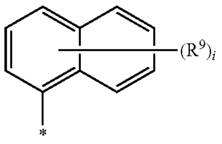

Formula Ar-6

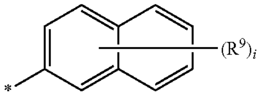

Formula Ar-7

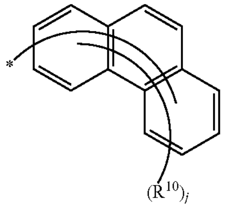

-continued

Formula Ar-8

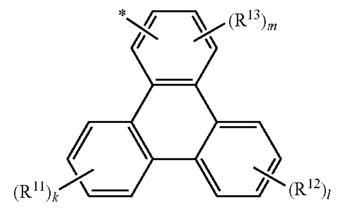

Formula Ar-9

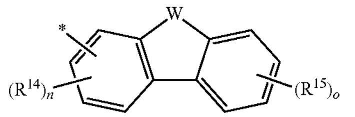

Formula Ar-10

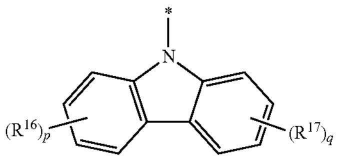

Formula Ar-11

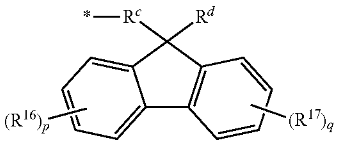

Wherein, $R^7$, $R^8$, $R^9$, $R^{10}$, $R^{11}$, $R^{12}$, $R^{13}$, $R^{14}$, $R^{15}$, $R^{16}$ and $R^{17}$ are independently the same or different from each other and are independently selected from the group consisting of a hydrogen; or deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ aliphatic group; $C_7$-$C_{20}$ arylalkyl group; $C_8$-$C_{20}$ arylalkenyl group; and a $C_7$-$C_{20}$ alkylaryl group; or a plurality of adjacent groups may be bonded to each other to form a ring, $R^c$ is selected from a group consisting of a $C_1$-$C_{50}$ alkyl group; an $C_6$-$C_{60}$ aryl group; and a $C_2$-$C_{60}$ heterocyclic group including at least one heteroatom of O, N, S, Si or P;

$R^d$ is selected from a group consisting of a hydrogen; or deuterium; a $C_1$-$C_{50}$ alkyl group; an $C_6$-$C_{60}$ aryl group; and a $C_2$-$C_{60}$ heterocyclic group including at least one heteroatom of O, N, S, Si or P;

Wherein $R^c$ and $R^d$ are an alkyl group, preferably a $C_1$-$C_{30}$ alkyl group, more preferably a $C_1$-$C_{25}$ alkyl group, a $C_1$-$C_{18}$ alkyl group or a $C_1$-$C_{12}$ alkyl group, such as a methyl group, ethyl group, propyl group, isopropyl group, butyl group, t-butyl group, pentyl group, etc.

Wherein $R^c$ and $R^d$ are an aryl group, preferably an $C_6$-$C_{30}$ aryl group, more preferably an $C_6$-$C_{25}$ aryl group, an $C_6$-$C_{18}$ aryl group or an $C_6$-$C_{12}$ aryl group, such as phenyl, biphenyl, terphenyl, naphthalene, phenanthrene, triphenylene, etc.

Wherein $R^c$ and $R^d$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, benzocarbazole, naphthobenzofuran, naphthobenzothiophene, etc.

$R^c$ and $R^d$ can be bonded to each other to form a spiro, g is an integer from 0 to 5, h, k, l, o, p and q are independently integers from 0 to 4, i is an integer from 0 to 7, j is an integer from 0 to 9, m and n are independently integers from 0 to 3, W is O, S, $C(R^{28})(R^{29})$ or $NR^{30}$, $R^{28}$, $R^{29}$ and $R^{30}$ are selected from a group consisting of a $C_1$-$C_{20}$ alkyl group; a $C_2$-$C_{20}$ alkenyl group; $C_6$-$C_{20}$ aryl group; $C_6$-$C_{20}$ aryl group substituted with deuterium; a fluorenyl group; a $C_2$-$C_{20}$ heterocyclic group including at least one heteroatom of O, N, S, Si or P; $C_3$-$C_{20}$ aliphatic group; $C_7$-$C_{20}$ arylalkyl group; $C_8$-$C_{20}$ arylalkenyl group; and a $C_7$-$C_{20}$ alkylaryl group; or, $R^{27}$ and $R^{28}$ may be bonded to each other to form a ring,

* indicates a position to be bonded, $L^1$ and $L^2$ are selected from a single bond or one of the following Formulae L-1 to L-27.

[Formula L-1]

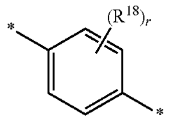

[Formula L-2]

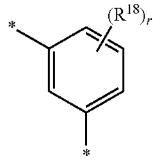

[Formula L-3]

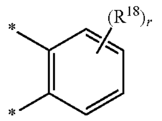

[Formula L-4]

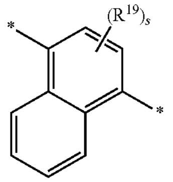

[Formula L-5]

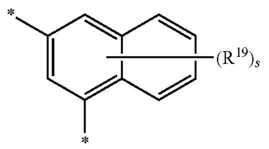

[Formula L-6]

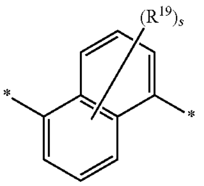

-continued
[Formula L-7]
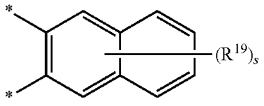
[Formula L-8]
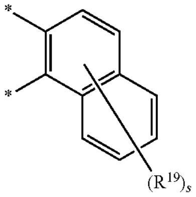
[Formula L-9]
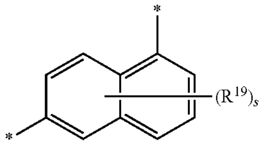
[Formula L-10]
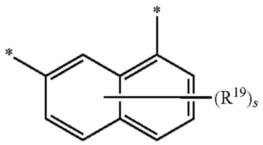
[Formula L-11]
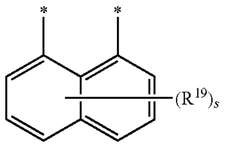
[Formula L-12]
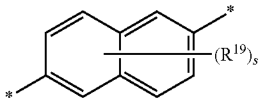
[Formula L-13]
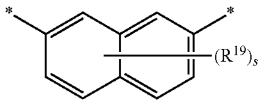
[Formula L-14]
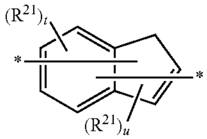
[Formula L-15]
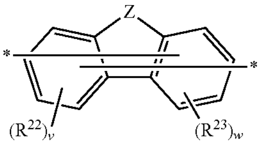
[Formula L-16]
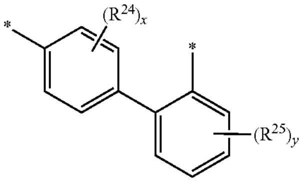
-continued
[Formula L-17]
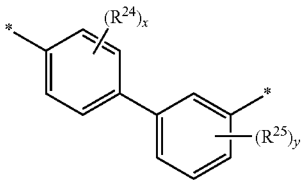
[Formula L-18]
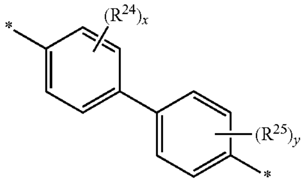
[Formula L-19]
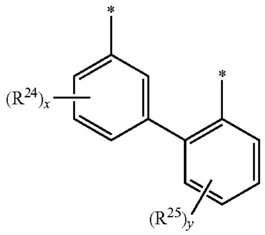
[Formula L-20]
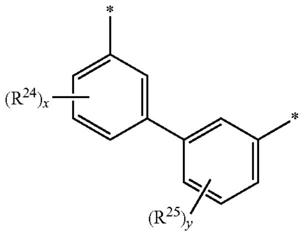
[Formula L-21]
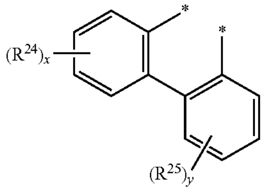
[Formula L-22]
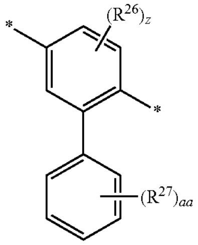
[Formula L-23]
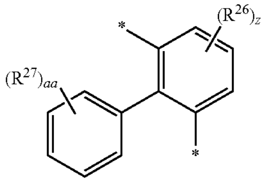

-continued

[Formula L-24]

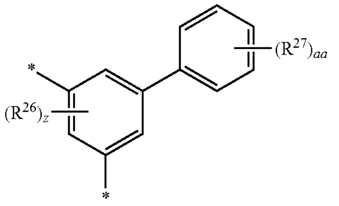

[Formula L-25]

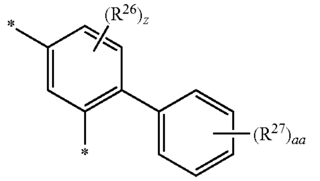

[Formula L-26]

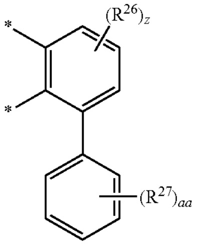

[Formula L-27]

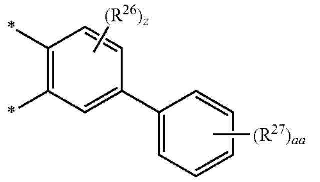

Wherein,

Z is O, S, $C(R^{31})(R^{32})$ or N—$Ar^5$, $R^{18}$, $R^{19}$, $R^{20}$, $R^{21}$, $R^{22}$, $R^{23}$, $R^{24}$, $R^{25}$, $R^{26}$ and $R^{27}$ are the same as definition of $R^7$, or a plurality of adjacent groups may be bonded to each other to form a ring, $R^{31}$ and $R^{32}$ are the same as the definition of $R^{28}$, $Ar^5$ is selected from a group consisting of a $C_1$-$C_{20}$ alkyl group; $C_6$-$C_{20}$ aryl group; $C_6$-$C_{20}$ aryl group substituted with deuterium; a fluorenyl group; a $C_2$-$C_{20}$ heterocyclic group including at least one heteroatom of O, N, S, Si or P;

r, t, v, w, x, y and z are independently integers from 0 to 4, s is an integer from 0 to 6, u is an integer from 0 to 2, aa is an integer from 0 to 5,

* indicates a position to be bonded.

$Ar^1$ is represented by the following Formula Ar-12 or Formula Ar-13.

Formula Ar-12

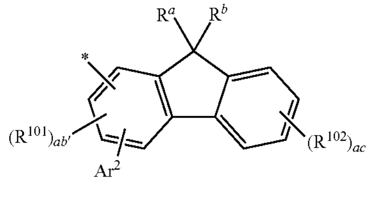

-continued

Formula Ar-13

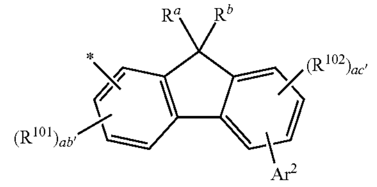

Wherein, $R^a$ and $R^b$ are independently selected from the group consisting of $C_1$-$C_{20}$ alkyl group; $C_1$-$C_{20}$ alkyl group substituted with deuterium; $C_2$-$C_{20}$ alkenyl group; $C_6$-$C_{20}$ aryl group; $C_6$-$C_{20}$ aryl group substituted with deuterium; a fluorenyl group; a $C_2$~$C_{20}$ heterocyclic group including at least one heteroatom of O, N, S, Si or P; $C_3$-$C_{20}$ aliphatic group; $C_7$-$C_{20}$ arylalkyl group; a $C_8$-$C_{20}$ arylalkenyl group; and a $C_7$-$C_{20}$ alkylaryl group; or $R^a$ and $R^b$ can be bonded to each other to form a spiro, $R^a$ and $R^b$ may preferably be methyl, deuterated methyl, phenyl or deuterated phenyl, more preferably $R^a$ and $R^b$ may be the same as each other, and more preferably $R^a$ and $R^b$ may be methyl or deuterated methyl at the same time.

$R^{101}$ and $R^{102}$ are the same as the definition of $R^7$, or adjacent groups may be bonded to each other to form a ring, $Ar^2$ is selected from the group consisting of a $C_1$~$C_{20}$ alkyl group substituted or unsubstituted with deuterium; a $C_6$~$C_{20}$ aryl group substituted or unsubstituted with deuterium; a $C_2$~$C_{20}$ heterocyclic group including at least one heteroatom of O, N, S, Si or P; and a $C_7$-$C_{20}$ alkylaryl group;

$Ar^2$ may preferably be methyl, deuterated methyl, phenyl, deuterated phenyl or phenyl substituted with an alkyl group, and more preferably may be phenyl, deuterated phenyl or phenyl substituted with an alkyl group.

ab' is an integer from 0 to 2, ac is an integer from 0 to 4, and ab and ac' are independently integers from 0 to 3,

* indicates a position to be bonded.

Formula Ar-12 may preferably be any one of the following Formulas Ar-12-1 to Ar-12-12.

Formula Ar-12-1

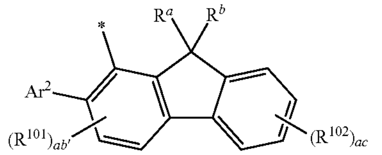

Formula Ar-12-2

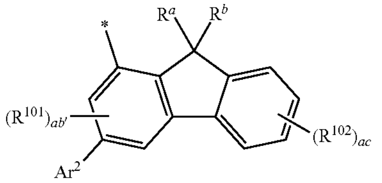

-continued
Formula Ar-12-3
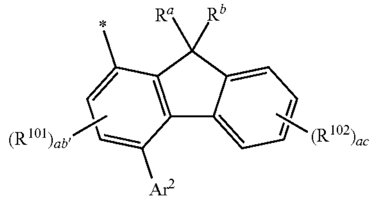
Formula Ar-12-4
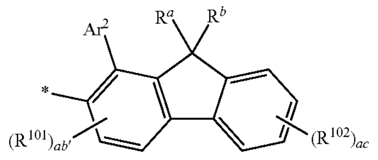
Formula Ar-12-5
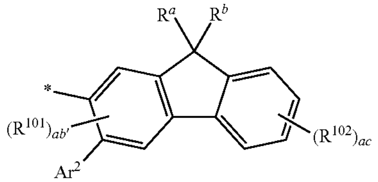
Formula Ar-12-6
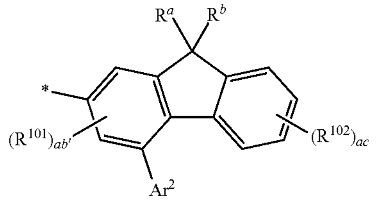
Formula Ar-12-7
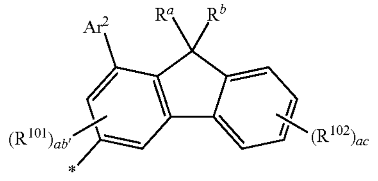
Formula Ar-12-8
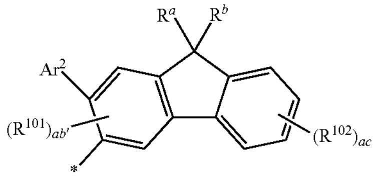
Formula Ar-12-9
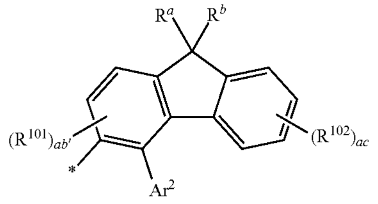
Formula Ar-12-10
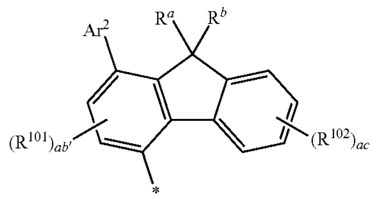
-continued
Formula Ar-12-11
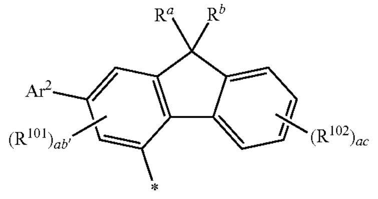
Formula Ar-12-12
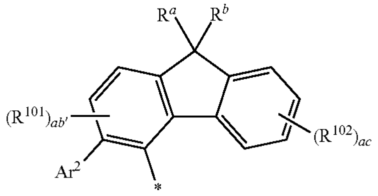
Wherein:
$Ar^2$, $R^a$, $R^b$, $R^{101}$, $R^{102}$, ab', ac and * are the same as defined in Formula Ar-12.
Formula Ar-13 may preferably be any one of the following Formulas Ar-13-1 to Ar-13-16.
Formula Ar-13-1
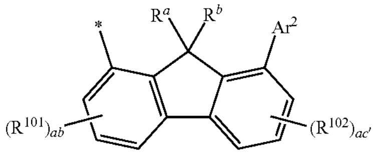
Formula Ar-13-2
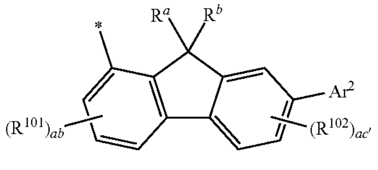
Formula Ar-13-3
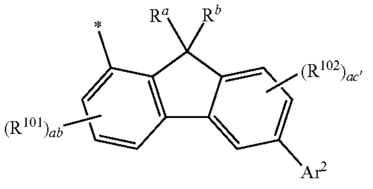
Formula Ar-13-4
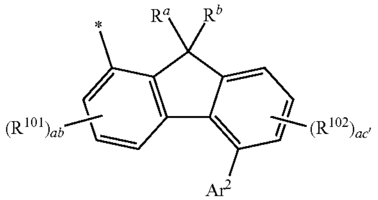
Formula Ar-13-5
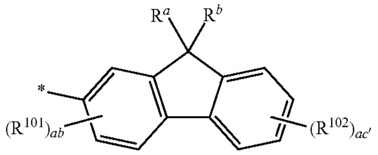

-continued
Formula Ar-13-6
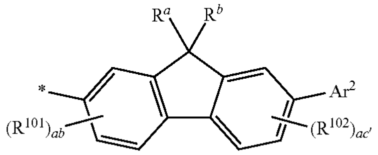
Formula Ar-13-7
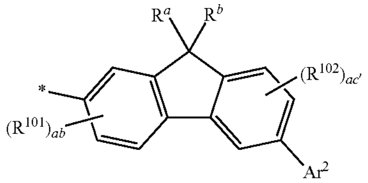
Formula Ar-13-8
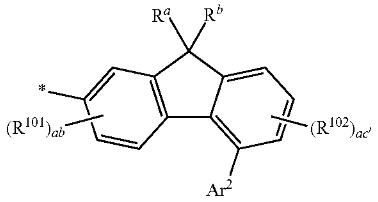
Formula Ar-13-9
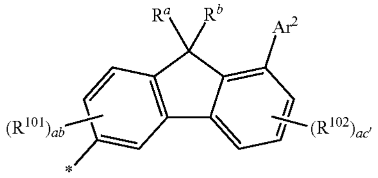
Formula Ar-13-10
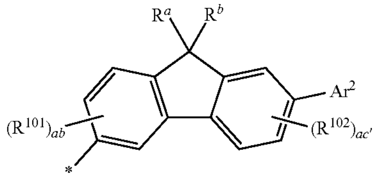
Formula Ar-13-11
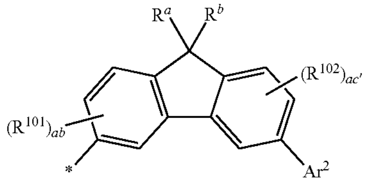
Formula Ar-13-12
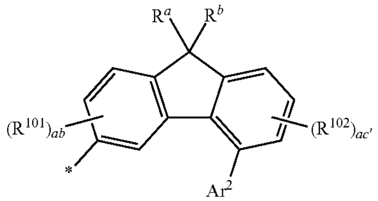
Formula Ar-13-13
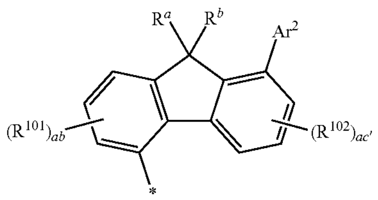
-continued
Formula Ar-13-14
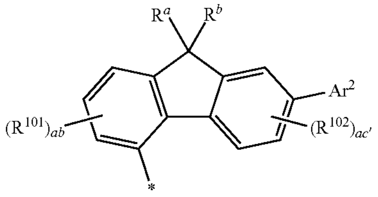
Formula Ar-13-15
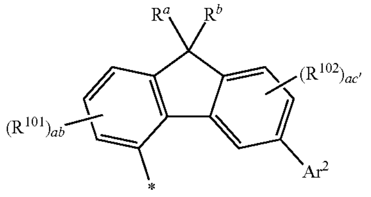
Formula Ar-13-16
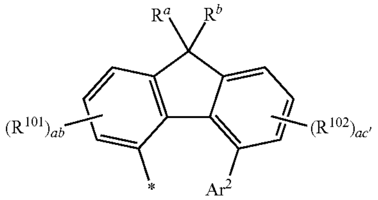
Wherein:
$Ar^2$, $R^a$, $R^b$, $R^{101}$, $R^{102}$, ab, ac' and * are the same as defined in Formula Ar-13.
Specifically, the compound represented by Formula 1 may be any one of the following compounds P-1 to P-160, but is not limited thereto.
P-1
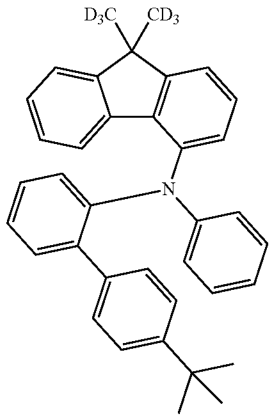

-continued
P-2
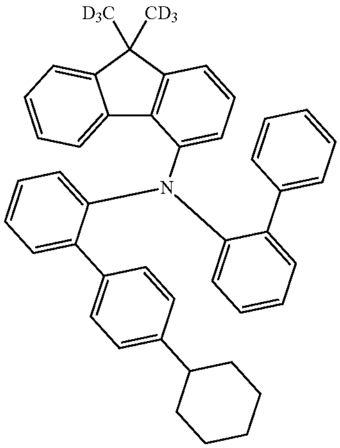
P-3
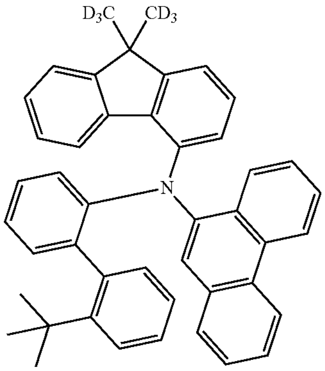
P-4
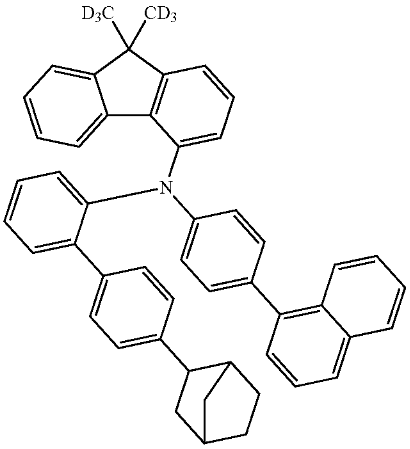
-continued
P-5
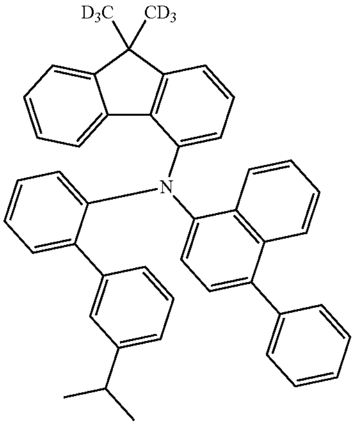
P-6
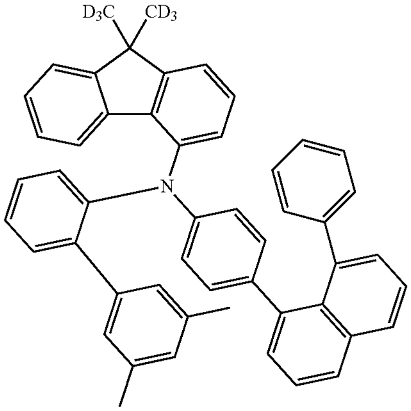
P-7
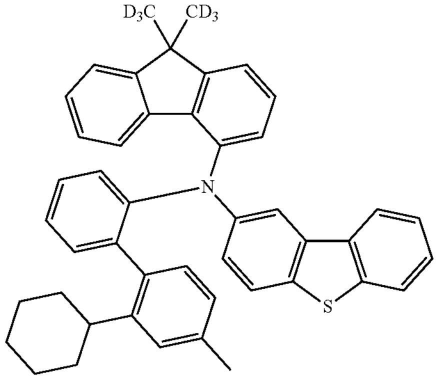

-continued
P-8
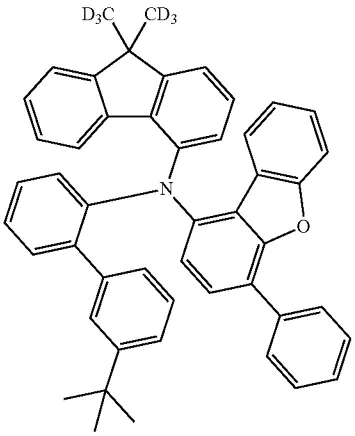
P-9
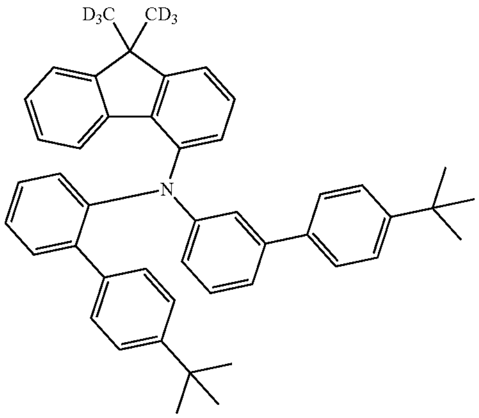
P-10
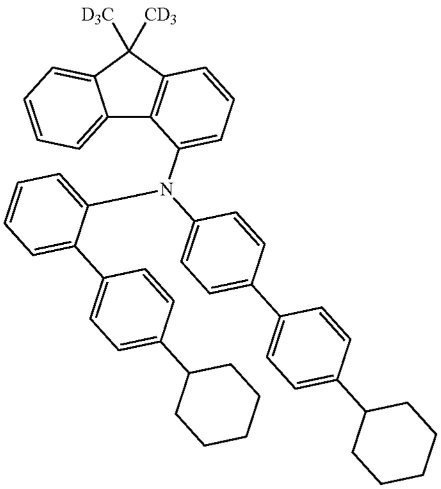
-continued
P-11
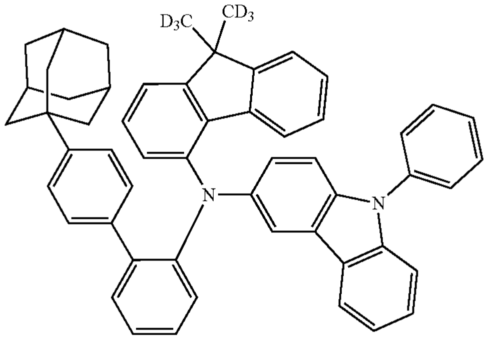
P-12
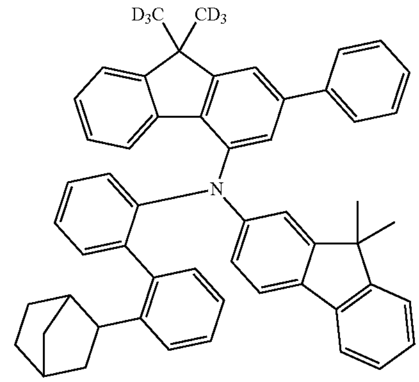
P-13
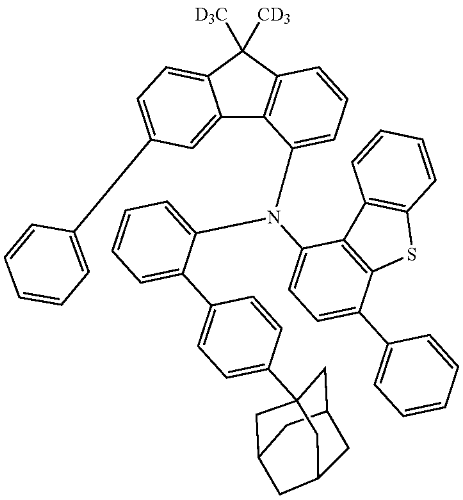
P-14
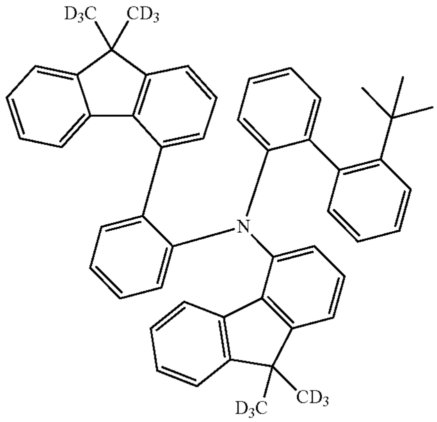

-continued
P-15
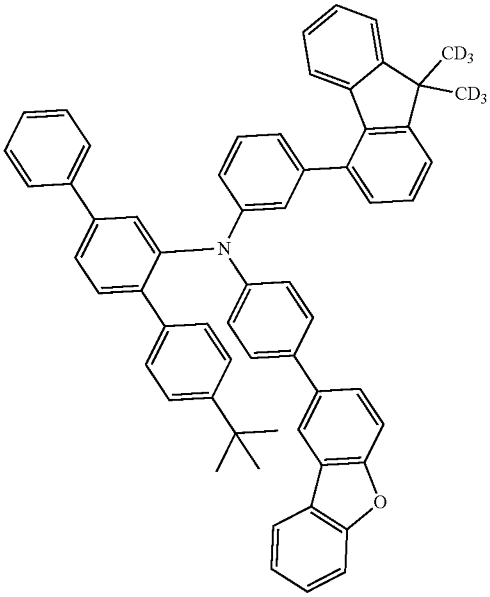
P-16
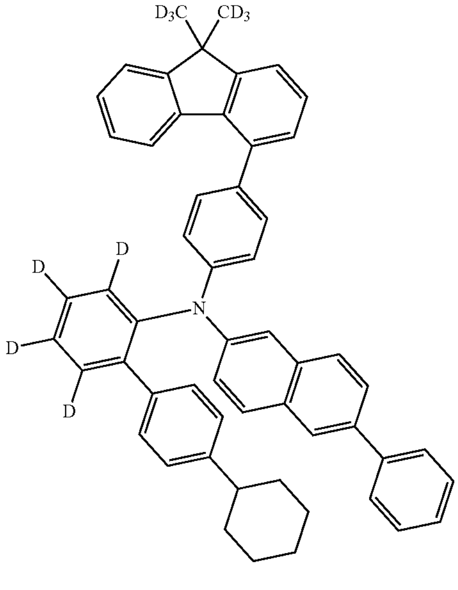
-continued
P-17
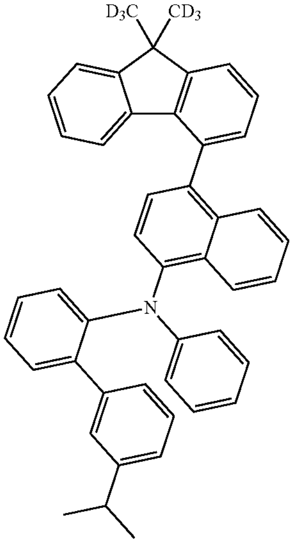
P-18
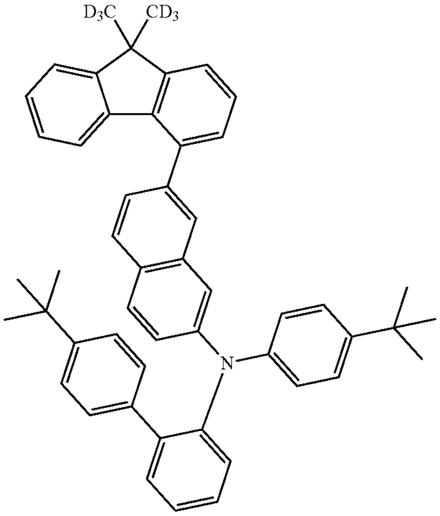
P-19
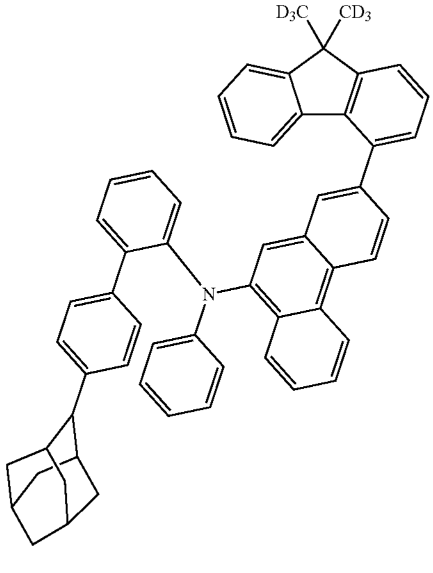

-continued
P-20
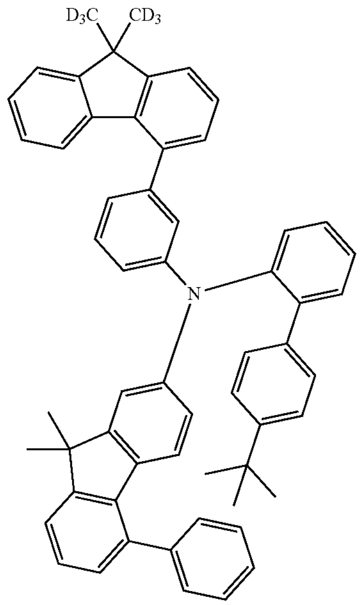
P-21
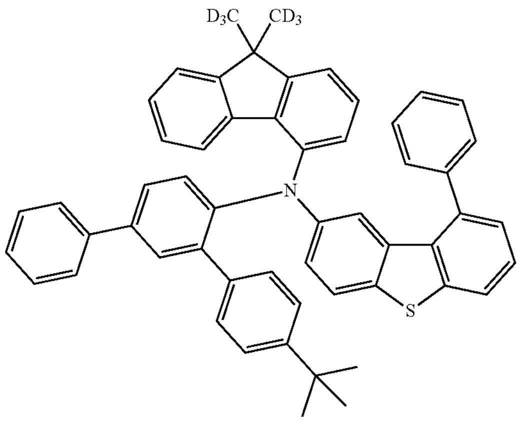
P-22
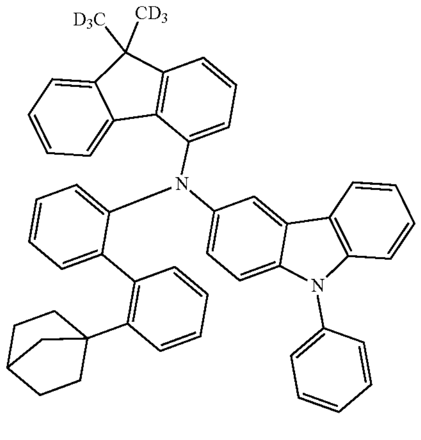
-continued
P-23
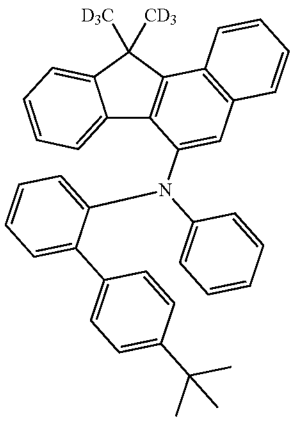
P-24
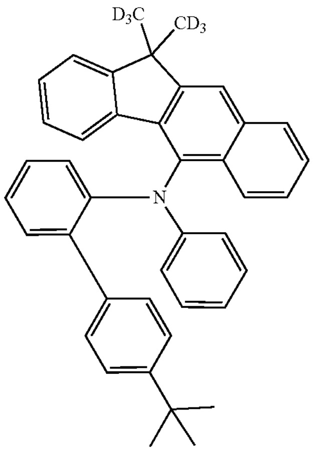
P-25
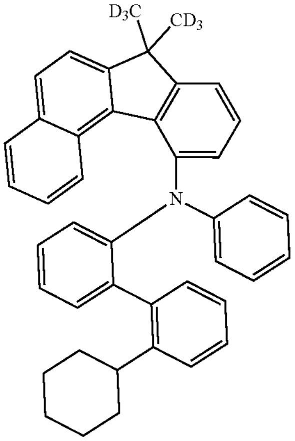

-continued
P-26
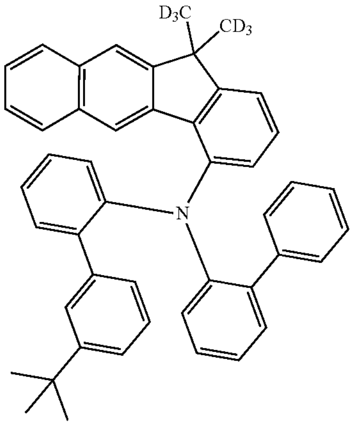
P-27
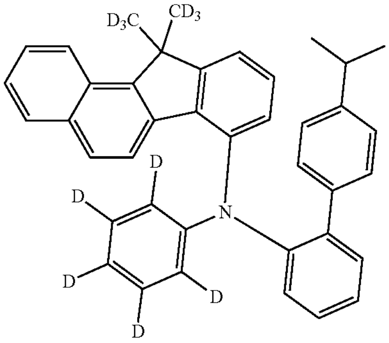
P-28
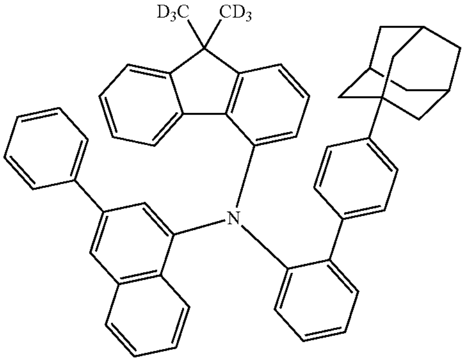
P-29
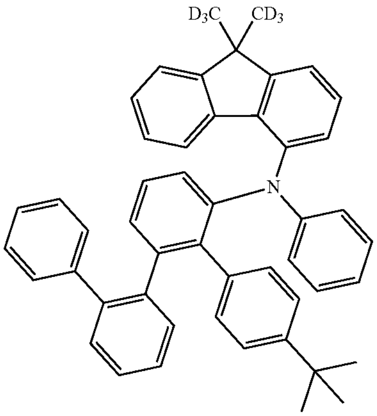
-continued
P-30
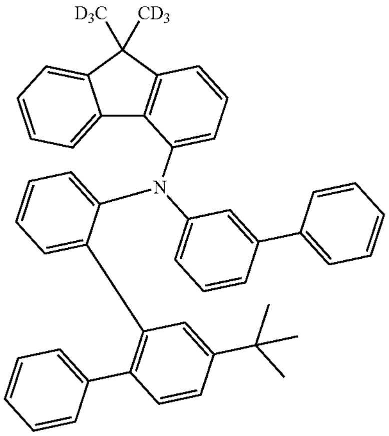
P-31
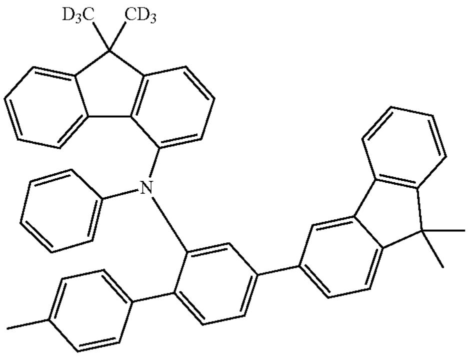
P-32
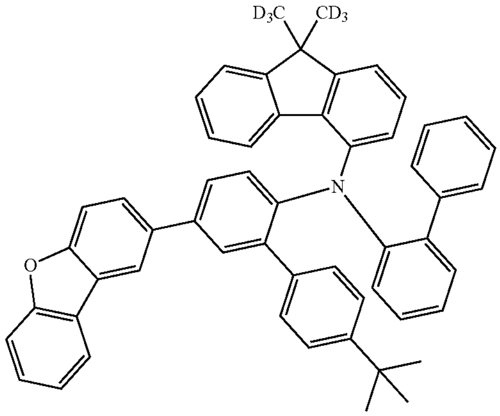

-continued
P-33
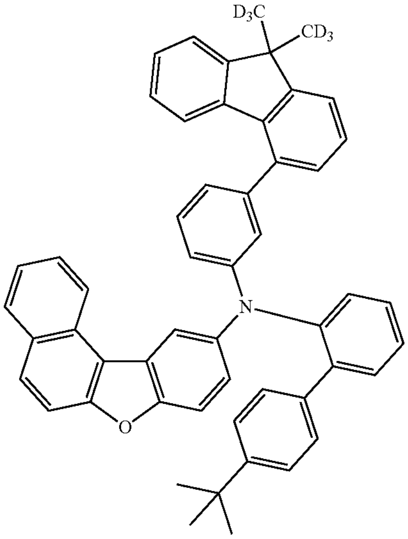
P-34
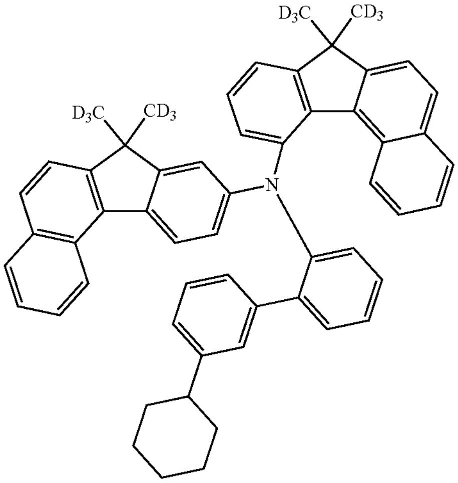
P-35
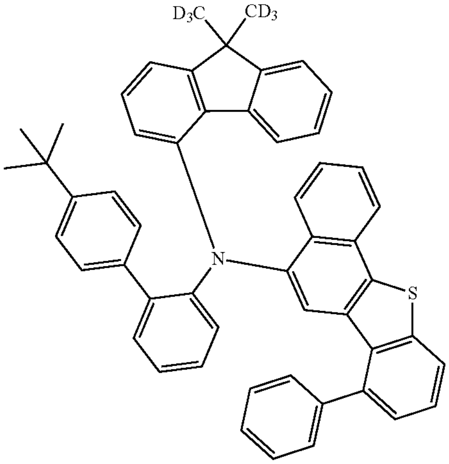
-continued
P-36
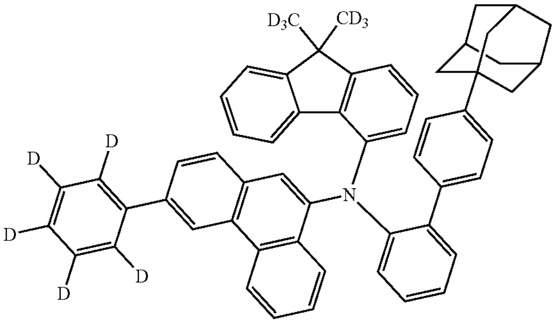
P-37
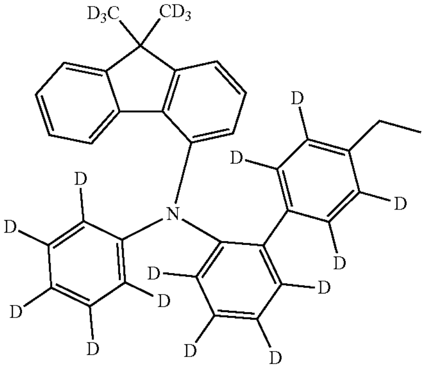
P-38
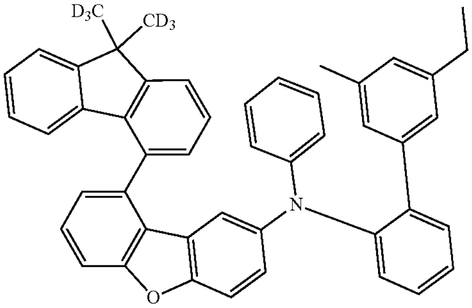
P-39
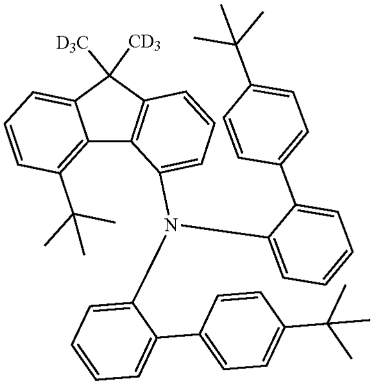

-continued
P-40
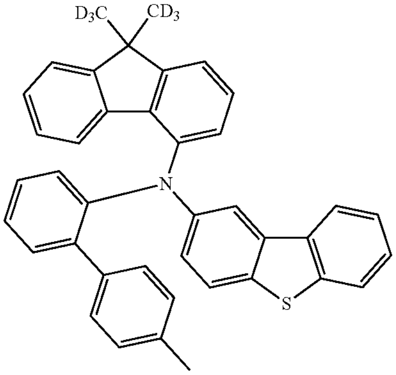
P-41
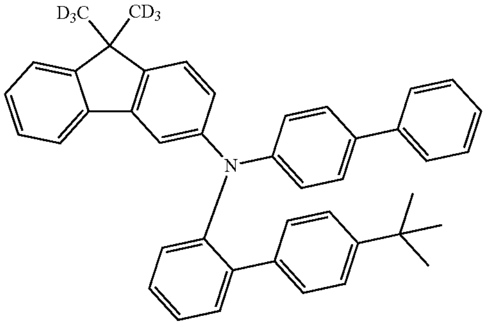
P-42
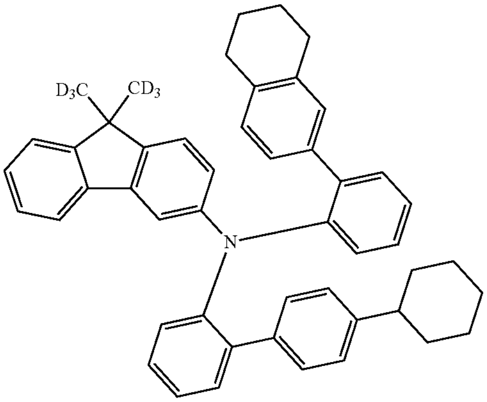
P-43
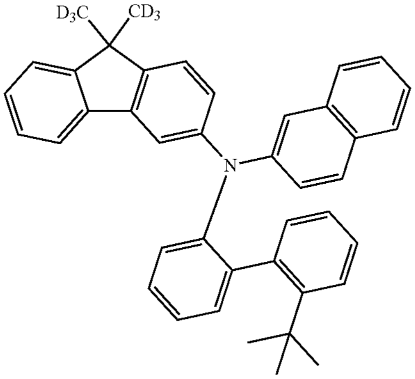
-continued
P-44
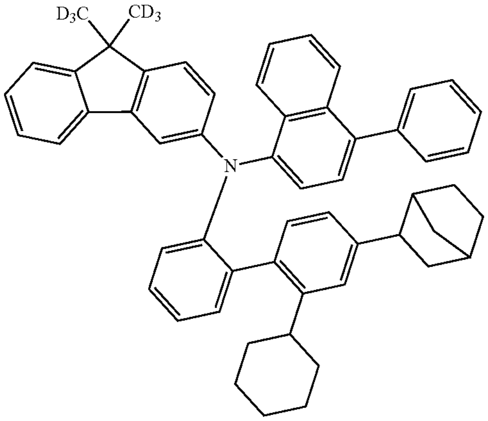
P-45
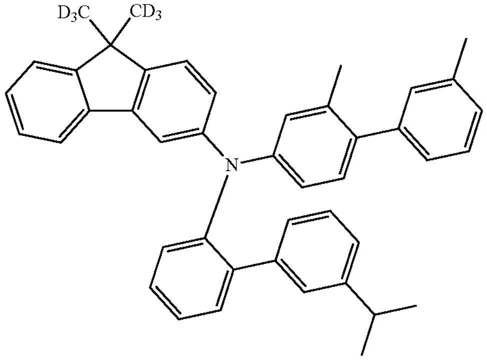
P-46
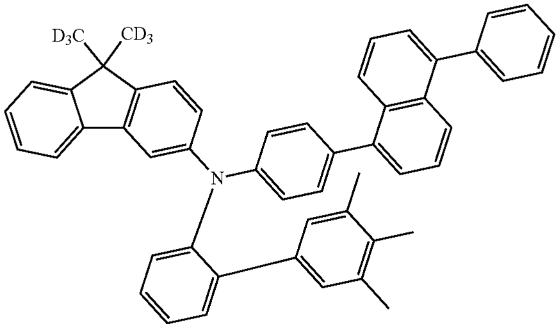
P-47
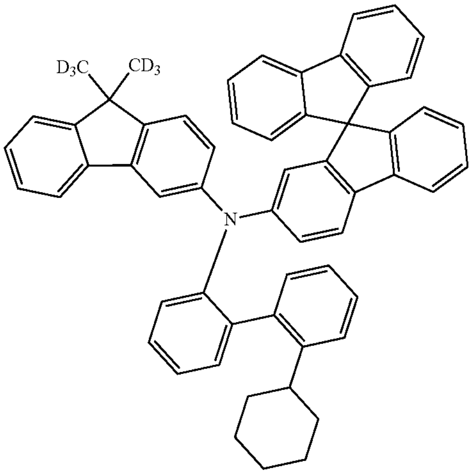

-continued
P-48
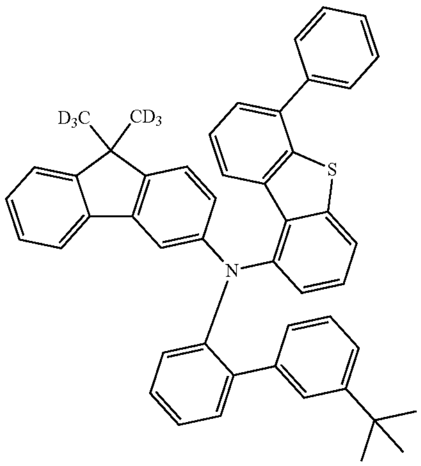
P-49
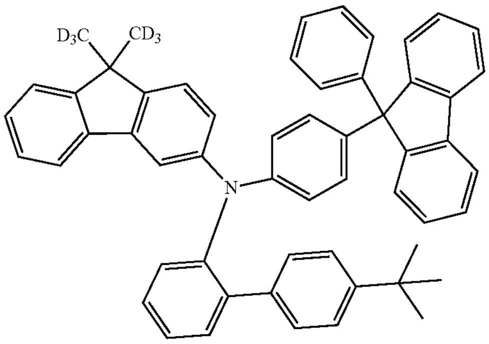
P-50
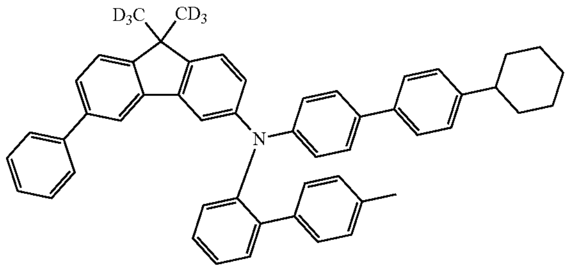
P-51
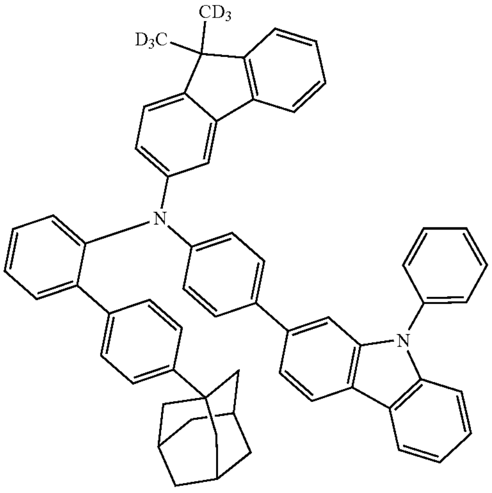
-continued
P-52
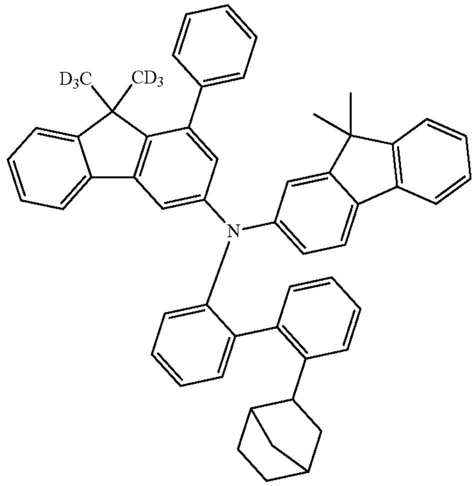
P-53
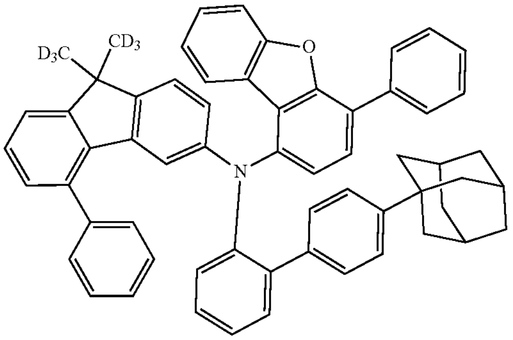
P-54
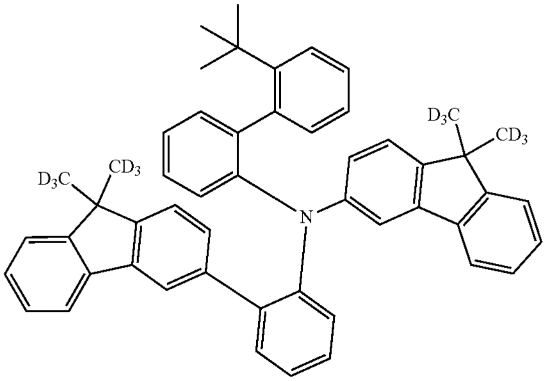

-continued
P-55
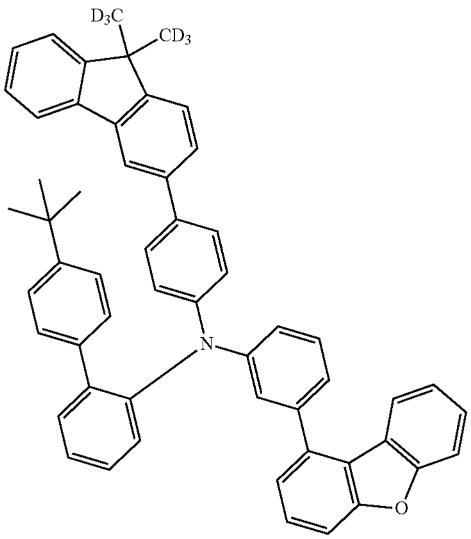
P-56
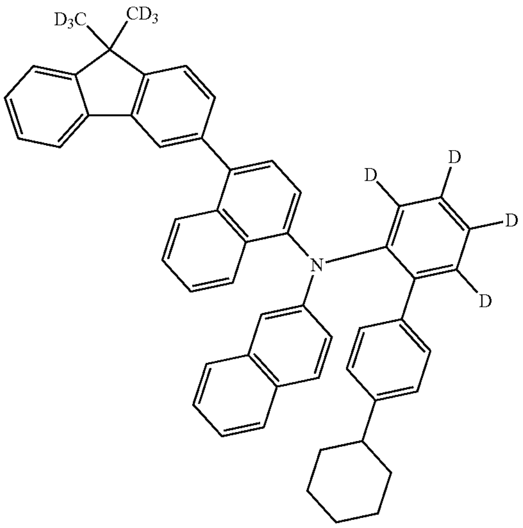
P-57
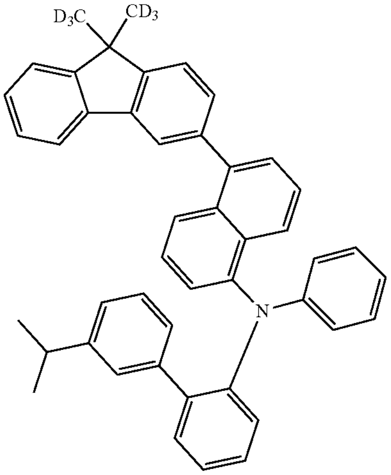
-continued
P-58
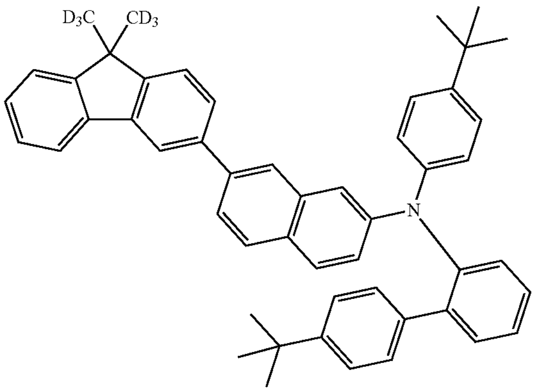
P-59
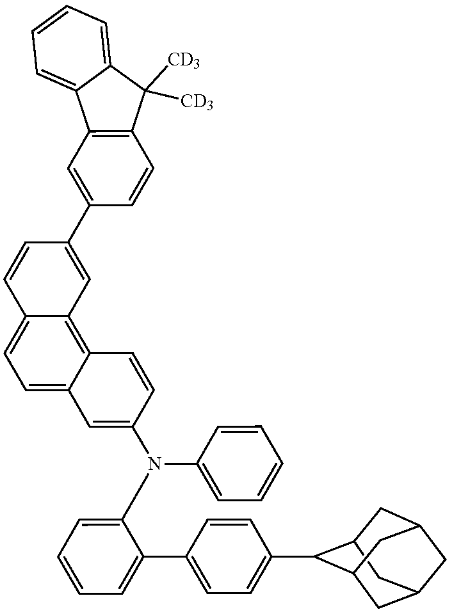
P-60
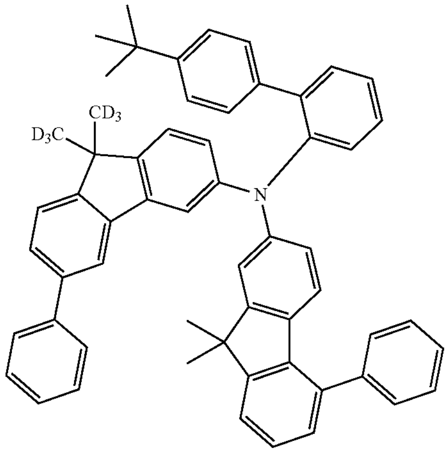

-continued
P-61
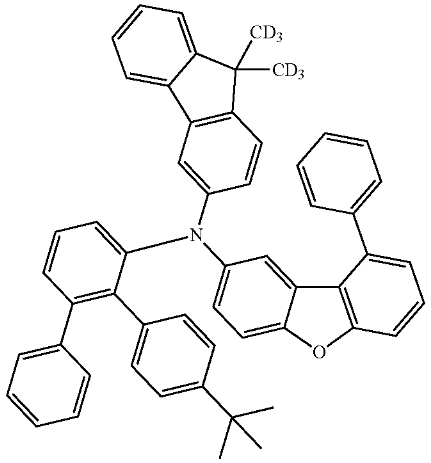
P-62
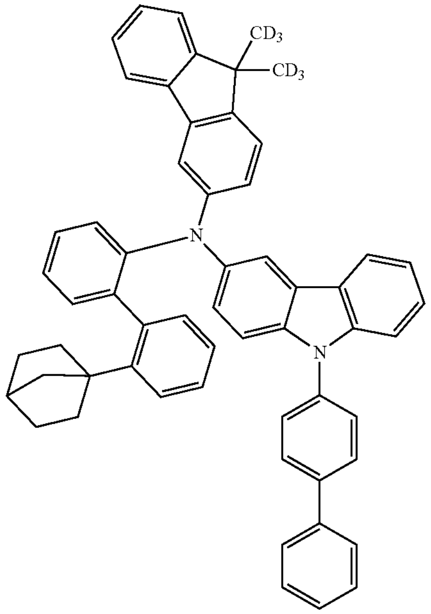
P-63
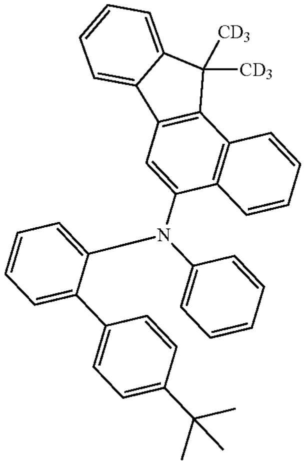
-continued
P-64
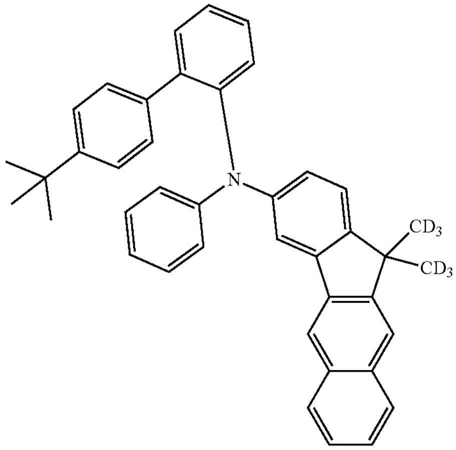
P-65
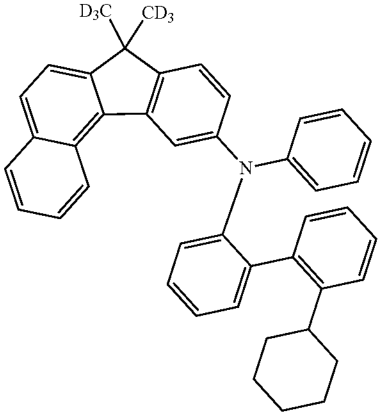
P-66
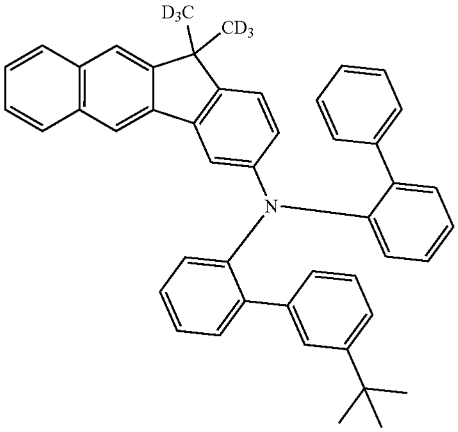

-continued
P-67
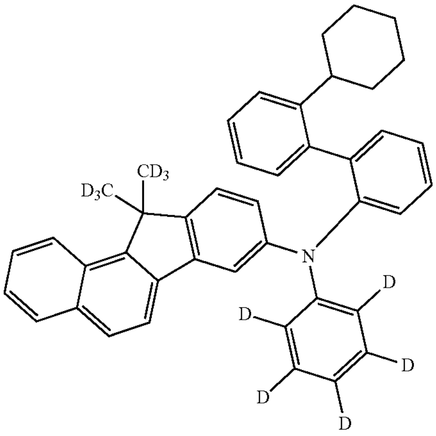
P-68
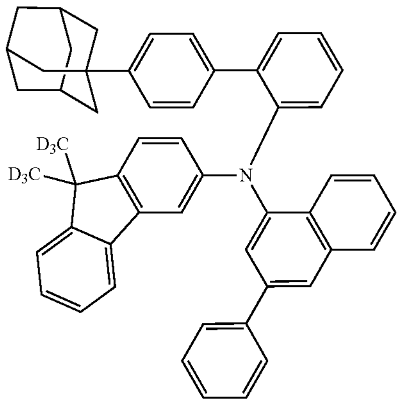
P-69
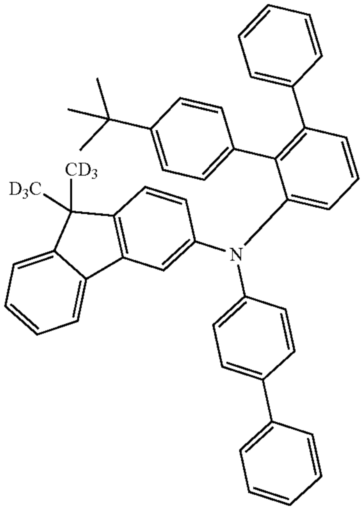
-continued
P-70
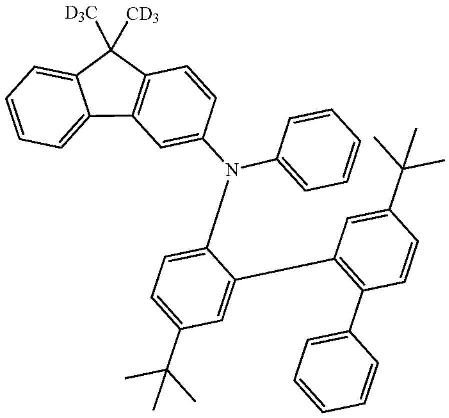
P-71
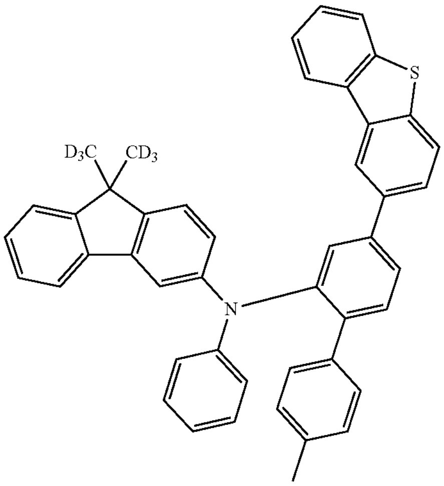
P-72
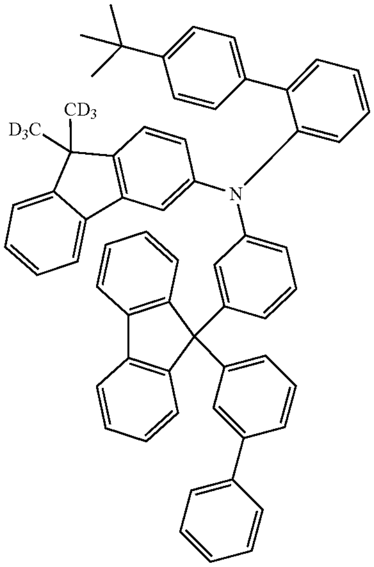

-continued
P-73
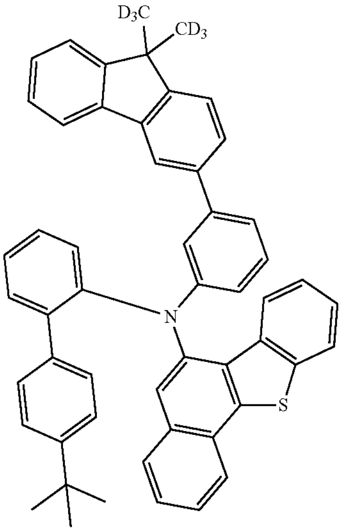
P-74
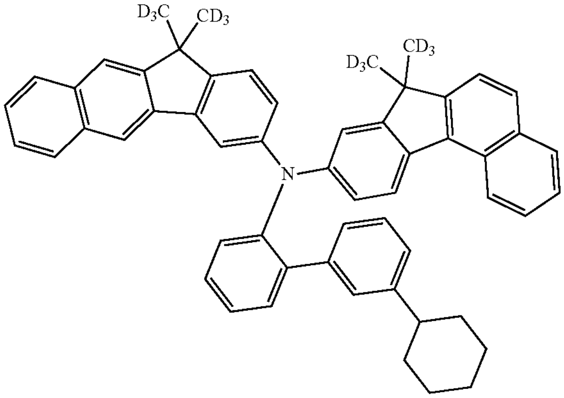
P-75
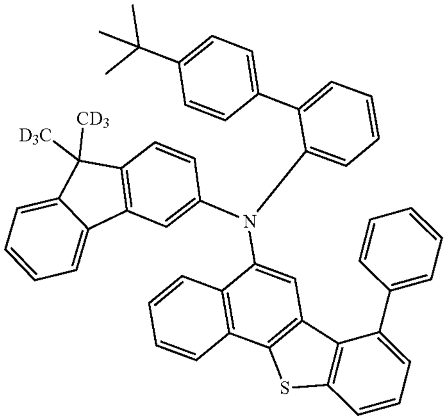
-continued
P-76
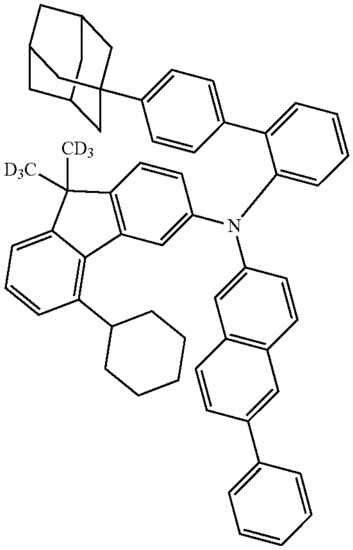
P-77
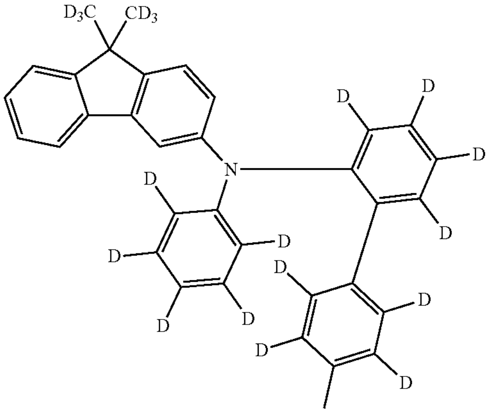
P-78
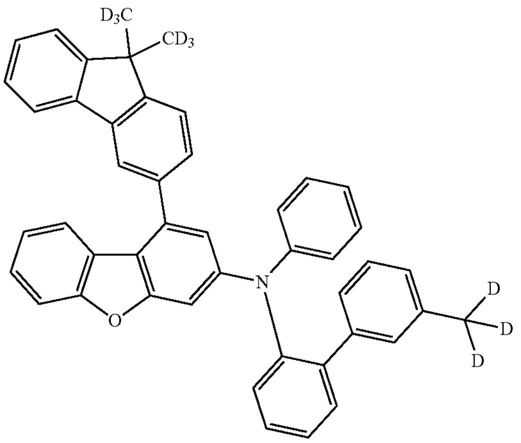

-continued
P-79
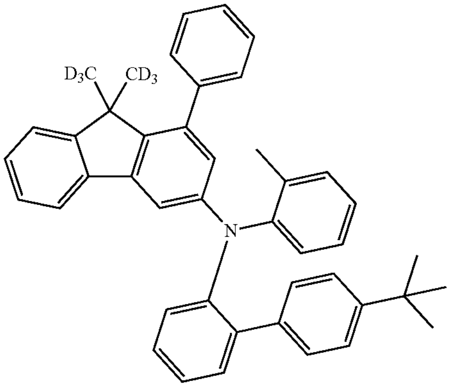
P-80
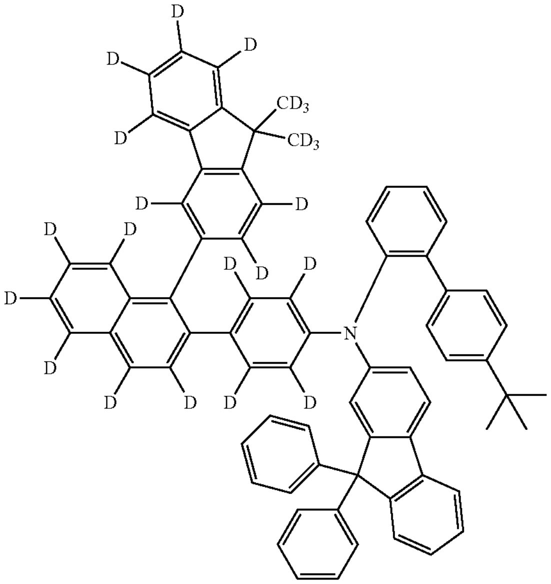
P-81
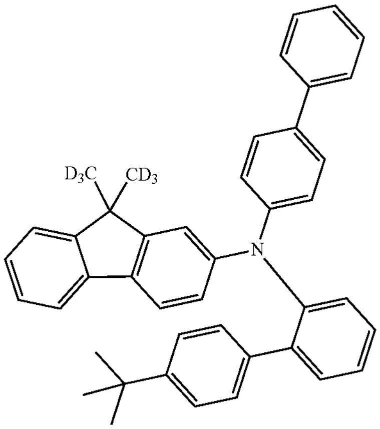
-continued
P-82
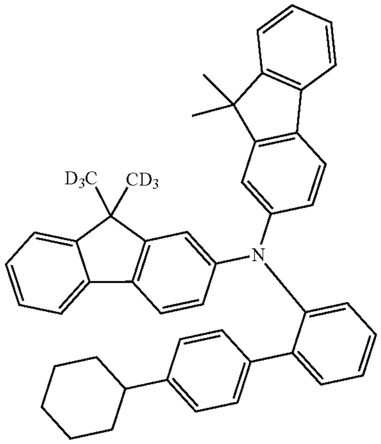
P-83
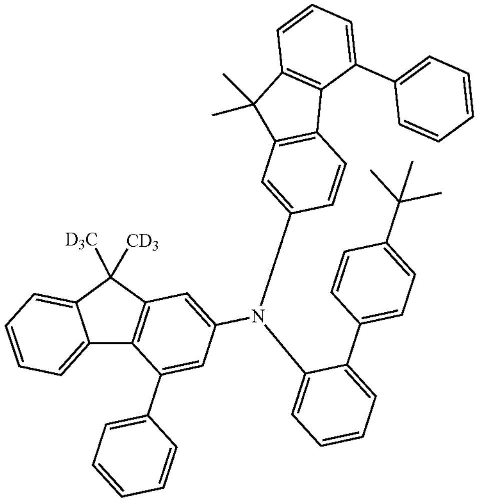
P-84
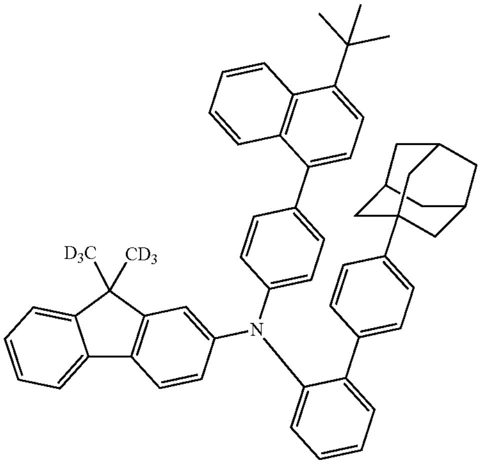

-continued
P-85
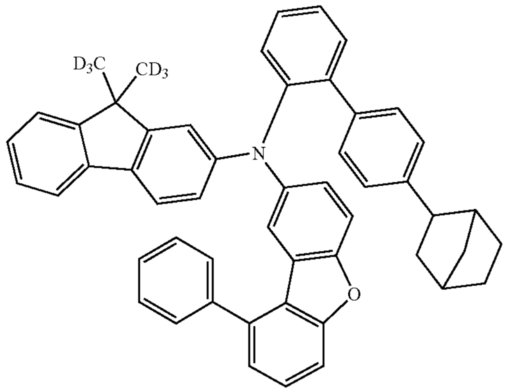
P-86
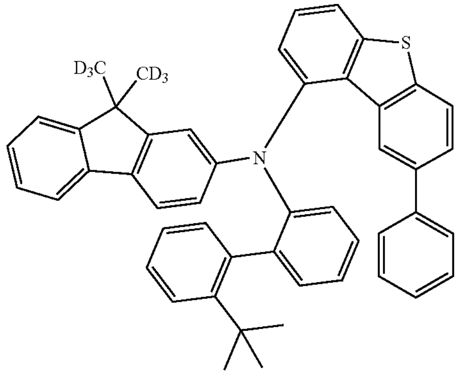
P-87
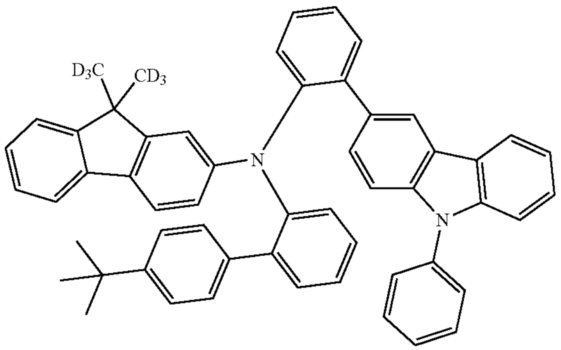
P-88
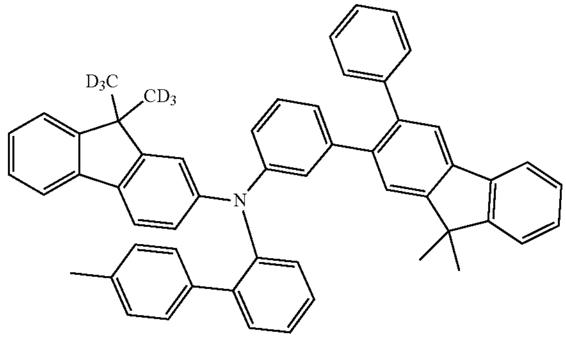
-continued
P-89
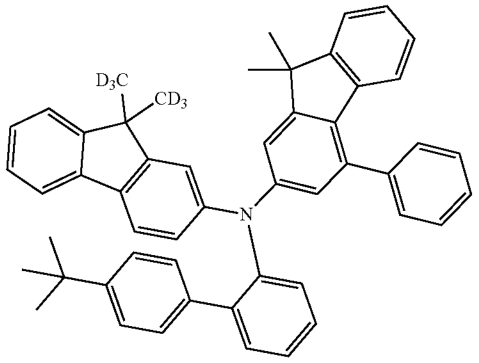
P-90
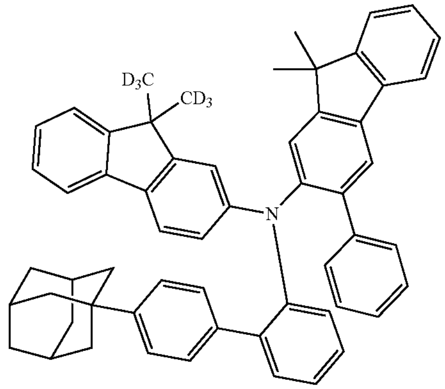
P-91
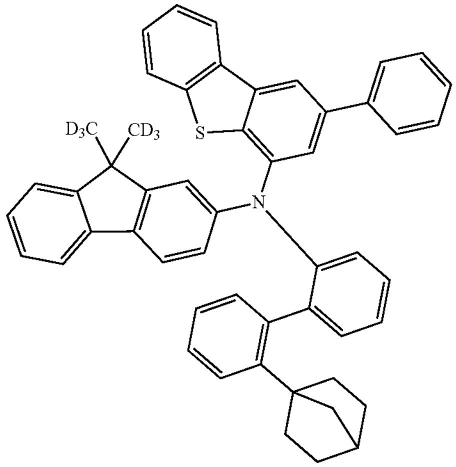

-continued
P-92
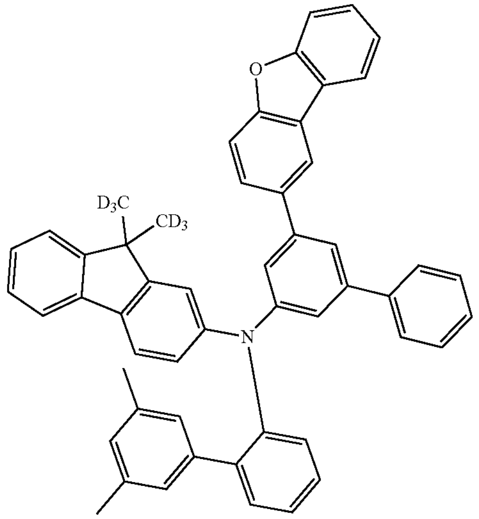
P-93
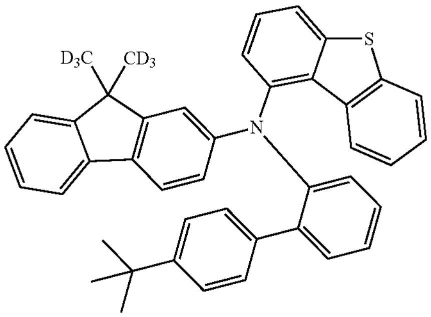
P-94
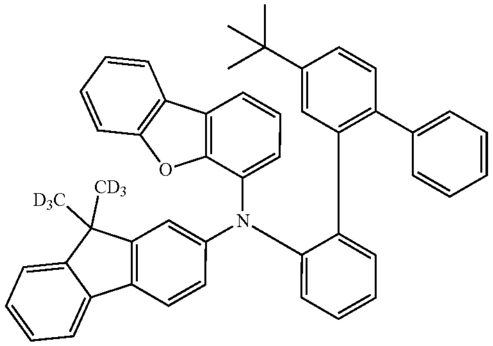
P-95
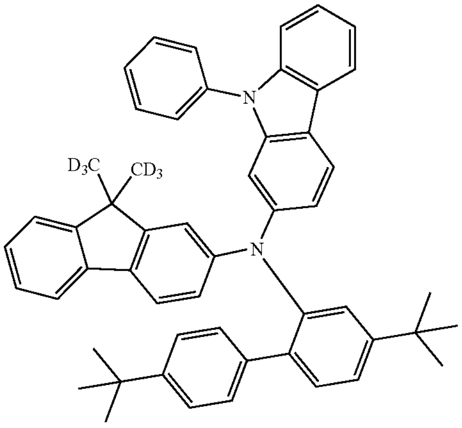
-continued
P-96
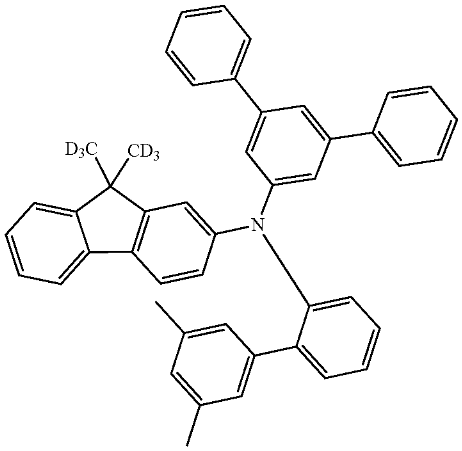
P-97
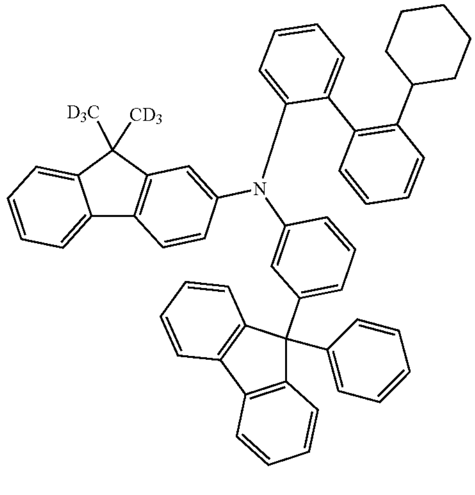
P-98
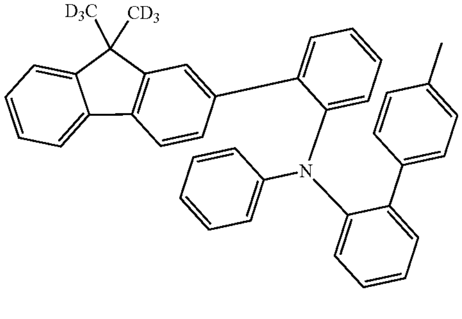

-continued
P-99
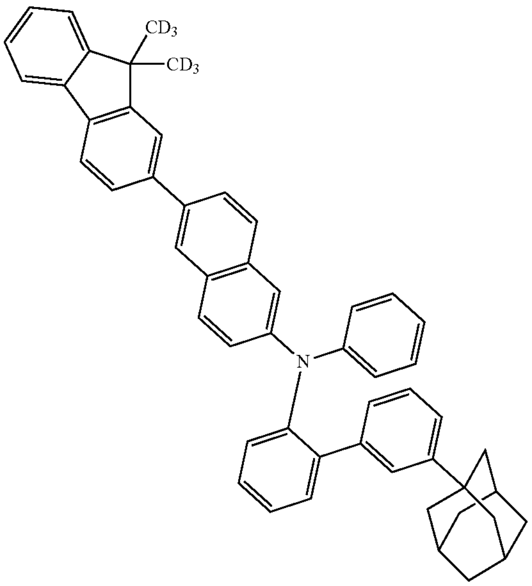
P-100
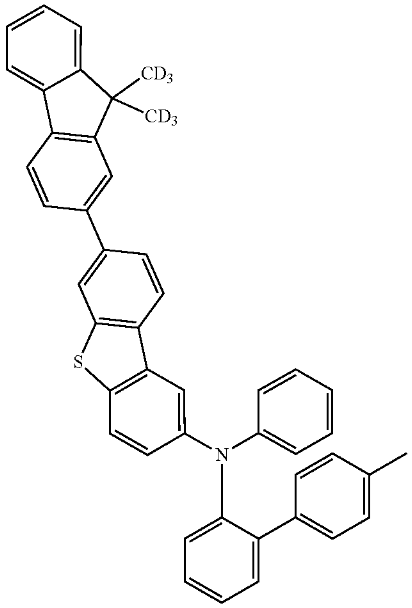
-continued
P-101
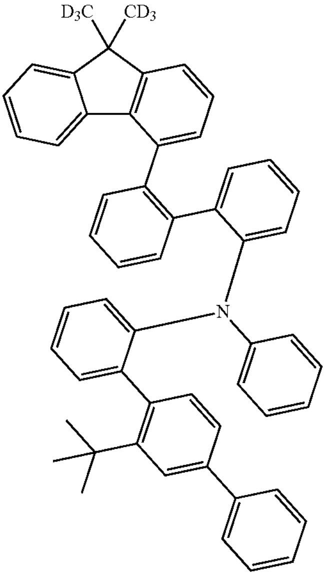
P-102
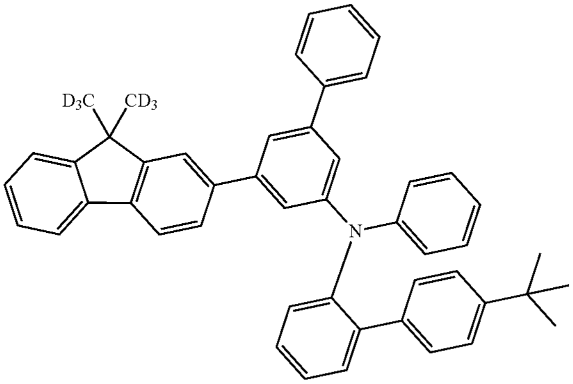
P-103
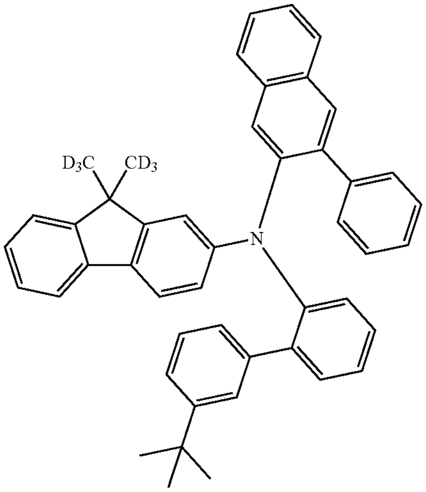

-continued
P-104
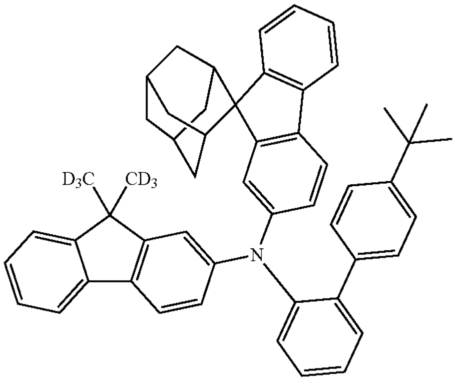
P-105
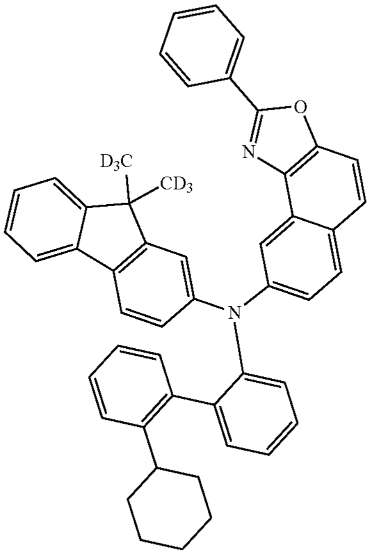
P-106
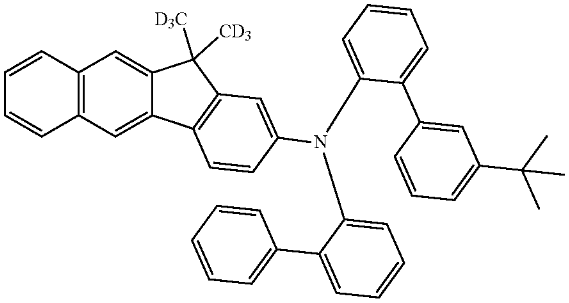
-continued
P-107
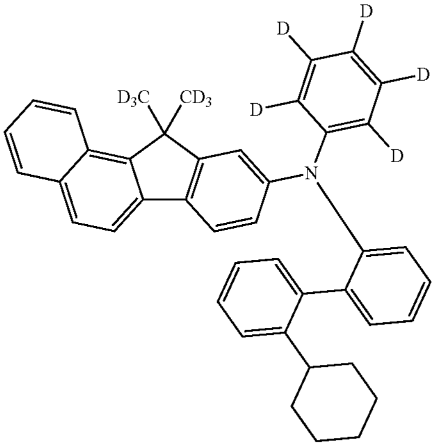
P-108
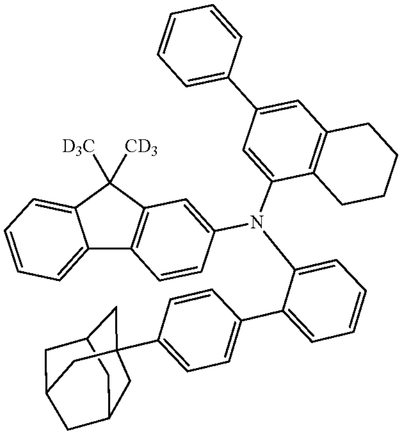
P-109
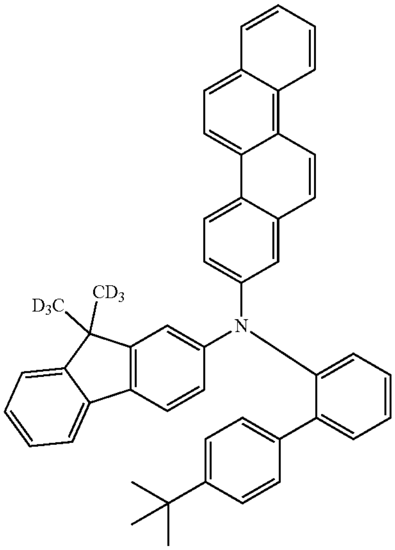

-continued
P-110
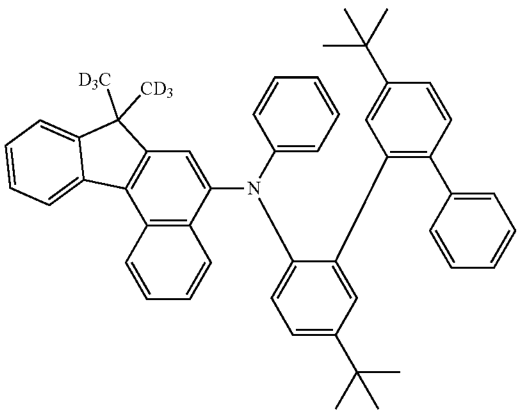
P-111
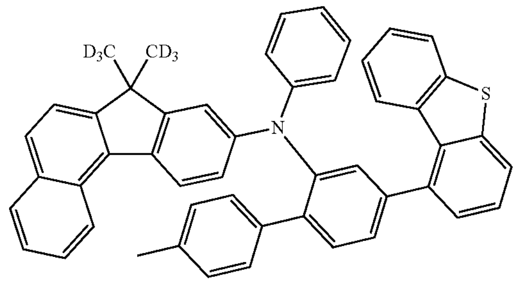
P-112
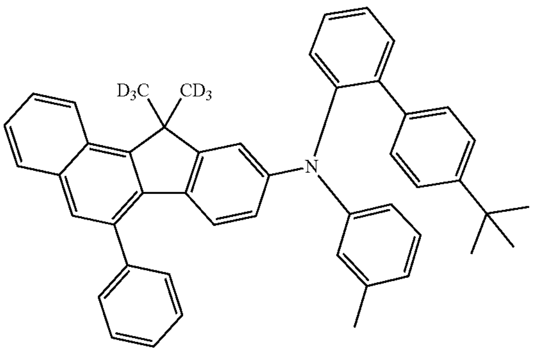
P-113
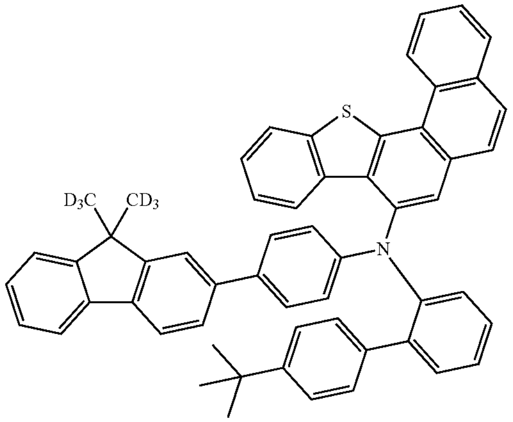
-continued
P-114
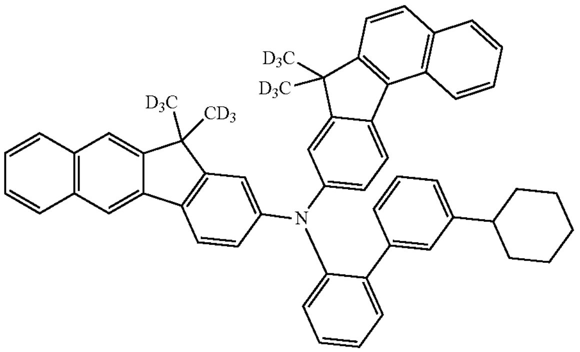
P-115
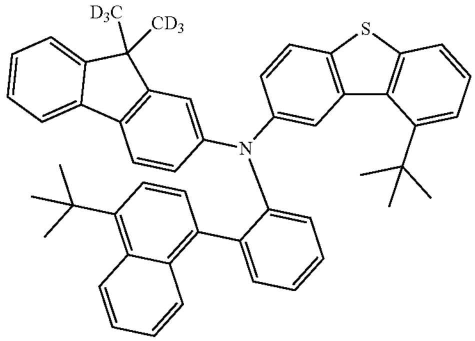
P-116
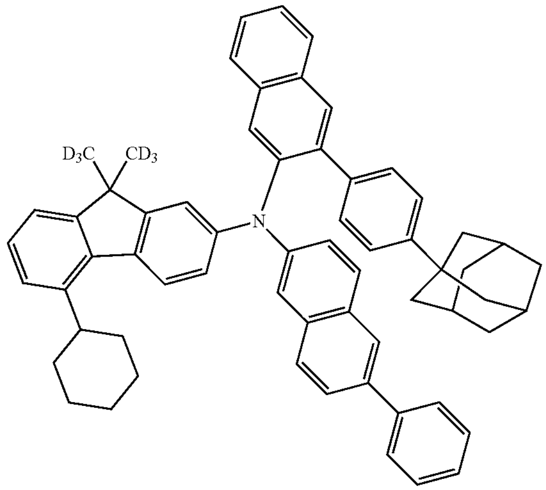

-continued
P-117
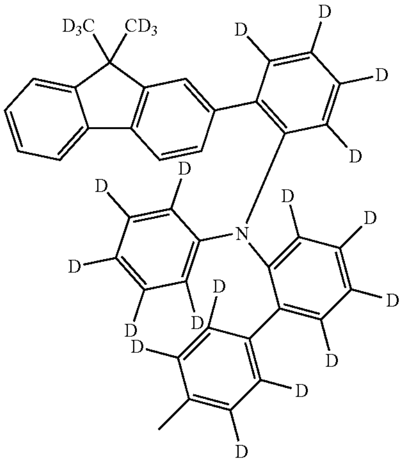
P-118
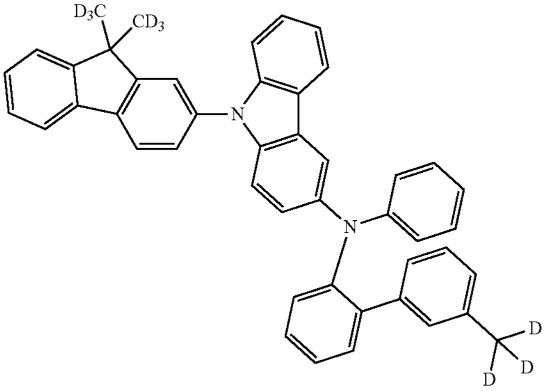
P-119
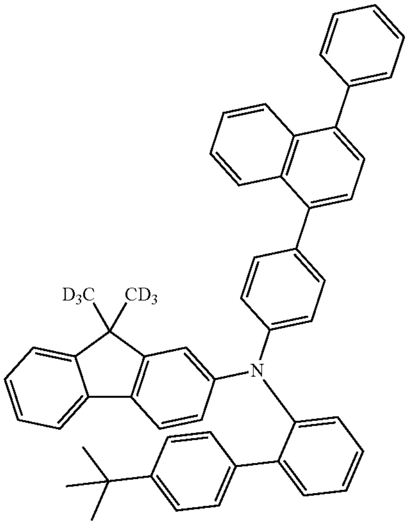
-continued
P-120
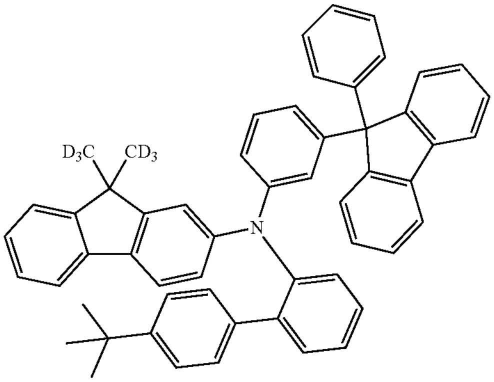
P-121
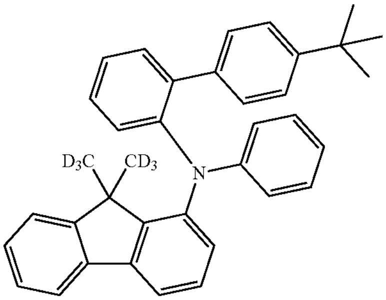
P;-122
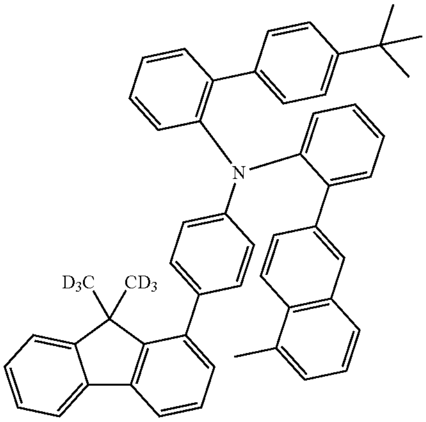
P-123
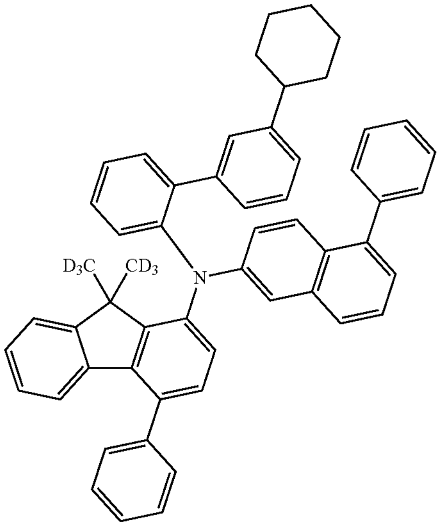

P-124
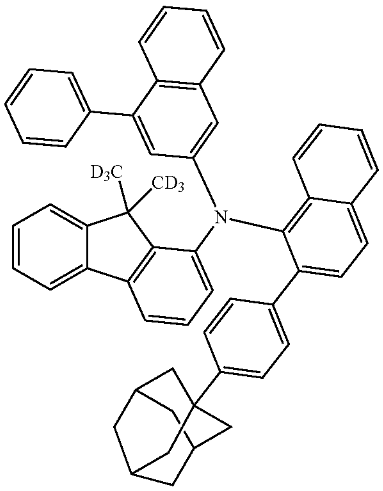
P-125
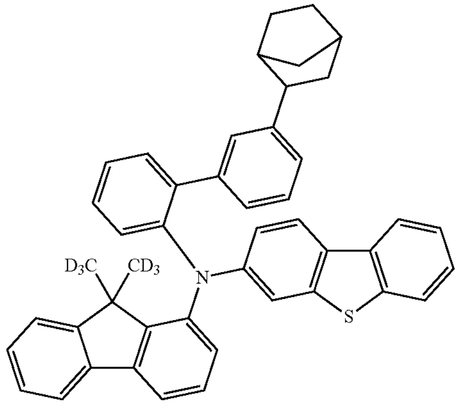
P-126
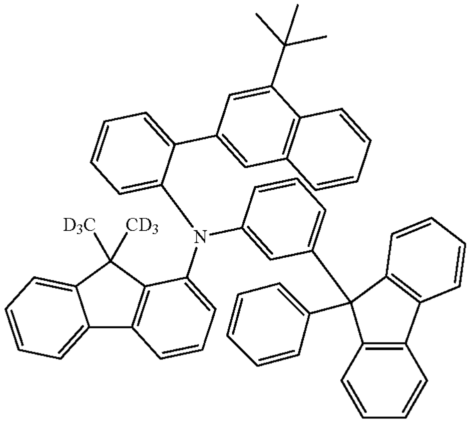
P-127
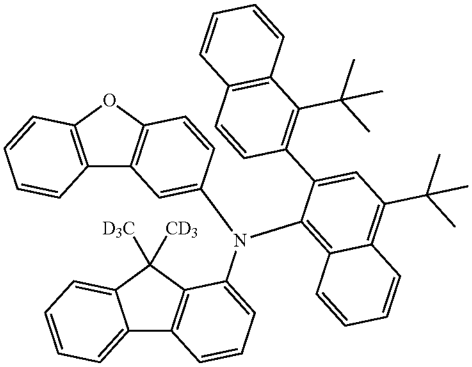
P-128
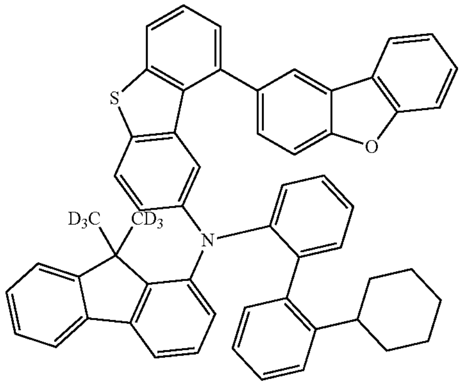
P-129
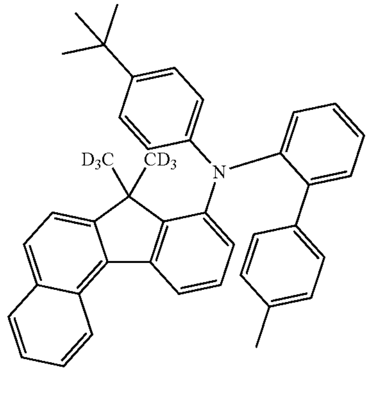
P-130
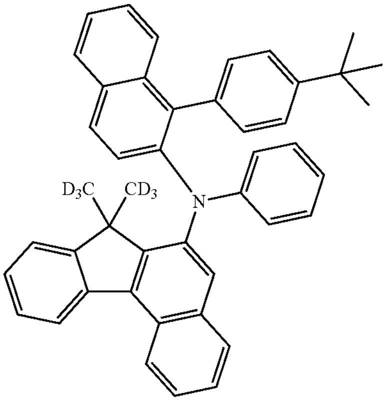

P-131
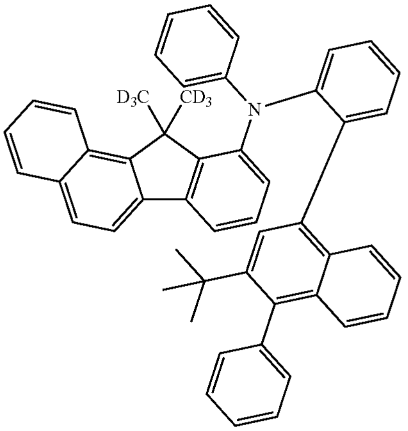
P-132
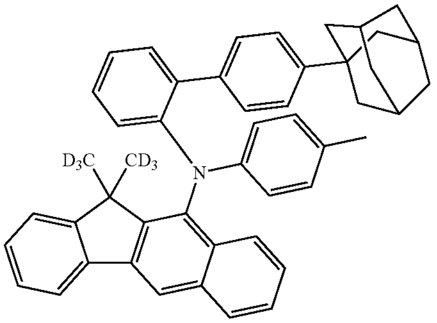
P-133
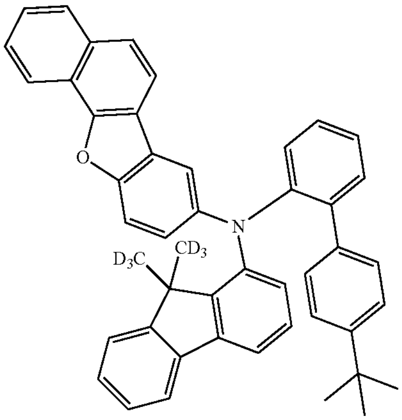
P-134
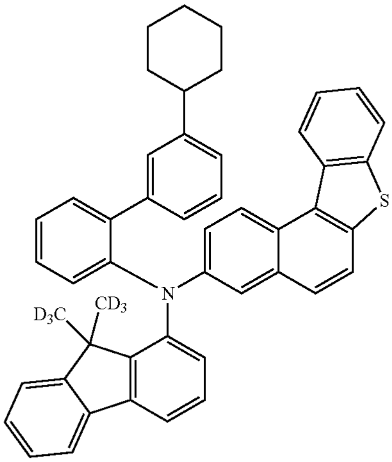
P-135
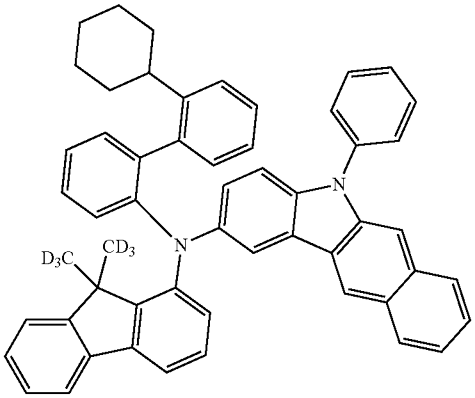
P-136
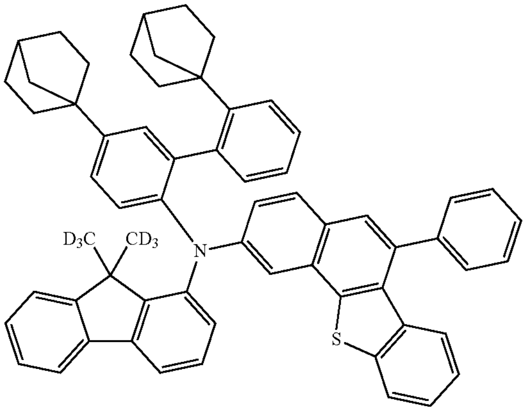

-continued
P-137
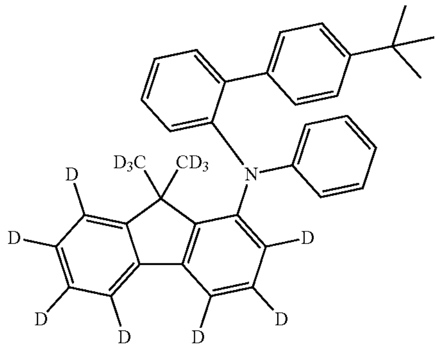
P-138
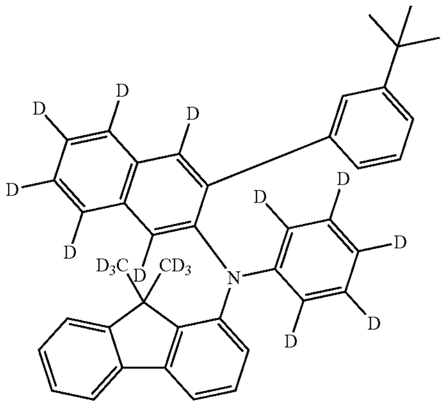
P-139
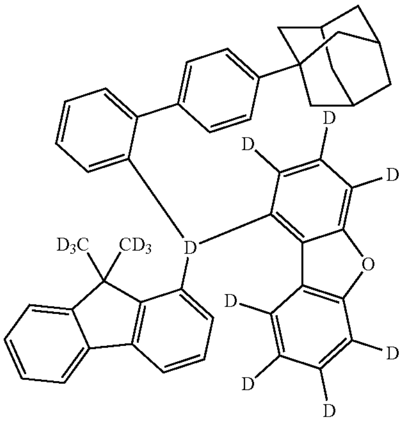
P-140
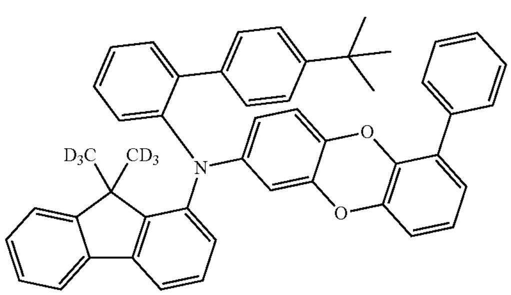
-continued
P-141
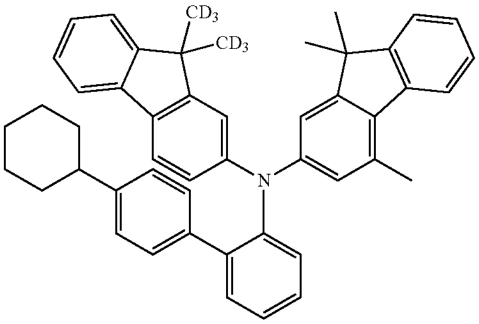
P-142
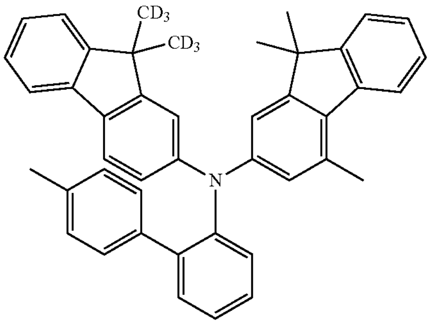
P-143
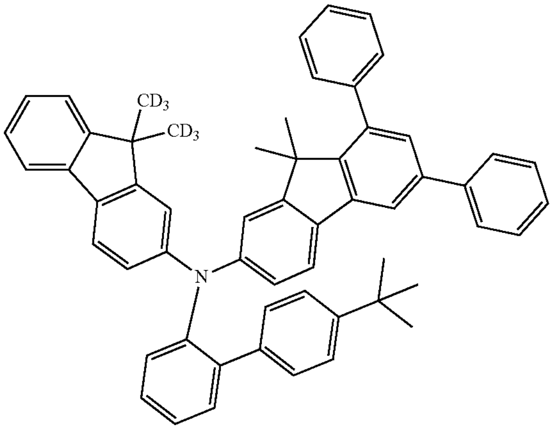
P-144
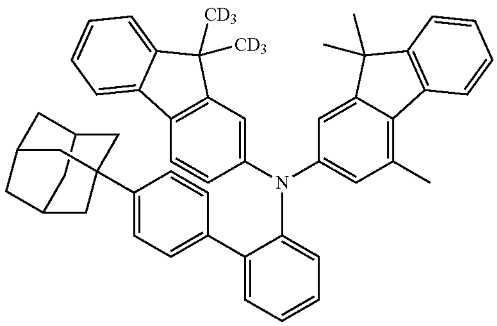

P-145
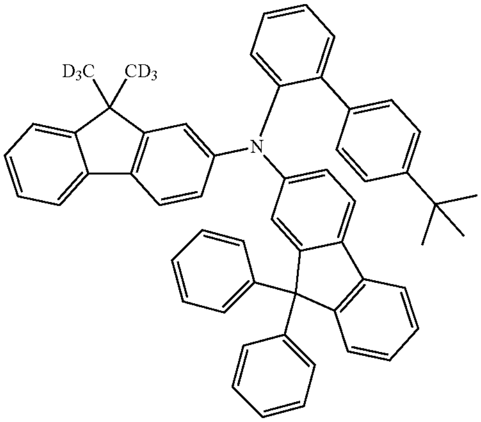
P-146
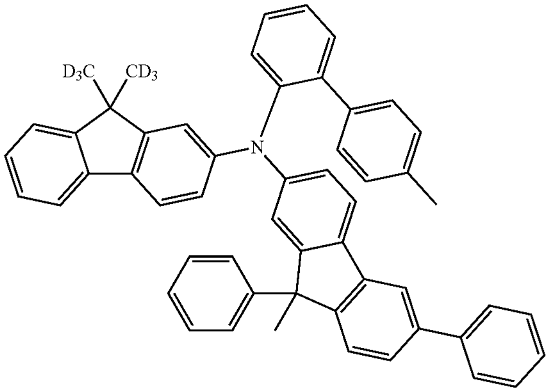
P-147
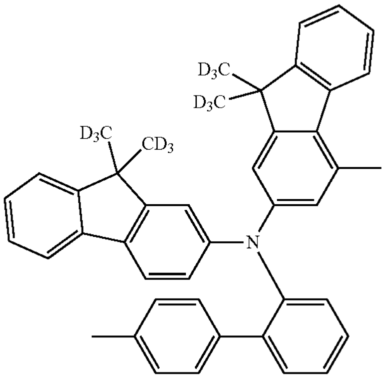
P-148
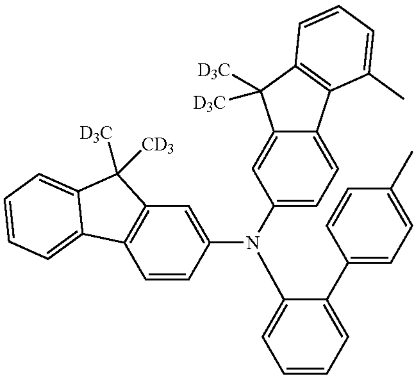
P-149
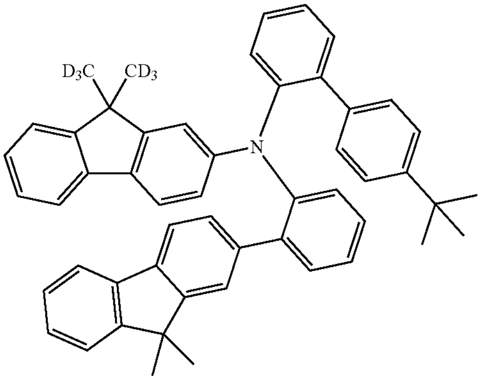
P-150
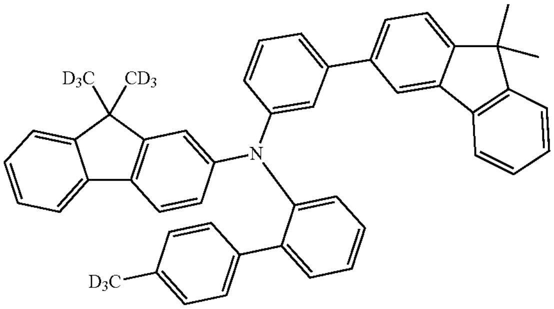
P-151
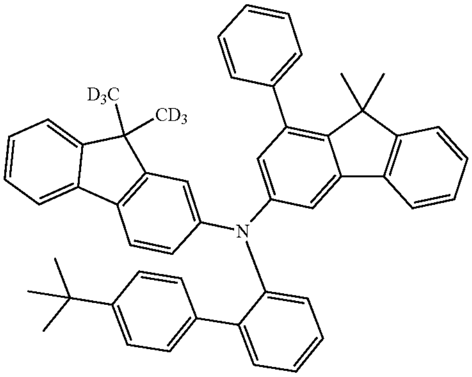
P-152
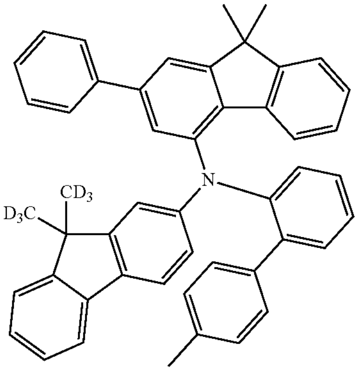

-continued
P-153
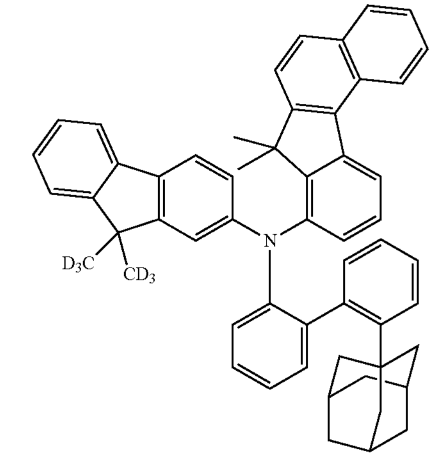
P-154
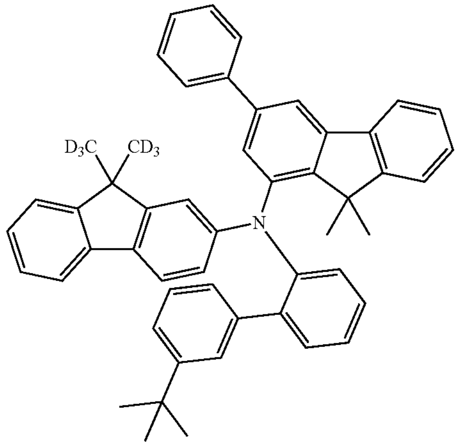
P-155
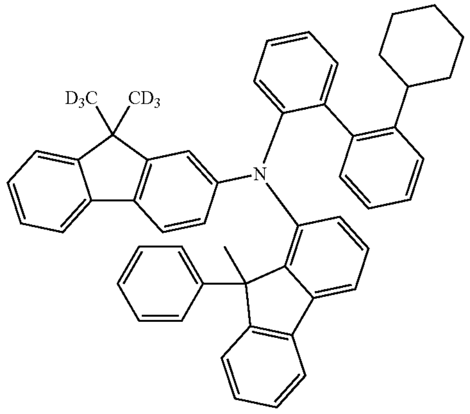
-continued
P-156
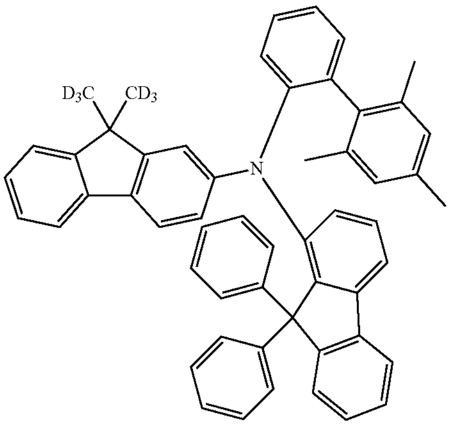
P-157
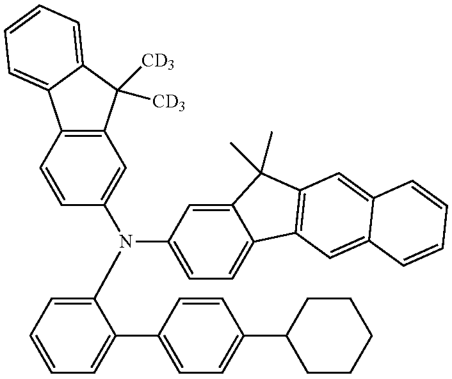
P-158
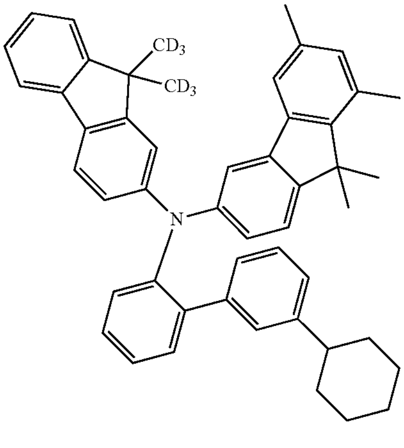

-continued

P-159

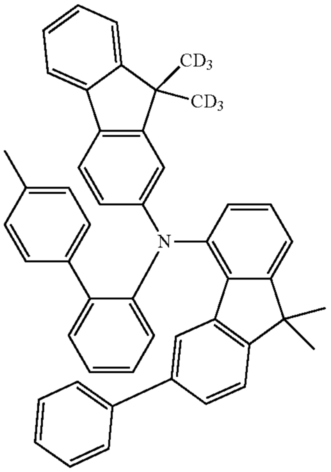

P-160

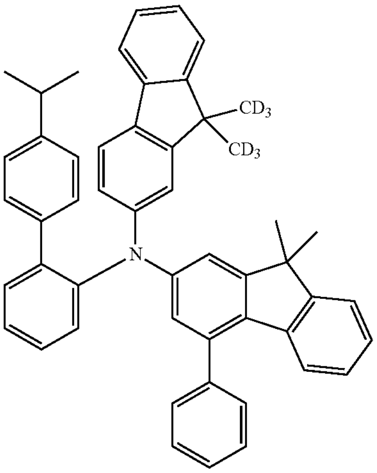

In another aspect, the present invention provides a method for reusing a compound of Formula 1 comprising:

- recovering a crude organic light emitting material comprising the compound of Formula 1 from a deposition apparatus used in the process for depositing the organic emitting material to prepare an organic light emitting device;
- removing impurities from the crude organic light emitting material;
- recovering the organic light emitting material after the impurities are removed; and
- purifying the recovered organic light emitting material to have a purity of 99.9% or higher.

The step of removing impurities from the crude organic light emitting material recovered from the deposition apparatus may preferably comprise performing a pre-purification process to obtain a purity of 98% or more by recrystallization in a recrystallization solvent.

The recrystallization solvent may be preferably a polar solvent having a polarity index (PI) of 5.5 to 7.2.

The recrystallization solvent may preferably be used by mixing a polar solvent having a polarity value of 5.5 to 7.2 and a non-polar solvent having a polarity value of 2.0 to 4.7.

When a mixture of a polar solvent and a non-polar solvent is used, the recrystallization solvent may be used in an amount of 15% (v/v) or less of the non-polar solvent compared to the polar solvent.

The recrystallization solvent is preferably a single solvent of N-Methylpyrrolidone (NMP); or a polar solvent mixed any one selected from the group consisting of 1,3-Dimethyl-2-imidazolidinone, 2-pyrrolidone, N, N-Dimethyl formamide, Dimethyl acetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or a mixture of a polar solvent and a non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

Referring to FIG. 1, the organic electronic element (100) according to the present invention comprises a first electrode (110), a second electrode (170), an organic material layer comprising single compound or 2 or more compounds represented by Formula 1 between the first electrode (110) and the second electrode (170). Wherein, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
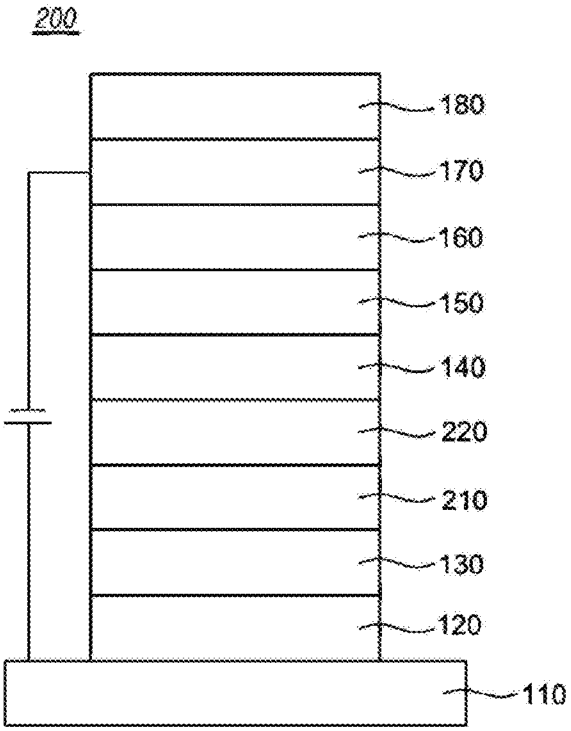

The organic material layer may sequentially comprise a hole injection layer (120), a hole transport layer (130), an emitting layer (140), an electron transport layer (150), and an electron injection layer (160) on the first electrode (110). Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150), etc. may serve as a hole blocking layer (see FIG. 2).

Also, the organic electronic element according to an embodiment of the present invention may further include a protective layer or a light efficiency enhancing layer (180). The light efficiency enhancing layer may be formed on a surface of both sides of the first electrode that is not in contact with the organic material layer or on a surface of both sides of the second electrode that is not in contact with the organic material layer. The compound or materials for organic electronic element according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), or the light efficiency enhancing layer. Preferably, for example, a composition for an organic electronic element comprising a compound according to Formula 1 of the present invention can be used as a host material of an emitting auxiliary layer.

Figure 3:
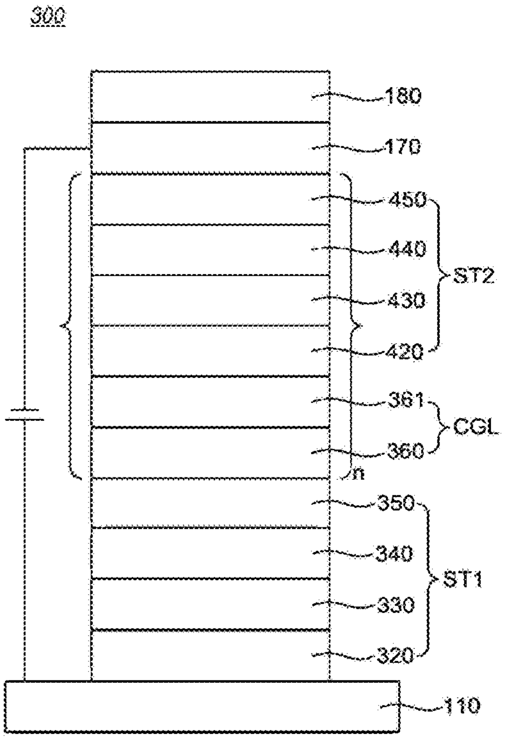
Figure 4:
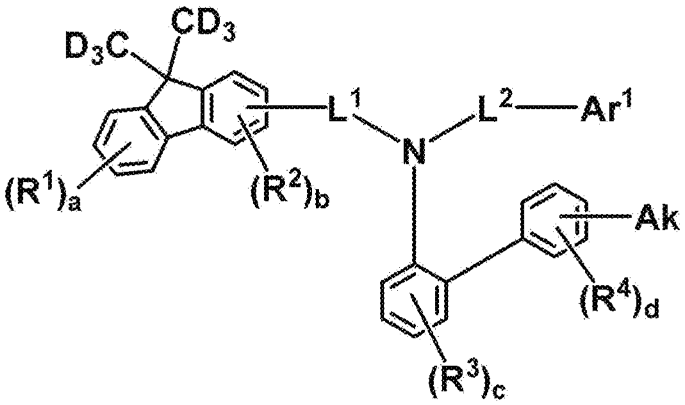
FIG. 4 shows a Formula according to one aspect of the present invention.

The organic material layer may comprise 2 or more stacks comprising a hole transport layer, an emitting layer and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, etc. may vary depending on which substituent is bonded at which position, therefore the choice of core and the combination of sub-substituents associated therewith is also very important, and in particular, when the optimal combination of energy levels and T1 values, and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (120), the hole transport layer (130), the emitting layer (140), the electron transport layer (150), and the electron injection layer (160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound or a composition for an organic electronic element as an electron transport material.

As another specific example, the present invention provides an organic electronic element used by mixing the same or different compounds of the compound represented by Formula 1 to the organic material layer.

Also, the present invention provides an emitting-auxiliary layer composition comprising a compound represented by Formula 1, and provides an organic electronic element comprising the emitting-auxiliary layer.

Also, the present invention also provides an electronic device comprising a display device comprising the organic electronic element; and a control unit for driving the display device.

According to another aspect, the present invention provides a display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis examples of the compound represented by Formula 1 according to the present invention and preparation examples of the organic electronic element will be described in detail by way of example, but are not limited to the following examples.

[Synthesis Example 1] a Compound Represented by Formula 1

The compound (final products) represented by Formula 1 according to the present invention is synthesized as in the Reaction Scheme 1, but is not limited thereto.

<Reaction Scheme 1>

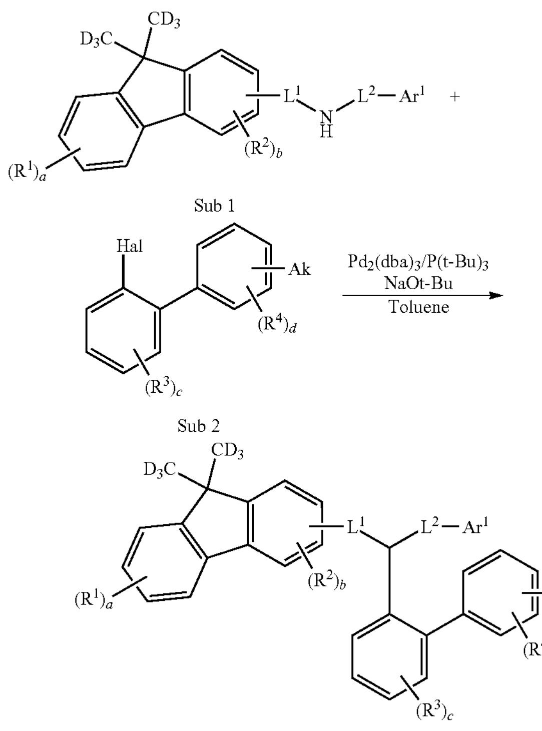

Sub 1

Sub 2

Final Products

Wherein, $R^1$, $R^2$, $R^3$, $R^4$, a, b, c, d, $Ar^1$, $L^1$, $L^2$ and Ak are the same as defined in Formula 1, Hal is one of Cl, Br, and I.

I. Synthesis of Final Product

1. Synthesis of P-1

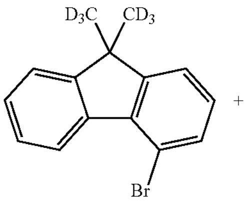

Sub 1-1a

-continued

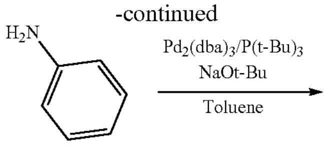

Sub 1-1b

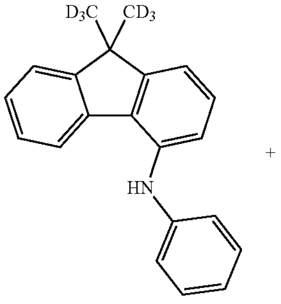

Sub 1-1

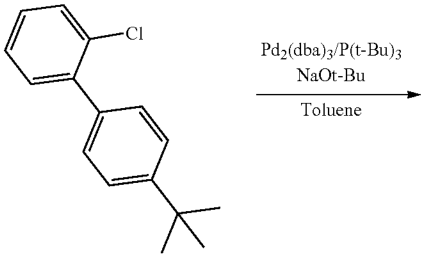

Sub 2-1

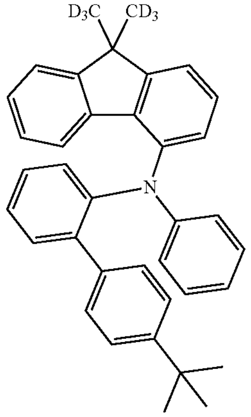

P-1

1) Synthesis of Sub 1-1

Sub 1-1a (100.0 g, 358.2 mmol) was dissolved in toluene (1791 mL) in a round-bottom flask, and then Sub 1-1b (33.4 g, 358.2 mmol), $Pd_2(dba)_3$ (9.8 g, 10.7 mmol), $P(t\text{-}Bu)_3$ (4.4 g, 21.5 mmol), and NaOt-Bu (68.8 g, 716.3 mmol) were added and stirred at 120° C. After the reaction was completed, the organic layer was extracted with $CH_2Cl_2$ and water, dried with $MgSO_4$, concentrated, and the resulting compound was recrystallized using a silica gel column to obtain 77.9 g of the product. (Yield: 74.6%)

2) Synthesis of P-1

Sub 1-1 (50.0 g, 171.6 mmol), Sub 2-1 (42.0 g, 171.6 mmol), $Pd_2(dba)_3$ (4.7 g, 5.2 mmol), $P(t\text{-}Bu)_3$ (2.1 g, 10.3 mmol), NaOt-Bu (33.0 g, 343.1 mmol), and toluene (858 mL) were added to a round-bottomed flask in the same manner as Sub 1-1 to obtain 62.2 g of the product. (Yield: 72.5%)

2. Synthesis of P-17

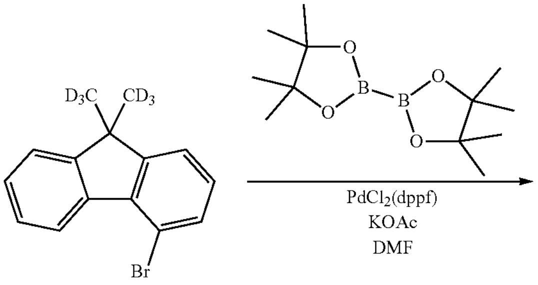

Sub 1-1a

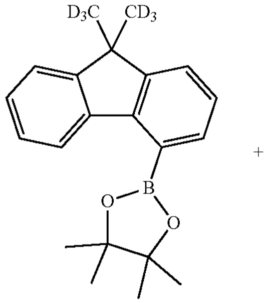

Sub 1-1ab

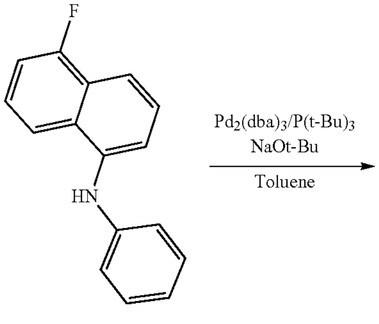

Sub 1-16b

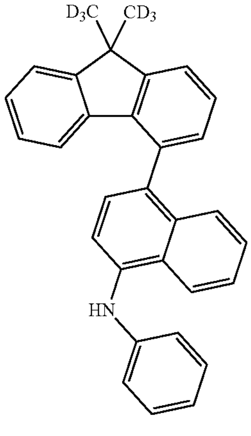

Sub 1-16

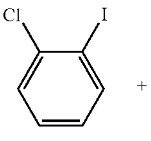

Sub 2-5a

-continued

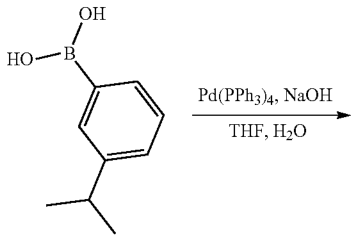

Sub 2-5b

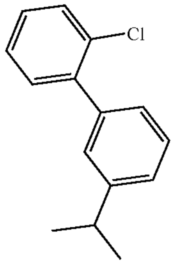

Sub 2-5b

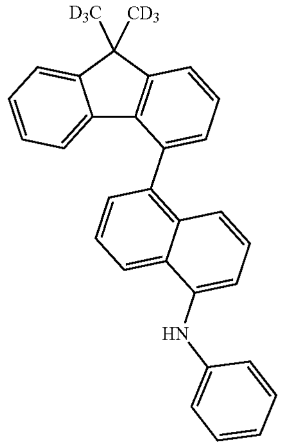

Sub 1-16

+

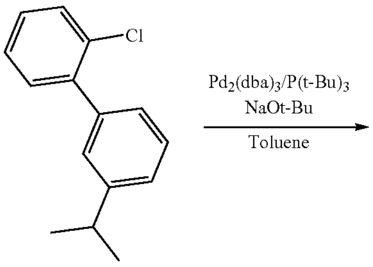

Sub 2-5

-continued

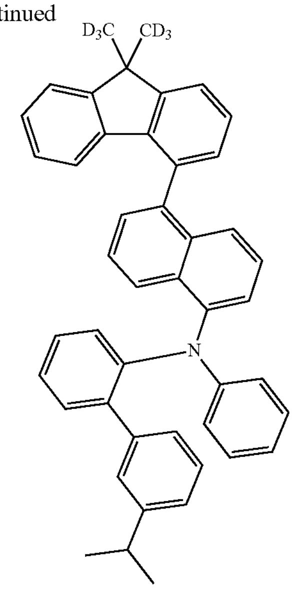

P-17

1) Synthesis of Sub 1-1ab

Sub 1-1a (100.0 g, 358.2 mmol) was placed in a round-bottom flask and dissolved in DMF (1791 ml). 4,4,4',4',5,5,5',5'-octamethyl-2,2'-bi (1,3,2-dioxaborolane) (118.2 g, 465.6 mmol), $Pd(dppf)Cl_2$ (13.1 g, 17.9 mmol), KOAc (105.5 g, 1074.5 mmol) were added, and the mixture was stirred at 150° C. for 2 hours. After the reaction was completed, the organic layer was extracted with $CH_2Cl_2$ and water, dried with $MgSO_4$, concentrated, and the resulting compound was recrystallized using a silica gel column to obtain 95.4 g of the product. (Yield: 81.6%)

2) Synthesis of P-16

Sub 1-1ab (80.0 g, 245.2 mmol), Sub 1-16b (58.2 g, 245.2 mmol), $Pd_2(dba)_3$ (6.7 g, 7.4 mmol), $P(t\text{-}Bu)_3$ (3.0 g, 14.7 mmol), NaOt-Bu (47.1 g, 490.4 mmol), toluene (1226 mL) were added to a round-bottomed flask in the same manner as Sub 1-1 to obtain 73.0 g of the product. (Yield: 71.3%)

3) Synthesis of Sub 2-5

Sub 2-5a (50.0 g, 209.7 mmol) was placed in a round-bottom flask, dissolved in THF (1048 mL) and Sub 2-5b (34.4 g, 209.7 mmol), $Pd(PPh_3)_4$ (14.5 g, 12.6 mmol), NaOH (25.2 g, 629.1 mmol), and water (524 ml) were added and the reaction was carried out at 80° C. When the reaction was complete, the reaction product was extracted with $CH_2Cl_2$ and water, dried with $MgSO_4$, concentrated, and the resulting compound was recrystallized using a silica gel column to obtain 39.9 g of the product. (Yield: 82.4%)

4) Synthesis of P-17

Sub 1-16 (50.0 g, 119.7 mmol), Sub 2-5 (27.6 g, 119.7 mmol), $Pd_2(dba)_3$ (3.3 g, 3.6 mmol), $P(t\text{-}Bu)_3$ (1.5 g, 7.2 mmol), NaOt-Bu (23.0 g, 239.5 mmol), toluene (599 mL) were added to a round-bottomed flask in the same manner as Sub 1-1 to obtain 51.9 g of the product. (Yield: 70.8%)

3. Synthesis of P-25

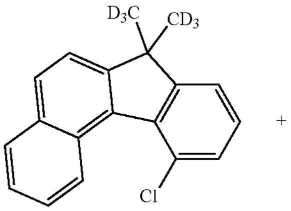

Sub 1-24a

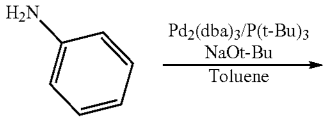

Sub 1-1b

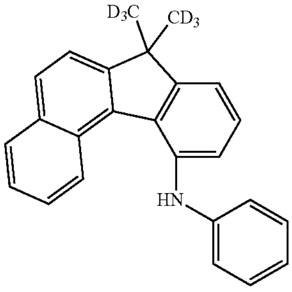

Sub 1-24

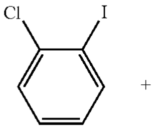

Sub 2-5a

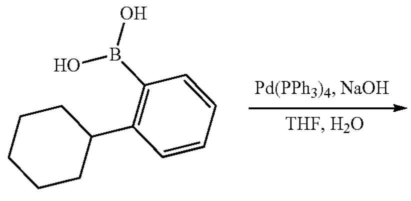

Sub 2-18b

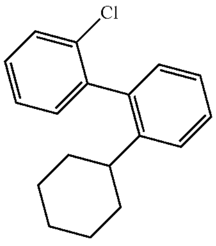

Sub 2-18

-continued

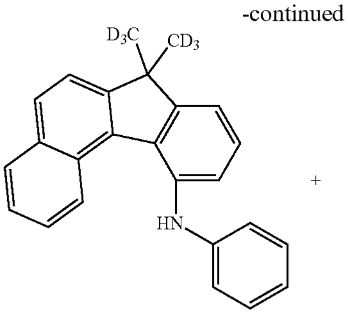

Sub 1-24

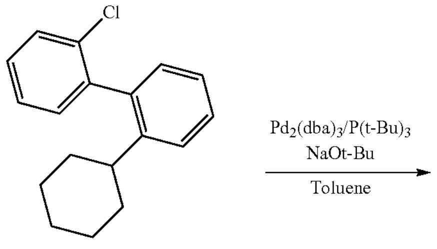

Sub 2-18

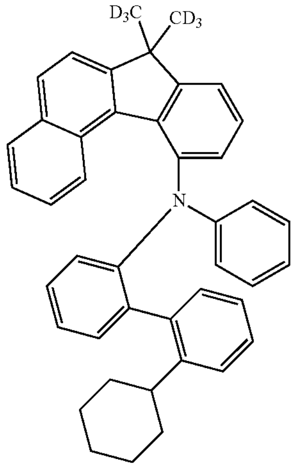

P-25

1) Synthesis of Sub 1-24

Sub 1-24a (100.0 g, 351.1 mmol), Sub 1-1b (32.7 g, 351.1 mmol), $Pd_2(dba)_3$ (9.7 g, 10.5 mmol), $P(t-Bu)_3$ (4.3 g, 21.1 mmol), NaOt-Bu (67.5 g, 702.2 mmol), toluene (1755 mL) were added to a round-bottomed flask in the same manner as Sub 1-1 to obtain 84.8 g of the product. (Yield: 70.7%)

2) Synthesis of Sub 2-18

Sub 2-5a (50.0 g, 209.7 mmol) was placed in a round-bottom flask, dissolved in THF (1048 mL) and Sub 2-18b (42.8 g, 209.7 mmol), $Pd(PPh_3)_4$ (14.5 g, 12.6 mmol), NaOH (25.2 g, 629.1 mmol), and water (524 ml) were added, and the same experiment as Sub 2-5 was performed to obtain 46.2 g of the product. (Yield: 81.3%) 3) Synthesis of P-25

Sub 1-24 (50.0 g, 146.4 mmol), Sub 2-18 (39.6 g, 146.4 mmol), $Pd_2(dba)_3$ (4.0 g, 4.4 mmol), $P(t-Bu)_3$ (1.8 g, 8.8 mmol), NaOt-Bu (28.1 g, 292.8 mmol), toluene (732 mL) were added to a round-bottomed flask in the same manner as Sub 1-1 to obtain 58.8 g of the product. (Yield: 69.8%)

4. Synthesis of P-44

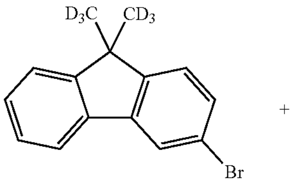

Sub 1-39a

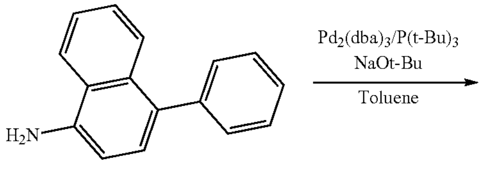

Sub 1-39b

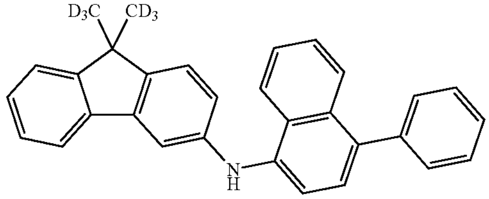

Sub 1-39

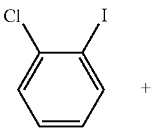

Sub 2-5a

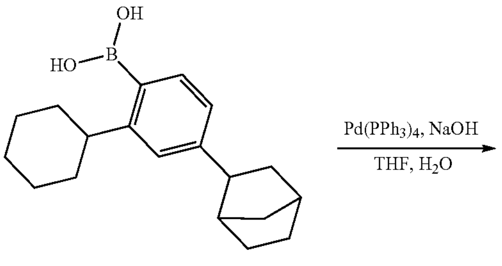

Sub 2-28b

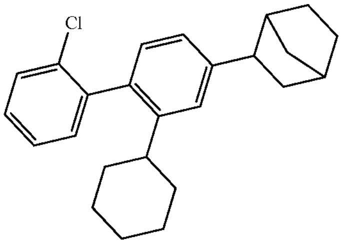

Sub 2-28

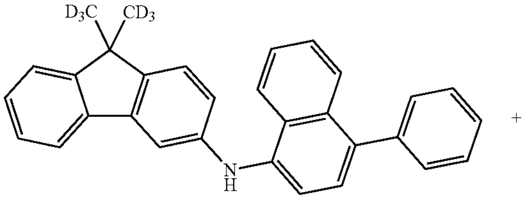

Sub 1-39

-continued

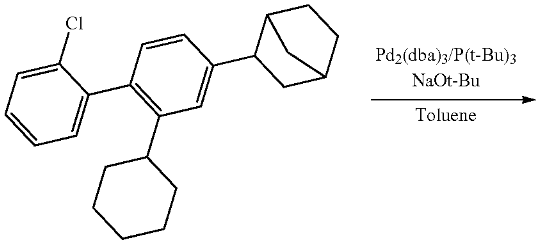

Sub 2-28

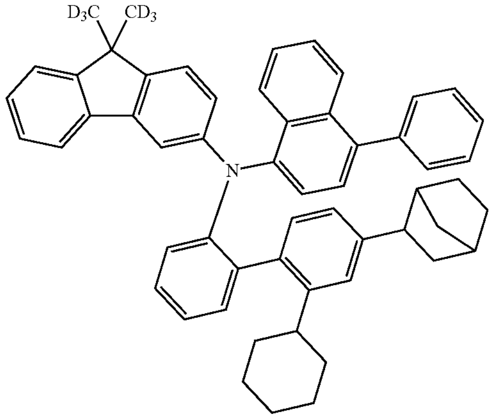

P-44

1) Synthesis of Sub 1-39

Sub 1-39a (100.0 g, 358.2 mmol), Sub 1-39b (78.5 g, 358.2 mmol), $Pd_2(dba)_3$ (9.8 g, 10.7 mmol), $P(t-Bu)_3$ (4.4 g, 21.5 mmol), NaOt-Bu (68.8 g, 716.3 mmol), toluene (1791 mL) were added to a round-bottomed flask in the same manner as Sub 1-1 to obtain 106.9 g of the product. (Yield: 71.5%)

2) Synthesis of Sub 2-28

Sub 2-5a (50.0 g, 209.7 mmol) was placed in a round-bottom flask, dissolved in THF (1048 mL) and Sub 2-28b (62.5 g, 209.7 mmol), $Pd(PPh_3)_4$ (14.5 g, 12.6 mmol), NaOH (25.2 g, 629.1 mmol), and water (524 ml) were added, and the same experiment as Sub 2-5 was performed to obtain 61.8 g of the product. (Yield: 80.8%) 3) Synthesis of P-44

Sub 1-39 (50.0 g, 119.7 mmol), Sub 2-28 (43.7 g, 119.7 mmol), $Pd_2(dba)_3$ (3.3 g, 3.6 mmol), $P(t-Bu)_3$ (1.5 g, 7.2 mmol), NaOt-Bu (23.0 g, 239.5 mmol), toluene (599 mL) were added to a round-bottomed flask in the same manner as Sub 1-1 to obtain 62.7 g of the product. (Yield: 70.2%)

5. Synthesis of P-61

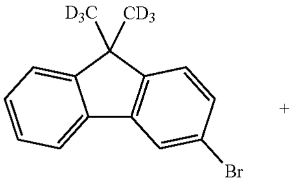

Sub 1-39a

-continued

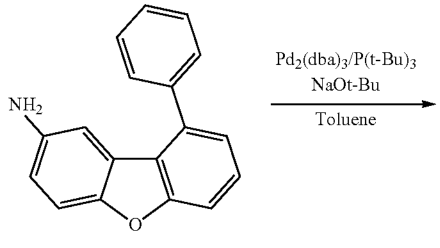

Sub 1-56b

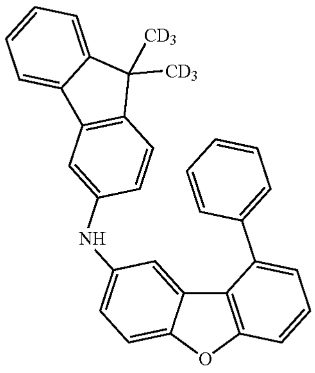

Sub 1-56

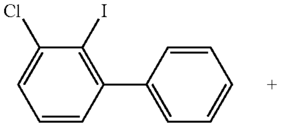

Sub 2-30a

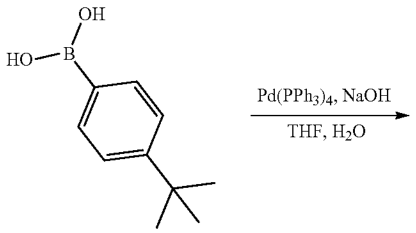

Sub 2-30b

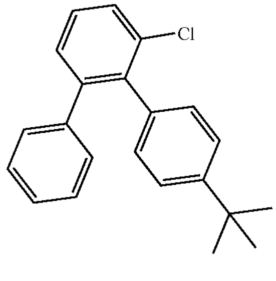

Sub 2-30

-continued

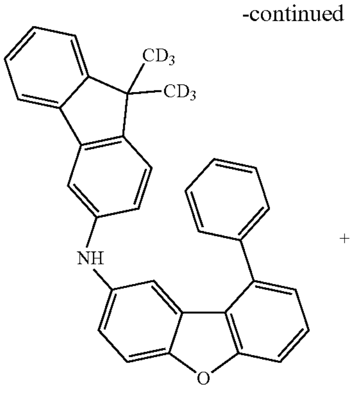

Sub 1-56

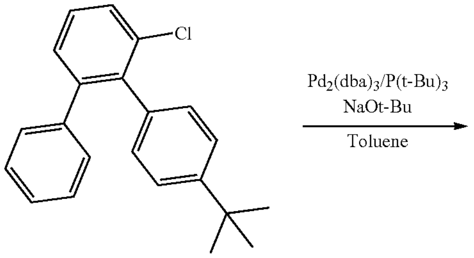

Sub 2-30

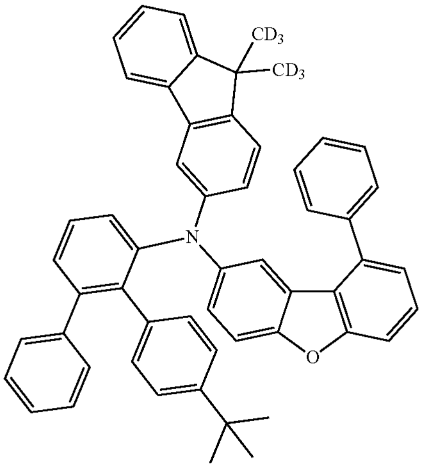

P-61

1) Synthesis of Sub 1-56

Sub 1-39a (100.0 g, 358.2 mmol), Sub 1-56b (92.9 g, 358.2 mmol), $Pd_2(dba)_3$ (9.8 g, 10.7 mmol), $P(t-Bu)_3$ (4.4 g, 21.5 mmol), NaOt-Bu (68.8 g, 716.3 mmol), toluene (1791 mL) were added to a round-bottomed flask in the same manner as Sub 1-1 to obtain 116.4 g of the product. (Yield: 71.0%)

2) Synthesis of Sub 2-30

Sub 2-30a (50.0 g, 159.0 mmol) was placed in a round-bottom flask, dissolved in THF (795 mL) and Sub 2-30b (28.3 g, 159.0 mmol), $Pd(PPh_3)_4$ (11.0 g, 9.5 mmol), NaOH (19.1 g, 476.9 mmol), and water (397 ml) were added, and the same experiment as Sub 2-5 was performed to obtain 39.5 g of the product. (Yield: 77.4%) 3) Synthesis of P-61

Sub 1-56 (50.0 g, 109.3 mmol), Sub 2-30 (35.1 g, 109.3 mmol), $Pd_2(dba)_3$ (3.0 g, 3.3 mmol), $P(t-Bu)_3$ (1.3 g, 6.6 mmol), NaOt-Bu (21.0 g, 218.5 mmol), toluene (546 mL) were added to a round-bottomed flask in the same manner as Sub 1-1 to obtain 57.0 g of the product. (Yield: 69.9%)

6. Synthesis of P-84

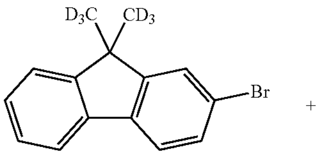

Sub 1-75a

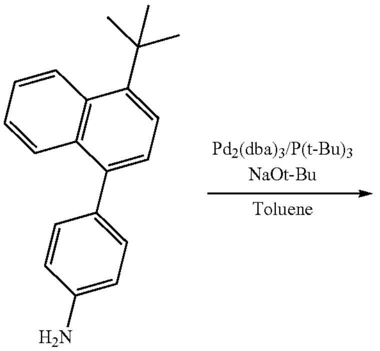

Sub 1-75b

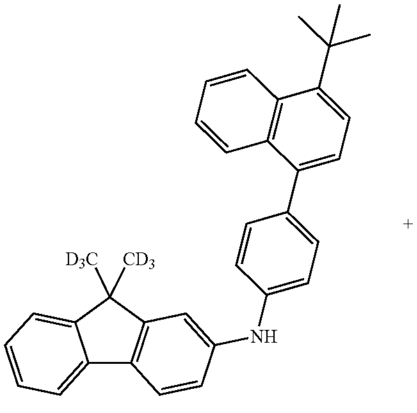

Sub 1-75

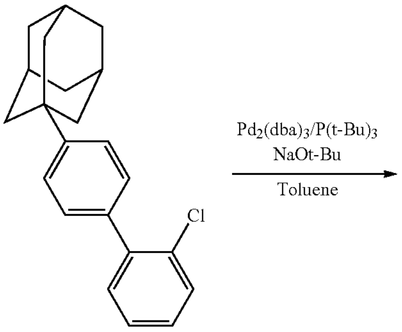

Sub 2-10

-continued

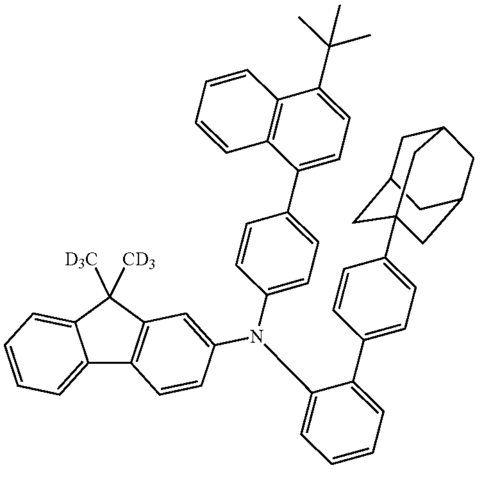

P-84

1) Synthesis of Sub 1-75

Sub 1-75a (100.0 g, 358.2 mmol), Sub 1-75b (98.6 g, 358.2 mmol), $Pd_2(dba)_3$ (9.8 g, 10.7 mmol), $P(t\text{-}Bu)_3$ (4.4 g, 21.5 mmol), NaOt-Bu (68.8 g, 716.3 mmol), toluene (1791 mL) were added to a round-bottomed flask in the same manner as Sub 1-1 to obtain 122.3 g of the product. (Yield: 72.1%)

2) Synthesis of P-84

Sub 1-75 (50.0 g, 109.3 mmol), Sub 2-10 (35.3 g, 109.3 mmol), $Pd_2(dba)_3$ (3.0 g, 3.3 mmol), $P(t\text{-}Bu)_3$ (1.3 g, 6.6 mmol), NaOt-Bu (21.0 g, 218.5 mmol), toluene (546 mL) were added to a round-bottomed flask in the same manner as Sub 1-1 to obtain 61.0 g of the product. (Yield: 73.5%)

7. Synthesis of P-89

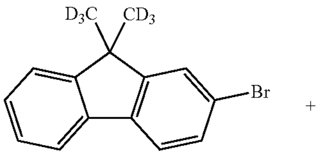

Sub 1-75a

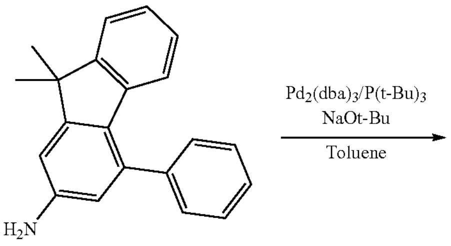

Sub 1-80b

-continued

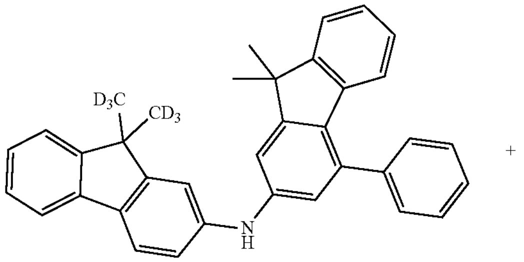

Sub 1-80

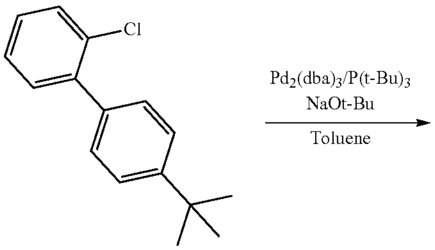

Sub 2-1

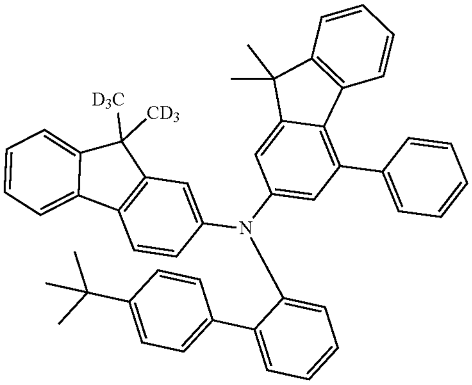

P-89

1) Synthesis of Sub 1-80

Sub 1-75a (100.0 g, 358.2 mmol), Sub 1-80b (102.2 g, 358.2 mmol), $Pd_2(dba)_3$ (9.8 g, 10.7 mmol), $P(t\text{-}Bu)_3$ (4.4 g, 21.5 mmol), NaOt-Bu (68.8 g, 716.3 mmol), toluene (1791 mL) were added to a round-bottomed flask in the same manner as Sub 1-1 to obtain 124.2 g of the product. (Yield: 72.7%)

2) Synthesis of P-89

Sub 1-80 (50.0 g, 103.4 mmol), Sub 2-1 (25.3 g, 103.4 mmol), $Pd_2(dba)_3$ (2.8 g, 3.1 mmol), $P(t\text{-}Bu)_3$ (1.3 g, 6.2 mmol), NaOt-Bu (19.9 g, 206.7 mmol), toluene (517 mL) were added to a round-bottomed flask in the same manner as Sub 1-1 to obtain 51.6 g of the product. (Yield: 72.1%)

8. Synthesis of P-92

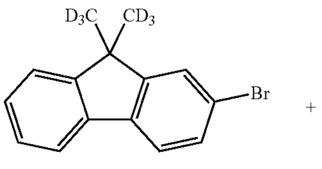

Sub 1-75a

-continued

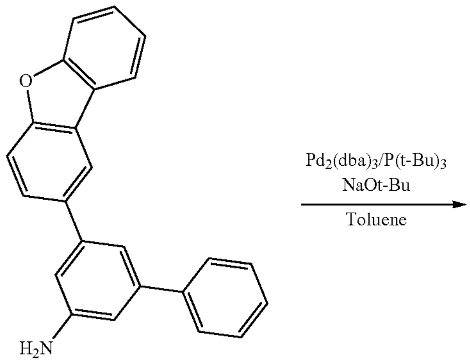

Sub 1-83b

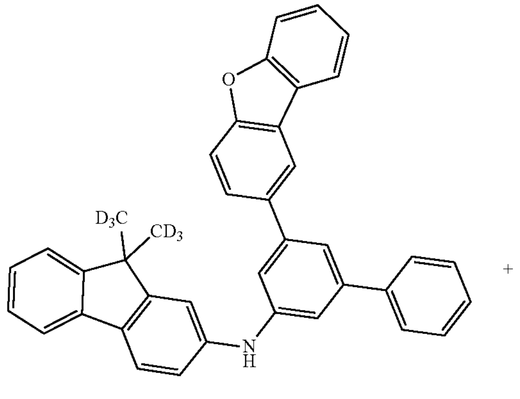

Sub 1-83

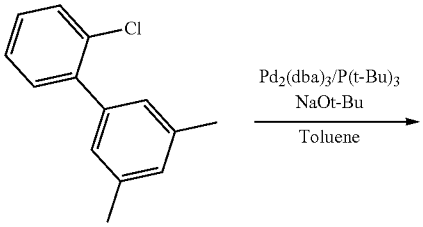

Sub 2-6

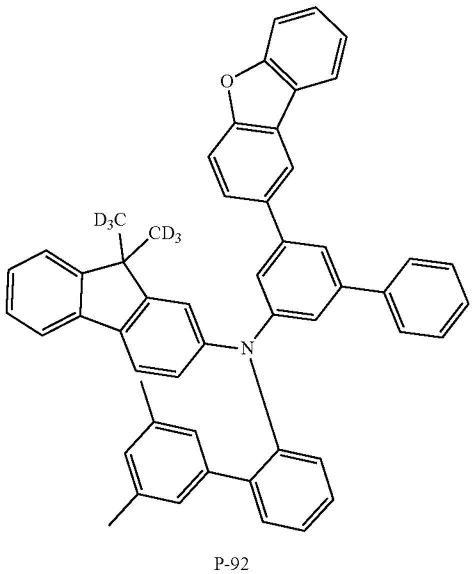

P-92

1) Synthesis of Sub 1-83

Sub 1-75a (100.0 g, 358.2 mmol), Sub 1-83b (127.3 g, 358.2 mmol), $Pd_2(dba)_3$ (9.8 g, 10.7 mmol), $P(t\text{-}Bu)_3$ (4.4 g, 21.5 mmol), NaOt-Bu (68.8 g, 716.3 mmol), toluene (1791 mL) were added to a round-bottomed flask in the same manner as Sub 1-1 to obtain 138.4 g of the product. (Yield: 72.4%)

2) Synthesis of P-92

Sub 1-83 (50.0 g, 93.7 mmol), Sub 2-6 (20.3 g, 93.7 mmol), $Pd_2(dba)_3$ (2.6 g, 2.8 mmol), $P(t\text{-}Bu)_3$ (1.1 g, 5.6 mmol), NaOt-Bu (18.0 g, 187.4 mmol), toluene (468 mL) were added to a round-bottomed flask in the same manner as Sub 1-1 to obtain 46.4 g of the product. (Yield: 69.4%)

9. Synthesis of P-115

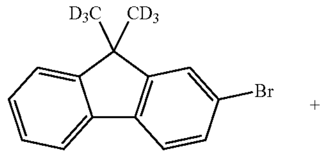

Sub 1-75a

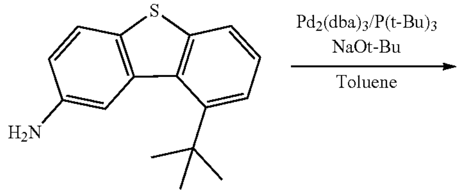

Sub 1-106b

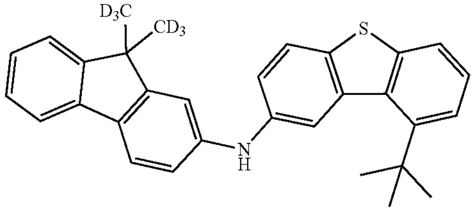

Sub 1-106

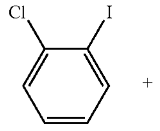

Sub 2-5a

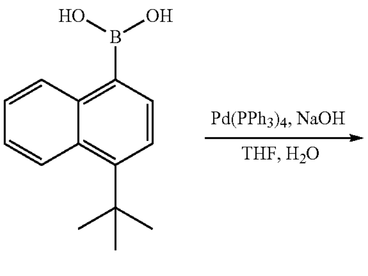

Sub 2-40b

-continued

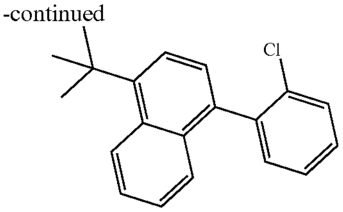

Sub 2-40

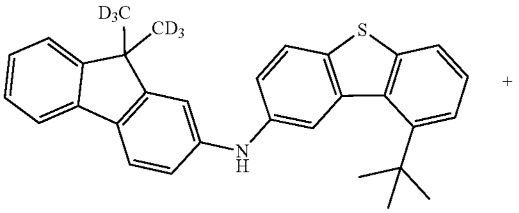

Sub 1-106

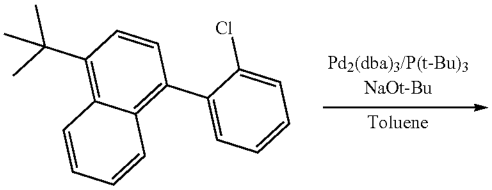

Sub 2-40

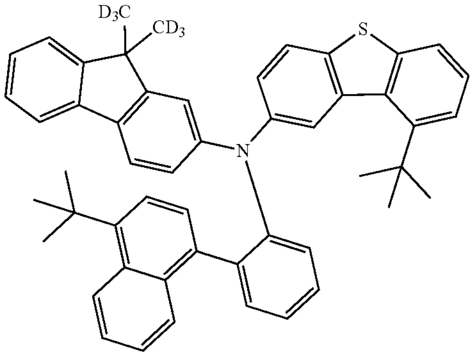

P-115

1) Synthesis of Sub 1-106

Sub 1-75a (100.0 g, 358.2 mmol), Sub 1-106b (91.5 g, 358.2 mmol), $Pd_2(dba)_3$ (9.8 g, 10.7 mmol), $P(t\text{-}Bu)_3$ (4.4 g, 21.5 mmol), NaOt-Bu (68.8 g, 716.3 mmol), toluene (1791 mL) were added to a round-bottomed flask in the same manner as Sub 1-1 to obtain 114.7 g of the product. (Yield: 70.6%)

2) Synthesis of Sub 2-40

Sub 2-5a (50.0 g, 209.7 mmol) was placed in a round-bottom flask, dissolved in THF (1048 ml) and Sub 2-40b (47.8 g, 209.7 mmol), $Pd(PPh_3)_4$ (14.5 g, 12.6 mmol), NaOH (25.2 g, 629.1 mmol) and water (524 ml) were added, and the same experiment as Sub 2-5 was performed to obtain 50.2 g of the product. (Yield: 81.2%)

3) Synthesis of P-115

Sub 1-106 (50.0 g, 110.2 mmol), Sub 2-40 (32.5 g, 110.2 mmol), $Pd_2(dba)_3$ (3.0 g, 3.3 mmol), $P(t\text{-}Bu)_3$ (1.3 g, 6.6 mmol), NaOt-Bu (21.2 g, 220.4 mmol), toluene (551 mL) were added to a round-bottomed flask in the same manner as Sub 1-1 to obtain 55.0 g of the product. (Yield: 70.1%)

10. Synthesis of P-126

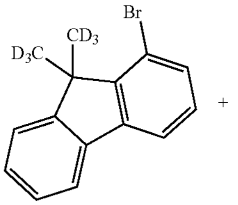

Sub 1-117a

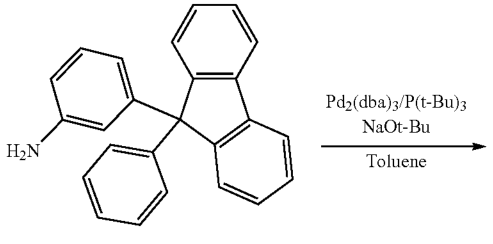

Sub 1-117b

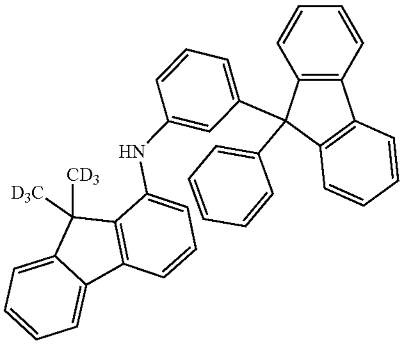

Sub 1-117

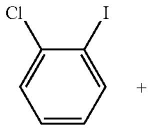

Sub 2-5a

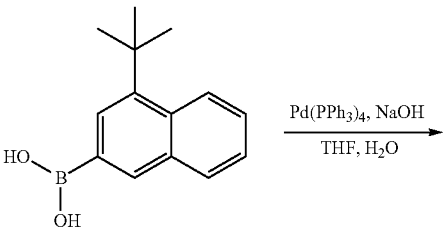

Sub 2-44b

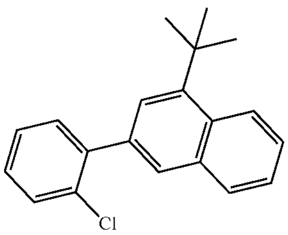

Sub 2-44

-continued

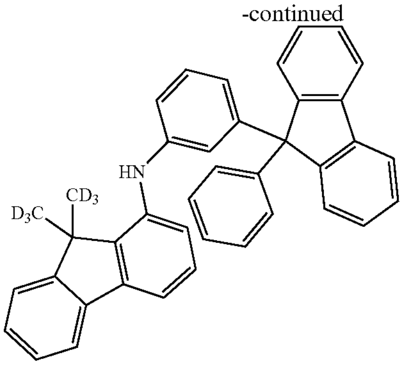

Sub 1-117

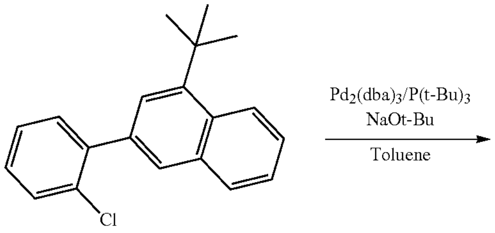

Sub 2-44

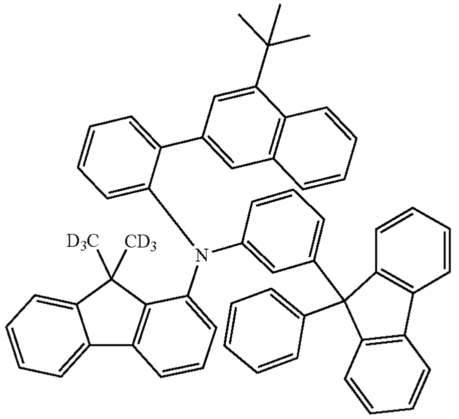

P-126

1) Synthesis of Sub 1-117

Sub 1-117a (100.0 g, 358.2 mmol), Sub 1-117b (91.5 g, 358.2 mmol), $Pd_2(dba)_3$ (9.8 g, 10.7 mmol), $P(t\text{-}Bu)_3$ (4.4 g, 21.5 mmol), NaOt-Bu (68.8 g, 716.3 mmol), toluene (1791 mL) were added to a round-bottomed flask in the same manner as Sub 1-1 to obtain 134.8 g of the product. (Yield: 70.8%)

2) Synthesis of Sub 2-44

Sub 2-5a (50.0 g, 209.7 mmol) was placed in a round-bottom flask, dissolved in THF (1048 ml) and Sub 2-40b (47.8 g, 209.7 mmol), $Pd(PPh_3)_4$ (14.5 g, 12.6 mmol), NaOH (25.2 g, 629.1 mmol) and water (524 ml) were added, and the same experiment as Sub 2-5 was performed to obtain 50.3 g of the product. (Yield: 81.3%)

3) Synthesis of P-126

Sub 1-117 (50.0 g, 94.0 mmol), Sub 2-44 (21.4 g, 94.0 mmol), $Pd_2(dba)_3$ (2.6 g, 2.8 mmol), $P(t\text{-}Bu)_3$ (1.1 g, 5.6 mmol), NaOt-Bu (18.1 g, 188.1 mmol), toluene (470 mL) were added to a round-bottomed flask in the same manner as Sub 1-1 to obtain 51.0 g of the product. (Yield: 68.7%)

Sub 1 of the reaction scheme 1 may be, but is not limited to, the compounds below, and the FD-MS (Field Desorption-Mass Spectrometry) values of compounds belonging to Sub 1 are as shown in Table 1.
Sub 1-1
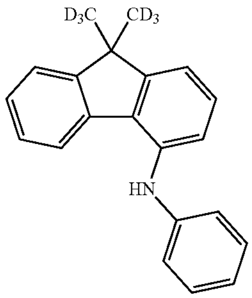
Sub 1-2
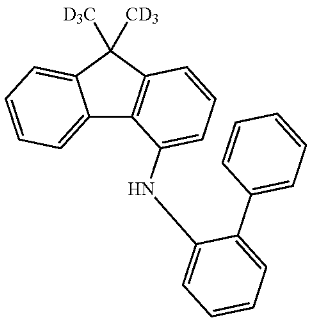
Sub 1-3
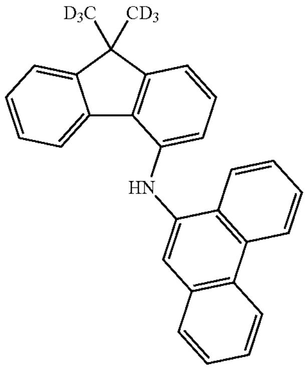
Sub 1-4
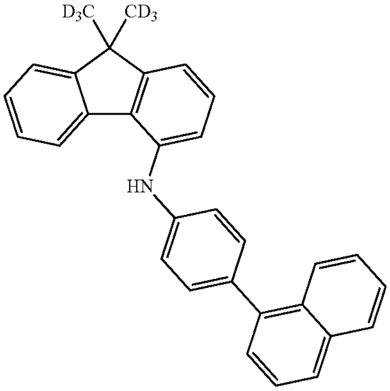
-continued
Sub 1-5
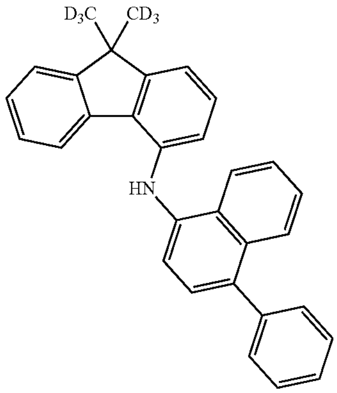
Sub 1-6
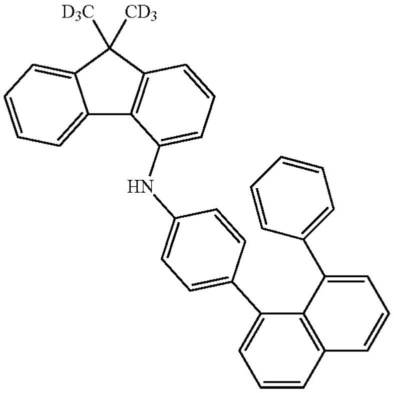
Sub 1-7
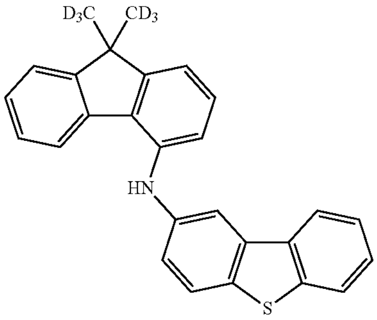
Sub 1-8
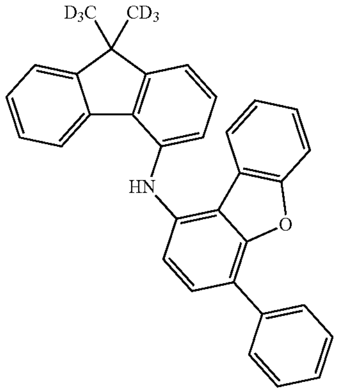

-continued
Sub 1-9
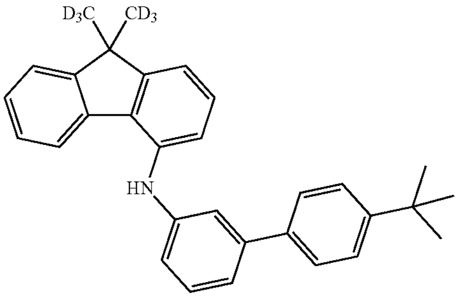
Sub 1-10
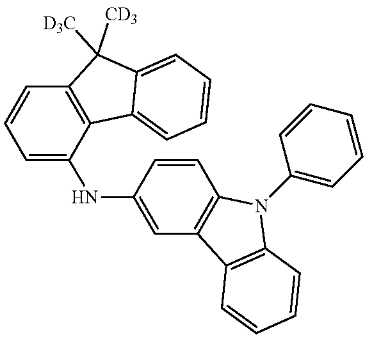
Sub 1-11
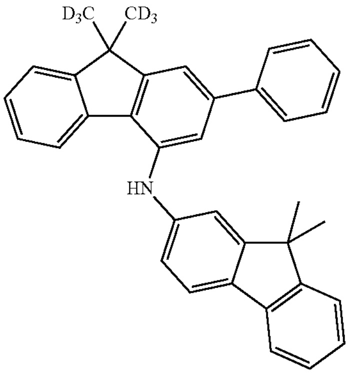
Sub 1-12
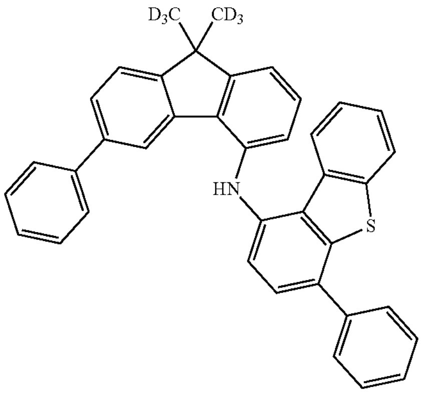
-continued
Sub 1-13
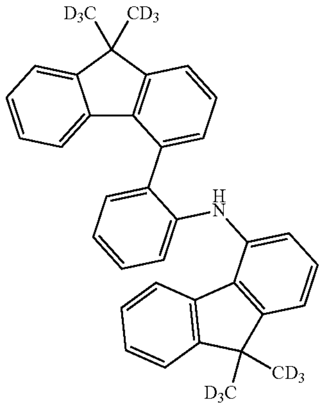
Sub 1-14
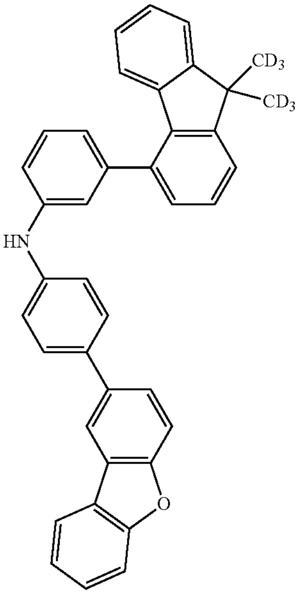
Sub 1-15
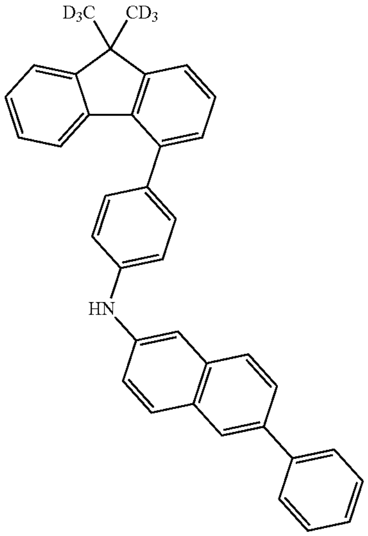

Sub 1-16
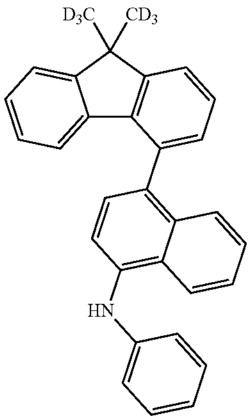
Sub 1-17
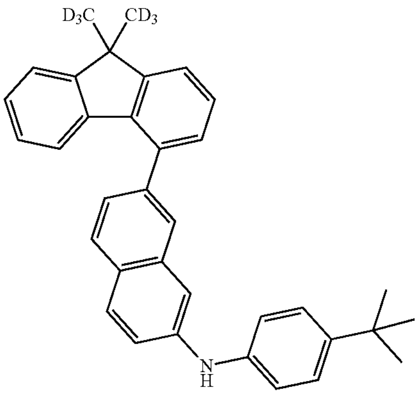
Sub 1-18
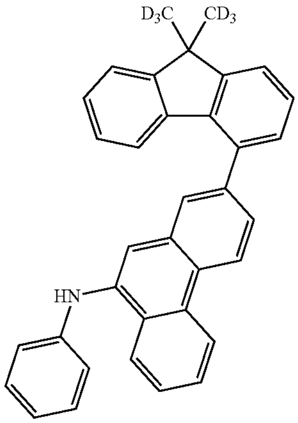
Sub 1-19
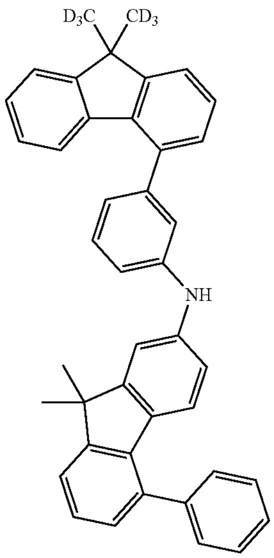
Sub 1-20
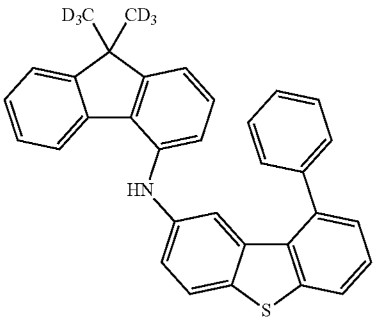
Sub 1-21
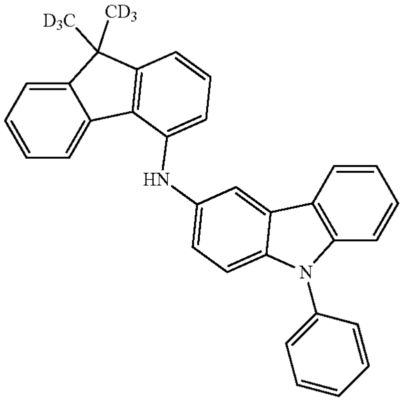
Sub 1-22
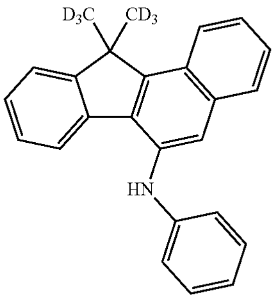

-continued
Sub 1-23
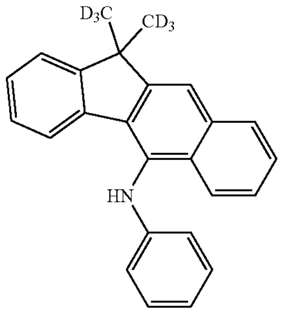
Sub 1-24
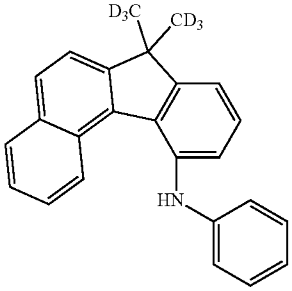
Sub 1-25
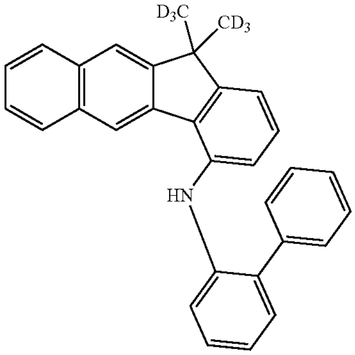
Sub 1-26
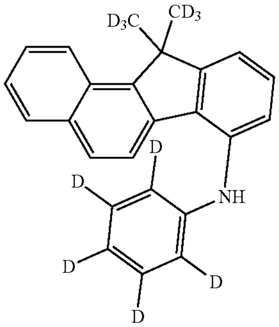
-continued
Sub 1-27
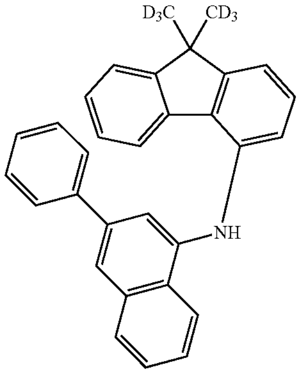
Sub 1-28
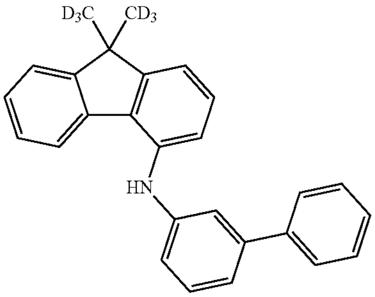
Sub 1-29
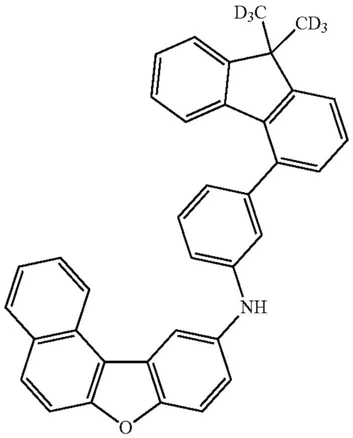
Sub 1-30
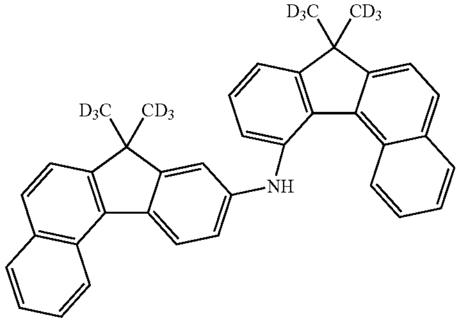

-continued
Sub 1-31
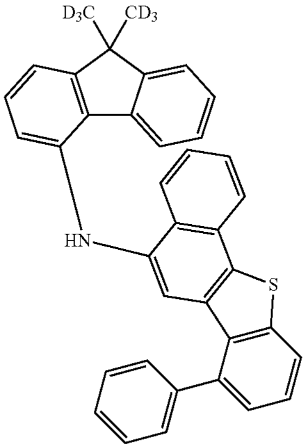
Sub 1-32
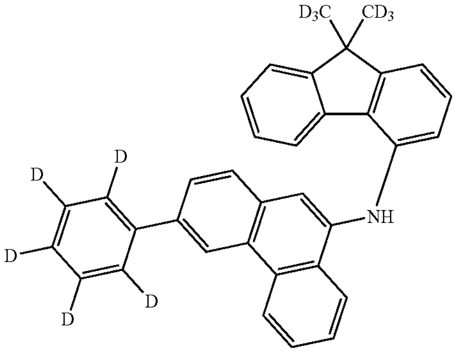
Sub 1-33
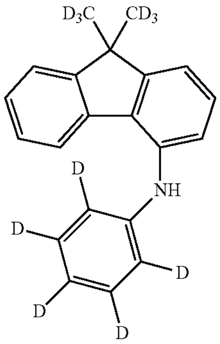
Sub 1-34
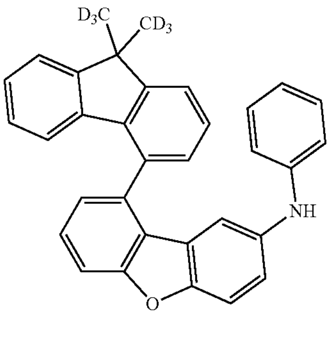
-continued
Sub 1-35
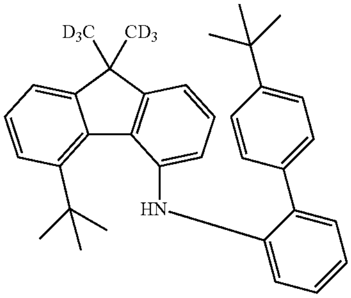
Sub 1-36
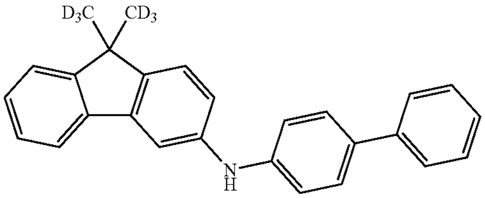
Sub 1-37
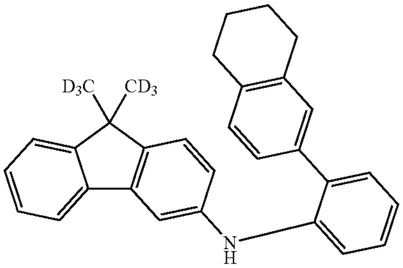
Sub 1-38
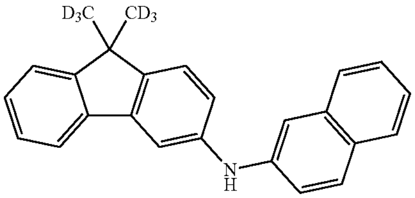
Sub 1-39
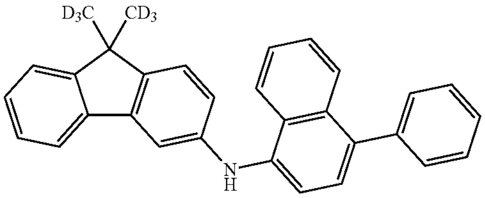
Sub 1-40
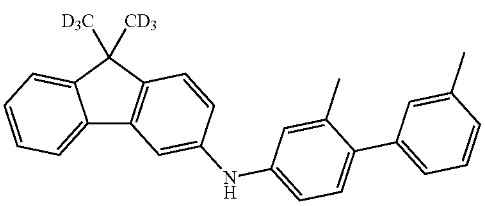

-continued
Sub 1-41
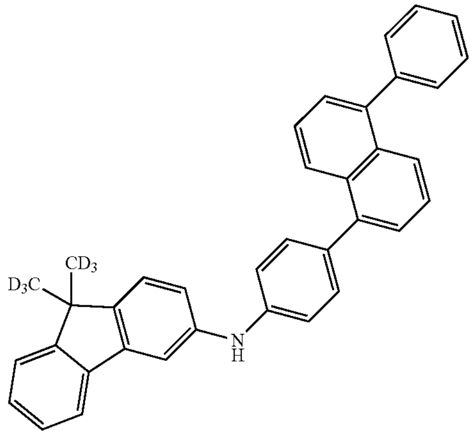
Sub 1-42
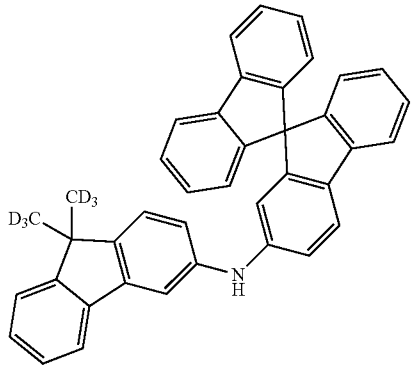
Sub 1-43
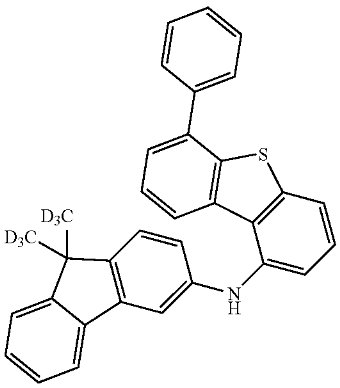
Sub 1-44
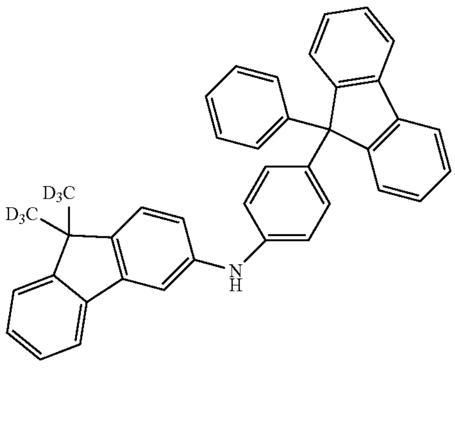
-continued
Sub 1-45
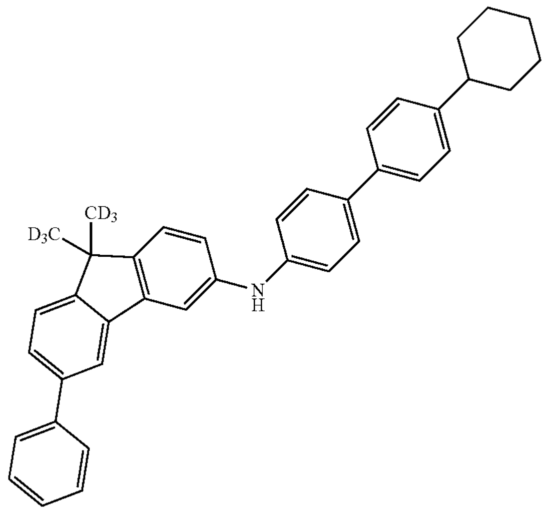
Sub 1-46
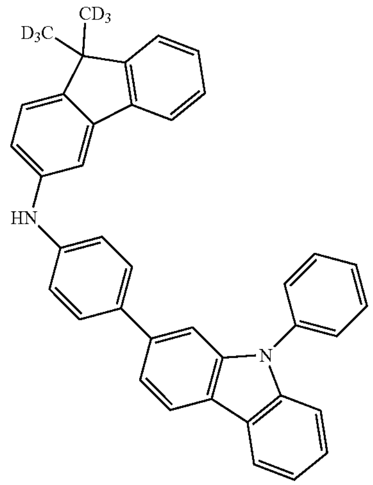
Sub 1-47
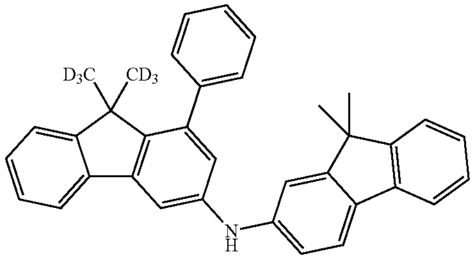
Sub 1-48
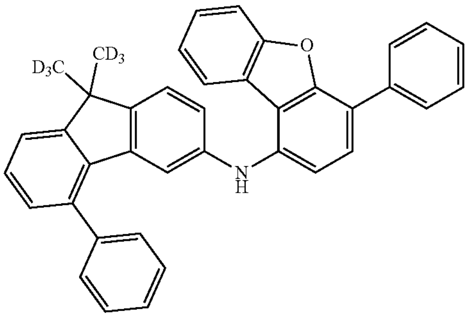

-continued
Sub 1-49
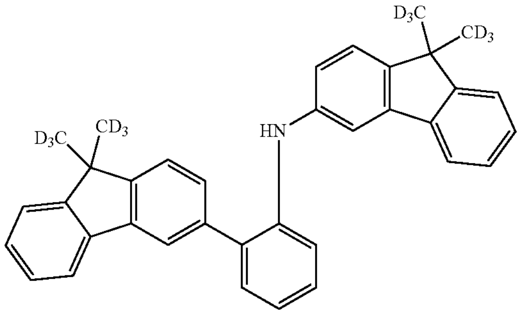
Sub 1-50
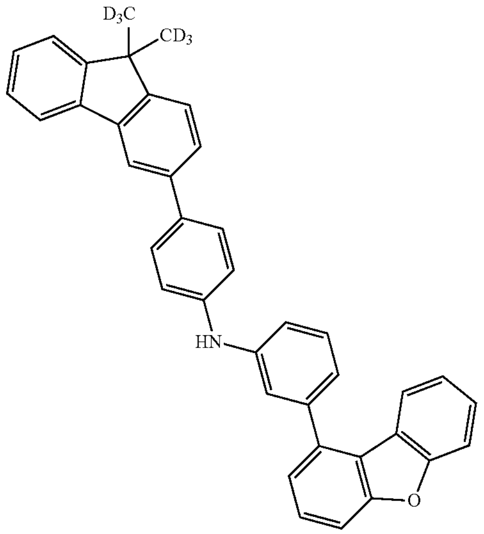
Sub 1-51
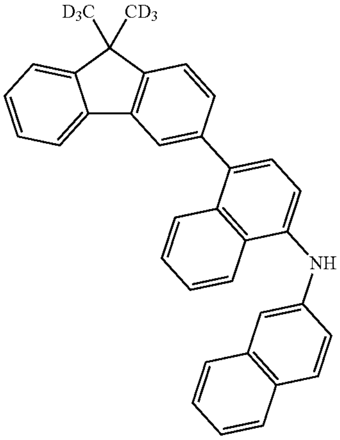
-continued
Sub 1-52
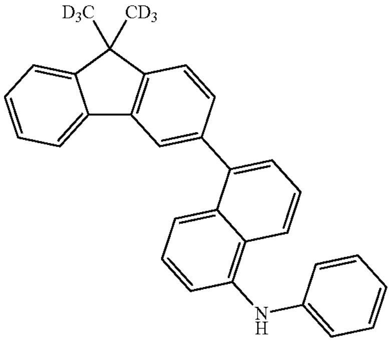
Sub 1-53
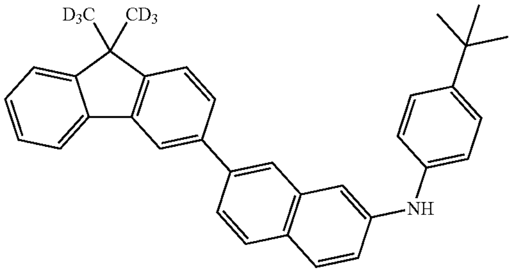
Sub 1-54
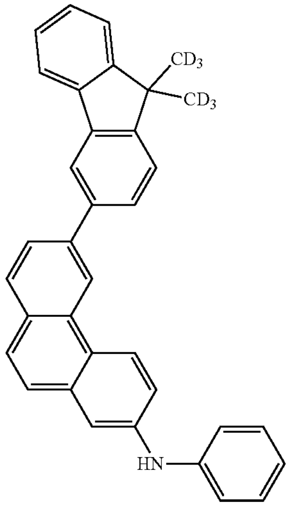
Sub 1-55
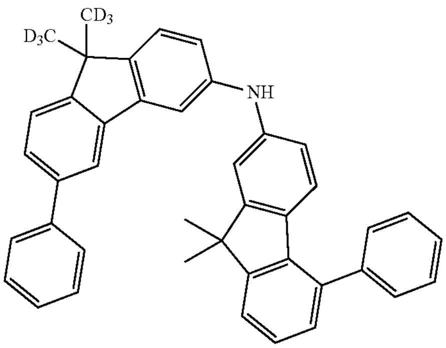

-continued
Sub 1-56
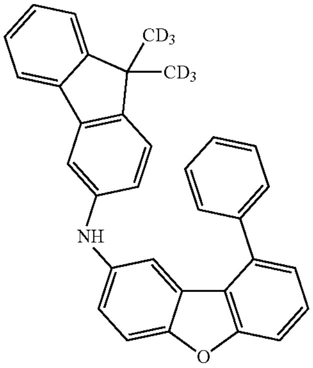
Sub 1-57
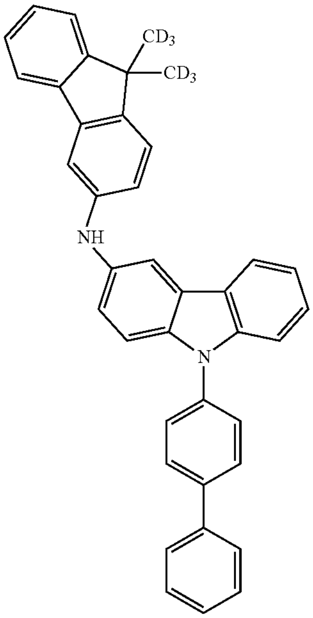
Sub 1-58
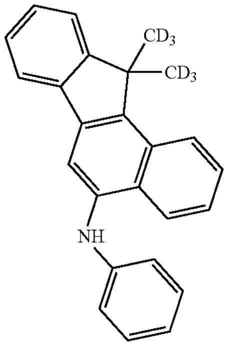
Sub 1-59
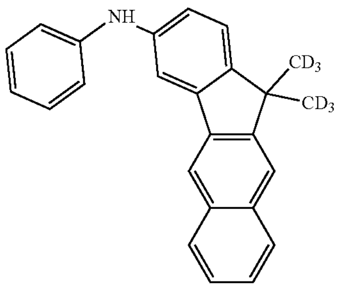
-continued
Sub 1-60
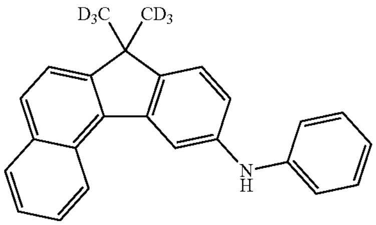
Sub 1-61
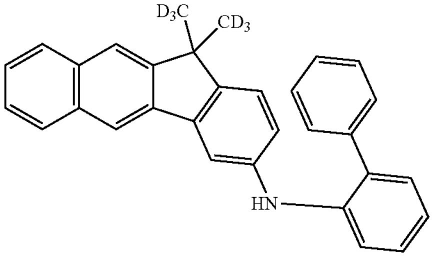
Sub 1-62
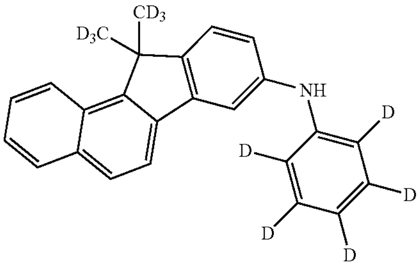
Sub 1-63
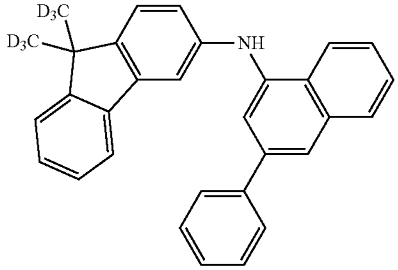
Sub 1-64
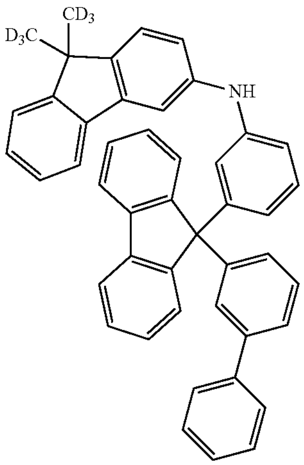

-continued
Sub 1-65
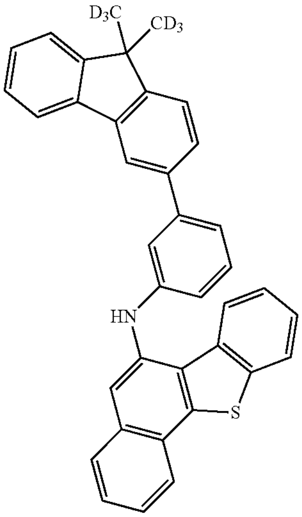
Sub 1-66
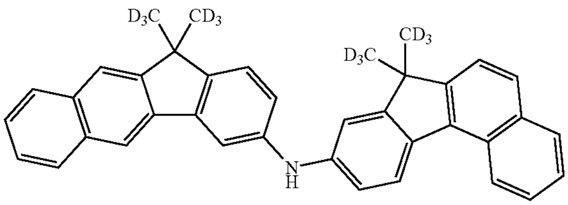
Sub 1-67
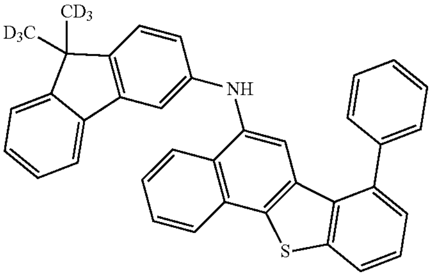
Sub 1-68
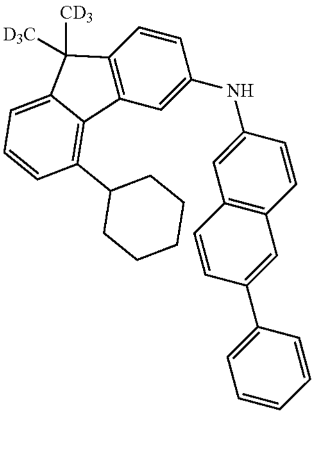
-continued
Sub 1-69
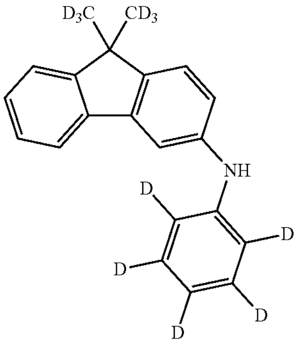
Sub 1-70
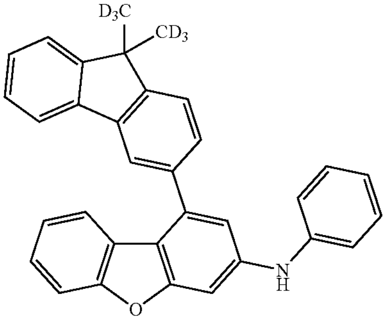
Sub 1-71
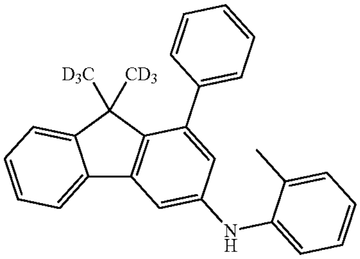
Sub 1-72
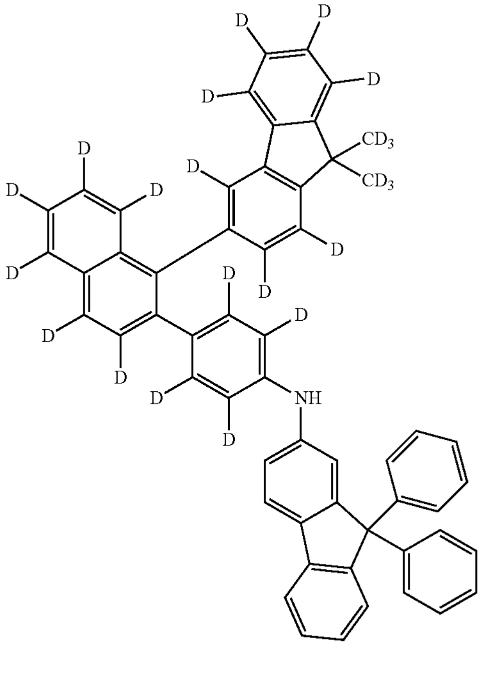

-continued
Sub 1-73
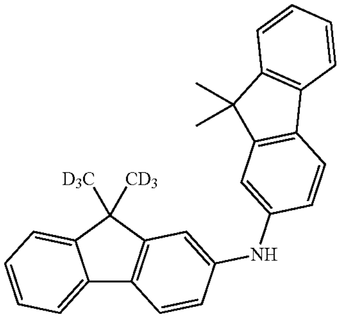
Sub 1-74
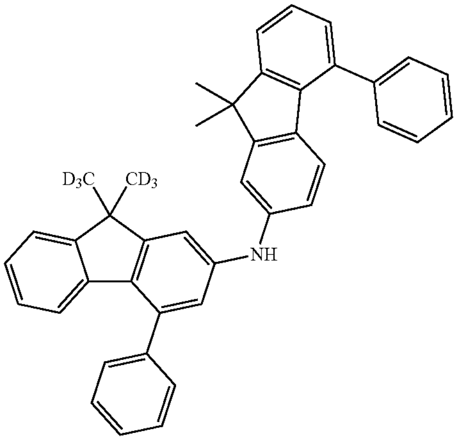
Sub 1-75
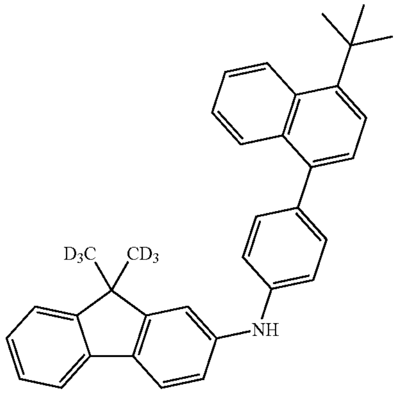
Sub 1-76
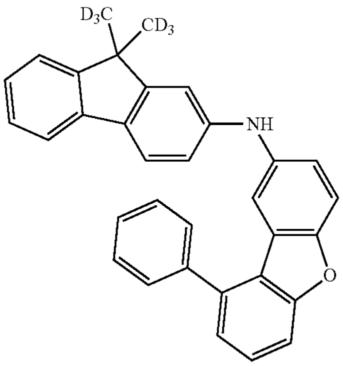
-continued
Sub 1-77
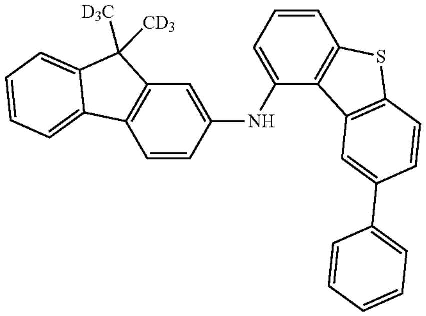
Sub 1-78
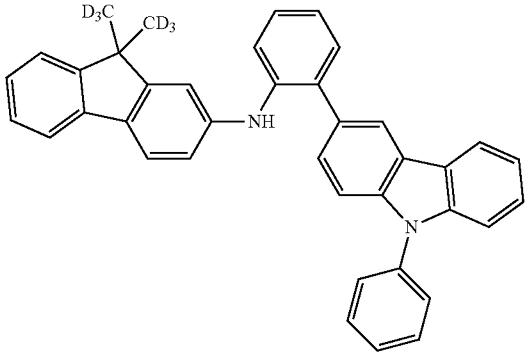
Sub 1-79
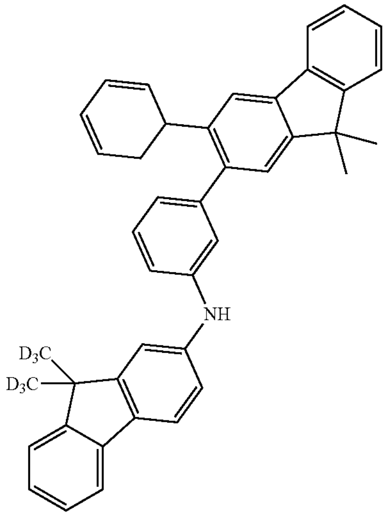
Sub 1-80
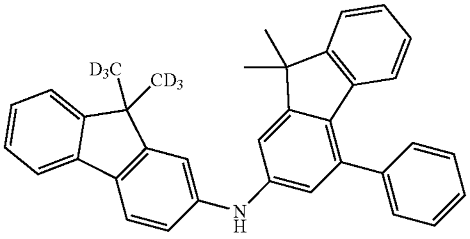

-continued
Sub 1-81
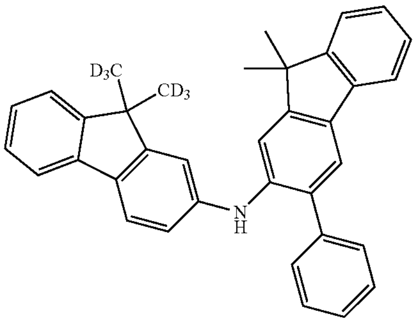
Sub 1-82
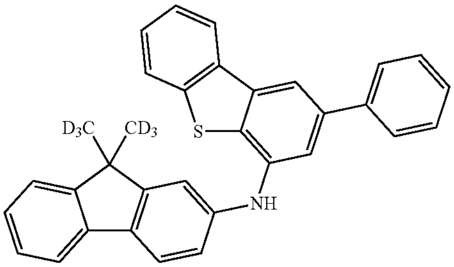
Sub 1-83
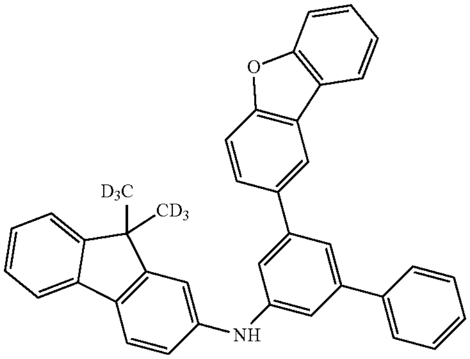
Sub 1-84
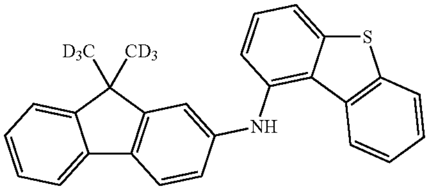
Sub 1-85
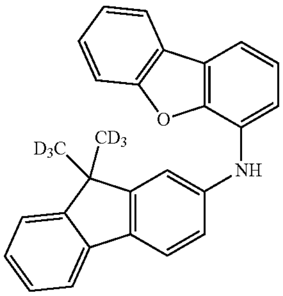
-continued
Sub 1-86
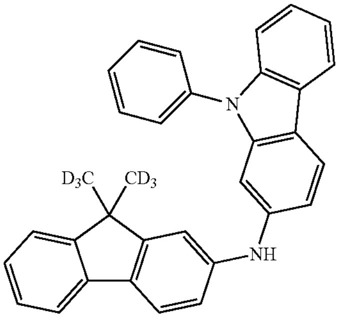
Sub 1-87
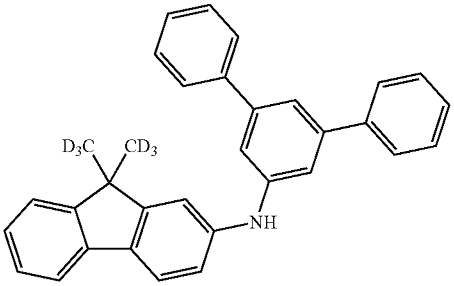
Sub 1-88
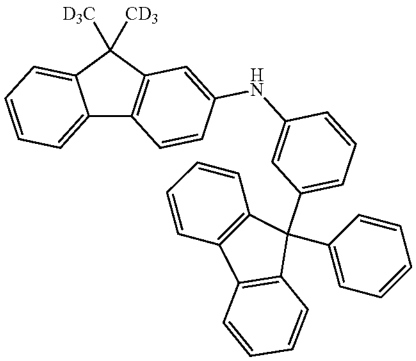
Sub 1-89
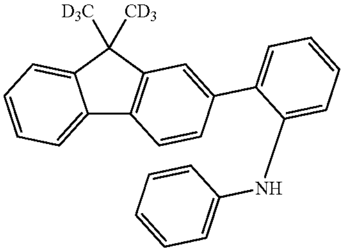
Sub 1-90
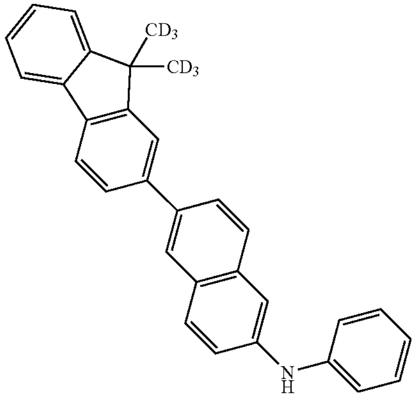

-continued
Sub 1-91
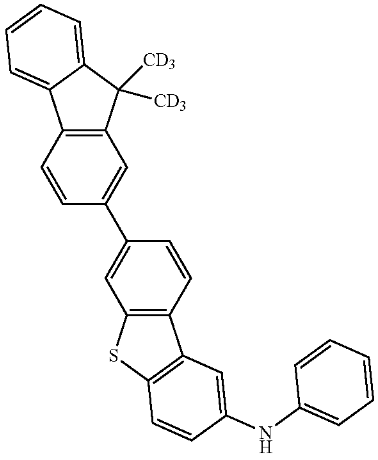
Sub 1-92
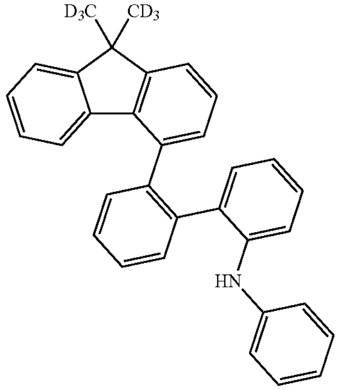
Sub 1-93
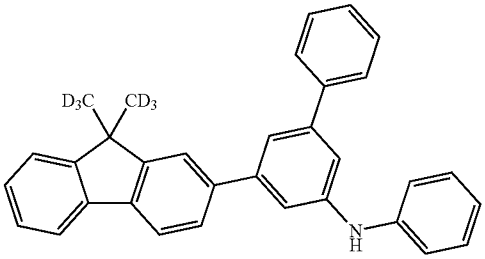
Sub 1-94
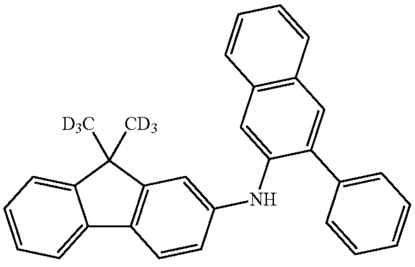
-continued
Sub 1-95
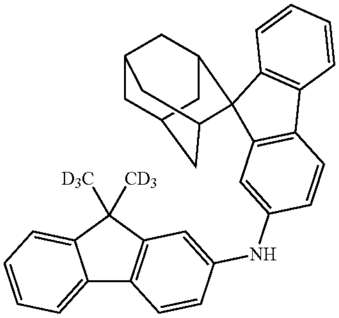
Sub 1-96
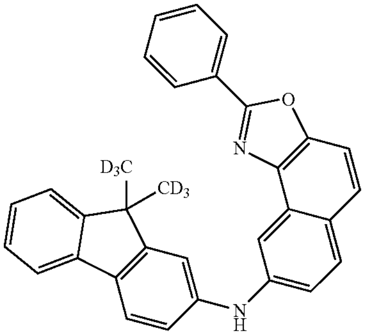
Sub 1-97
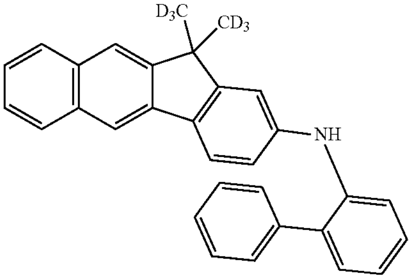
Sub 1-98
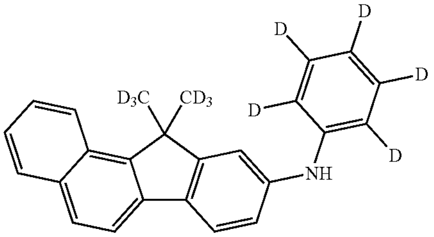
Sub 1-99
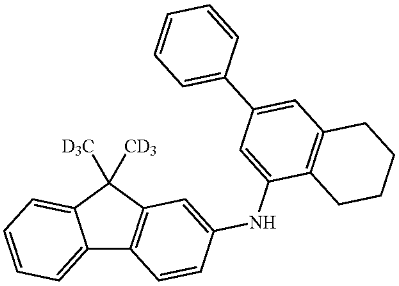

-continued
Sub 1-100
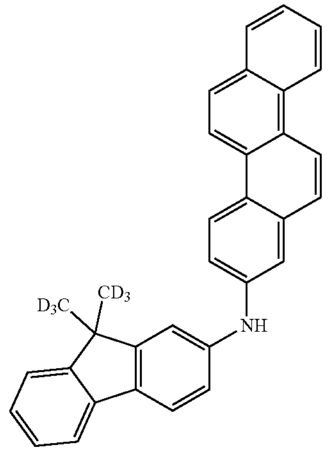
Sub 1-101
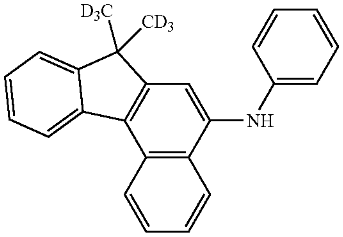
Sub 1-102
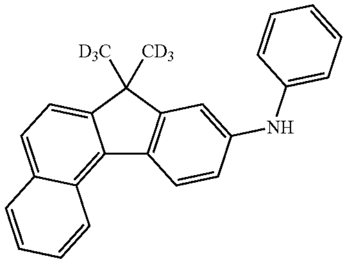
Sub 1-103
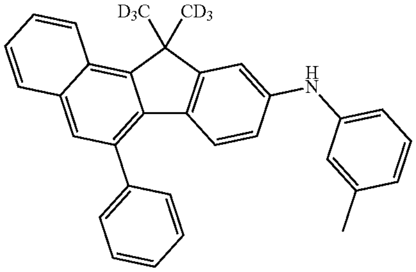
Sub 1-104
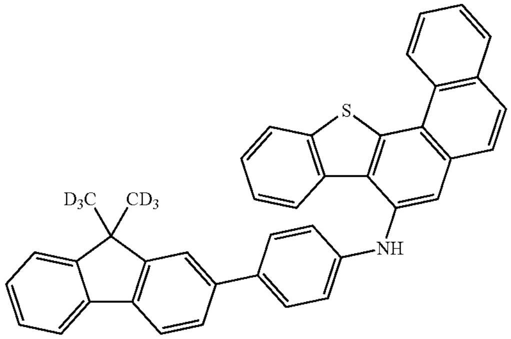
-continued
Sub 1-105
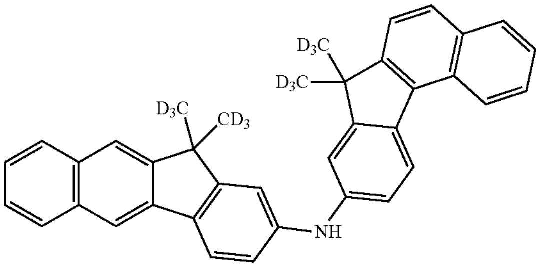
Sub 1-106
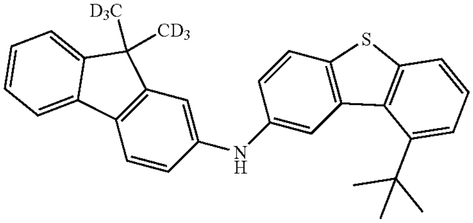
Sub 1-107
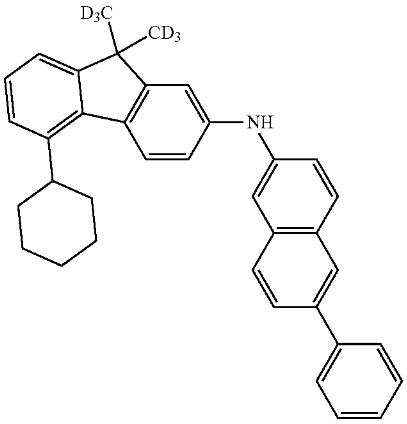
Sub 1-108
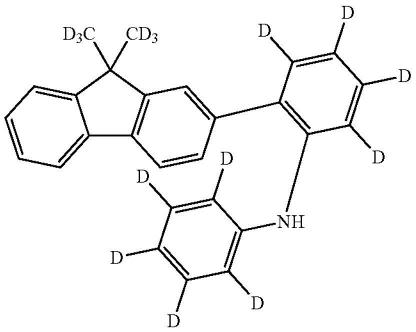

-continued
Sub 1-109
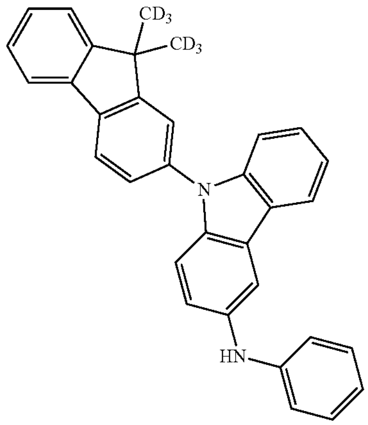
Sub 1-110
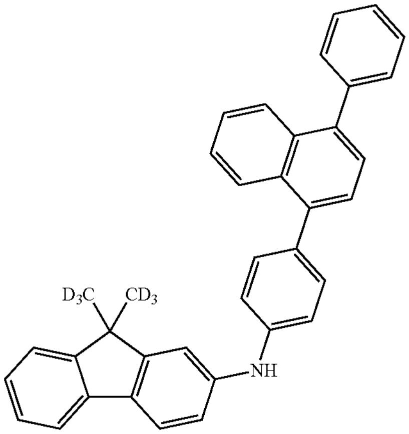
Sub 1-111
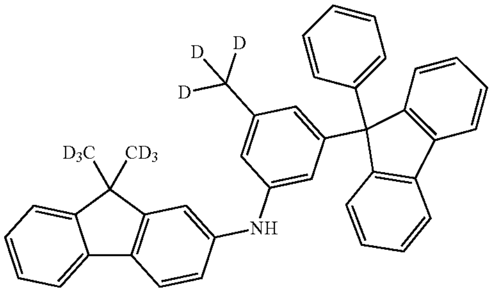
Sub 1-112
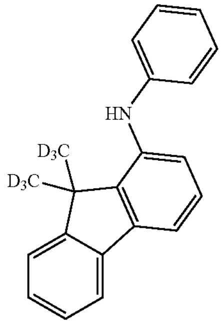
-continued
Sub 1-113
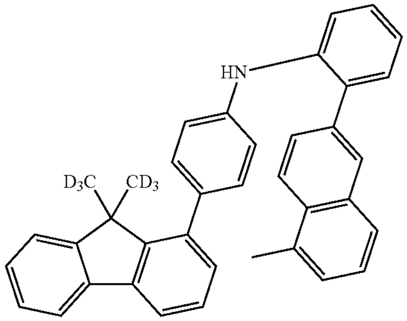
Sub 1-114
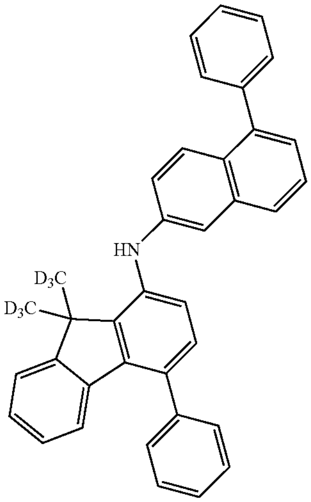
Sub 1-115
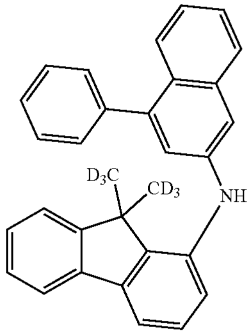
Sub 1-116
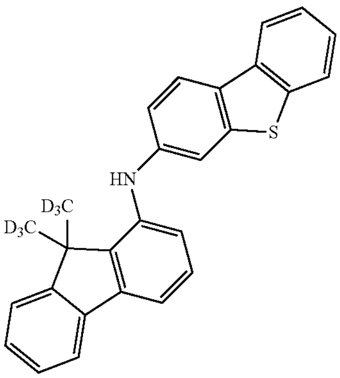

-continued
Sub 1-117
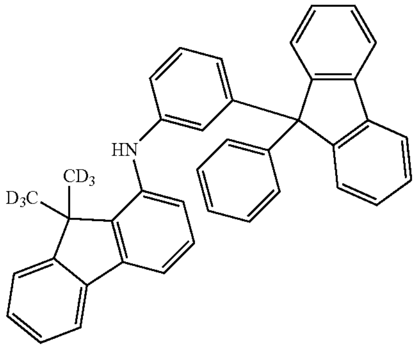
Sub 1-118
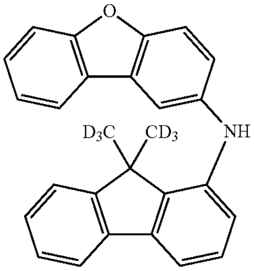
Sub 1-119
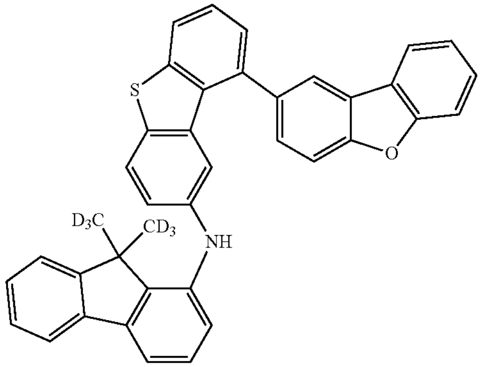
Sub 1-120
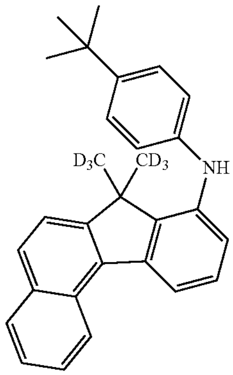
-continued
Sub 1-121
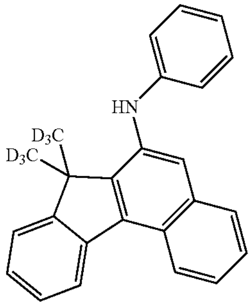
Sub 1-122
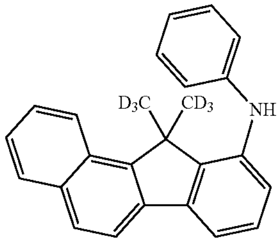
Sub 1-123
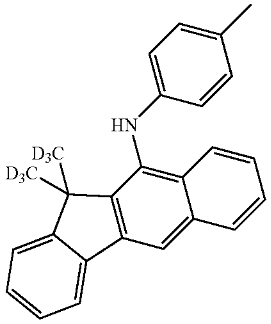
Sub 1-124
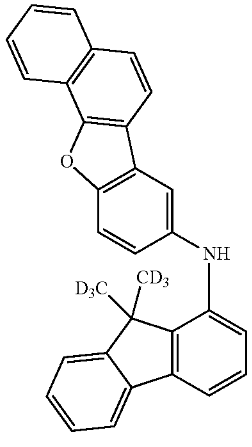

-continued
Sub 1-125
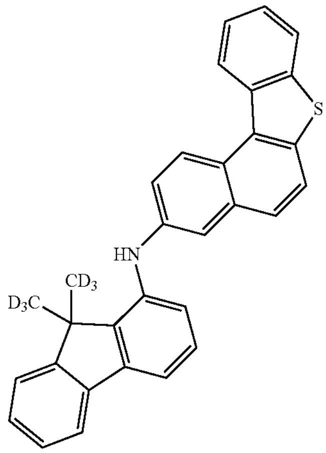
Sub 1-126
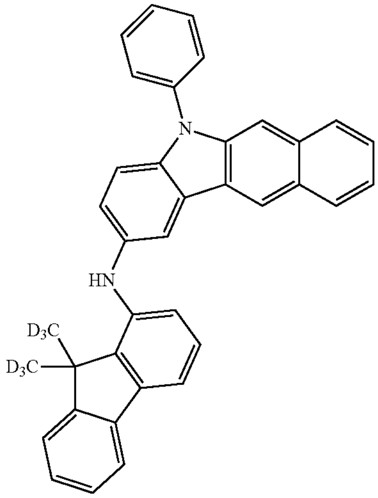
Sub 1-127
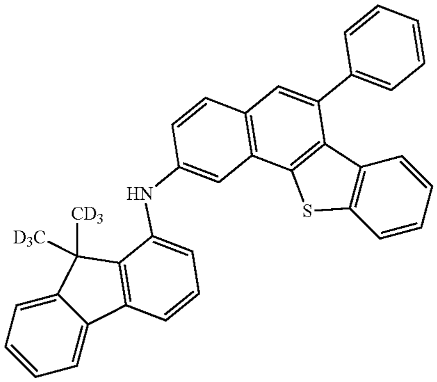
-continued
Sub 1-128
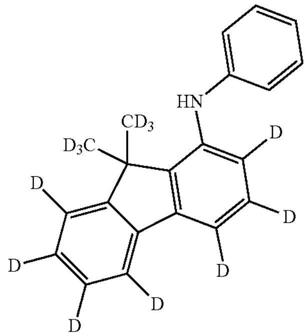
Sub 1-129
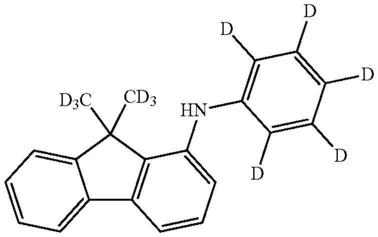
Sub 1-130
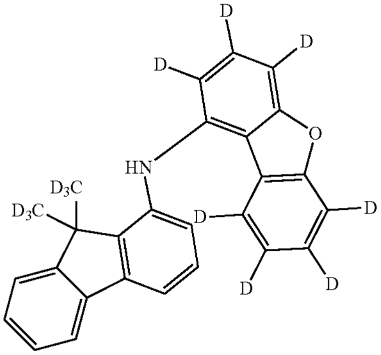
Sub 1-131
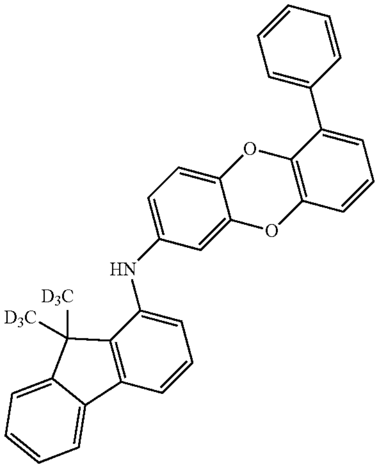

-continued
Sub 1-132
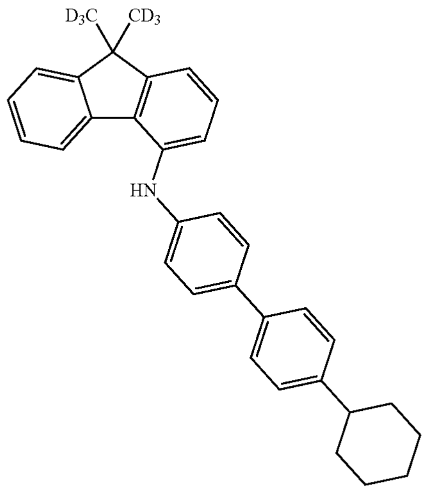
Sub 1-133
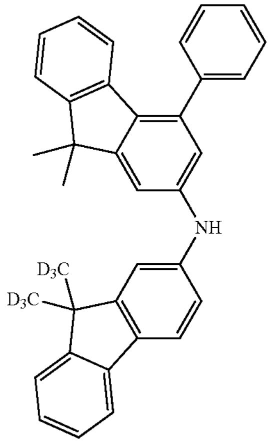
Sub 1-134
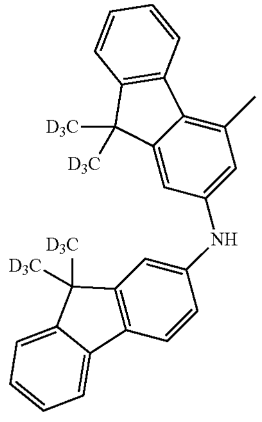
-continued
Sub 1-135
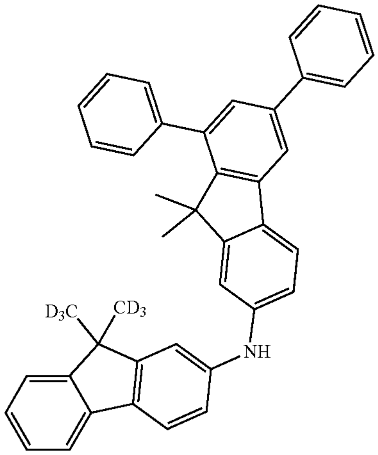
Sub 1-136
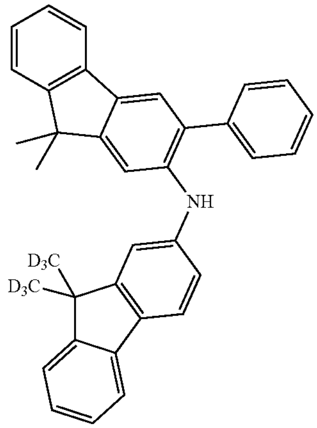
Sub 1-137
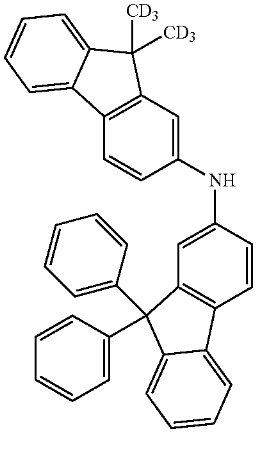

-continued
Sub 1-138
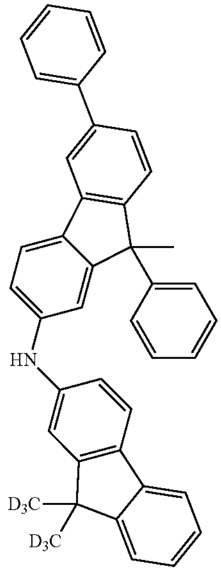
Sub 1-139
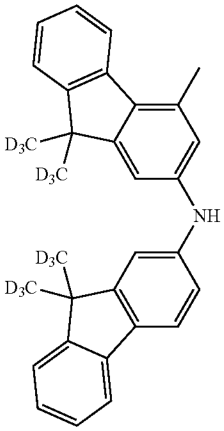
Sub 1-140
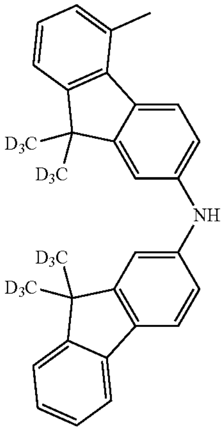
-continued
Sub 1-141
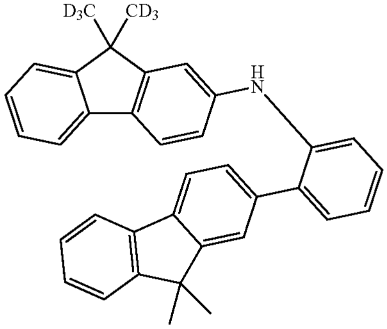
Sub 1-142
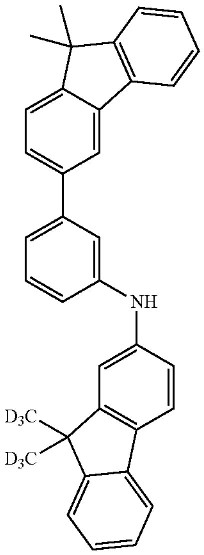
Sub 1-143
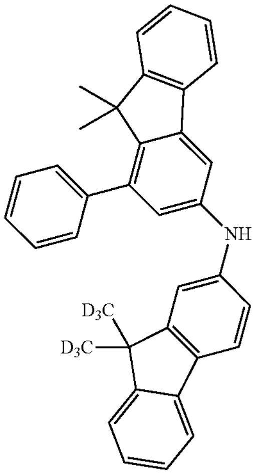

Sub 1-144
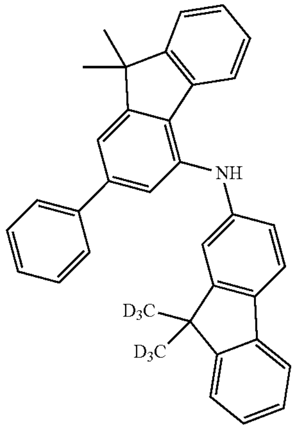
Sub 1-145
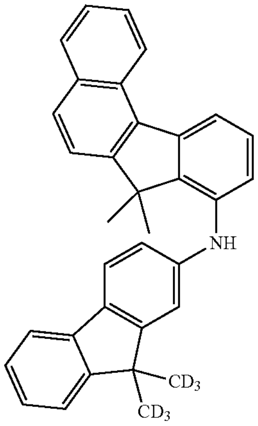
Sub 1-146
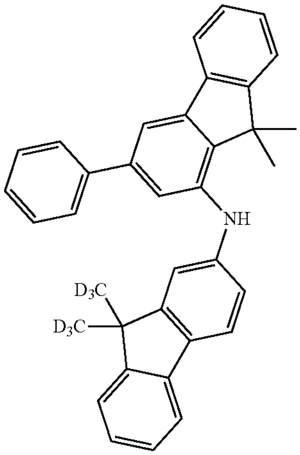
Sub 1-147
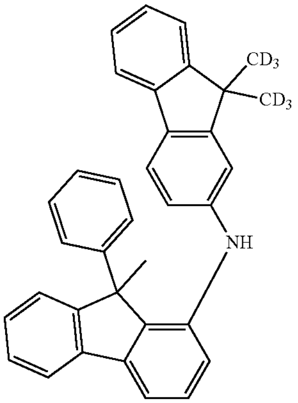
Sub 1-148
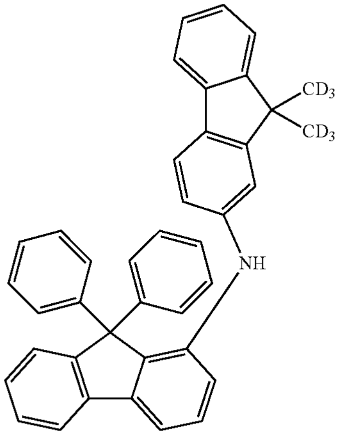
Sub 1-149
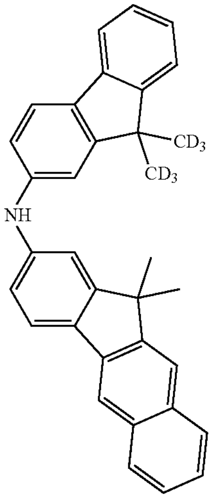

-continued

Sub 1-150

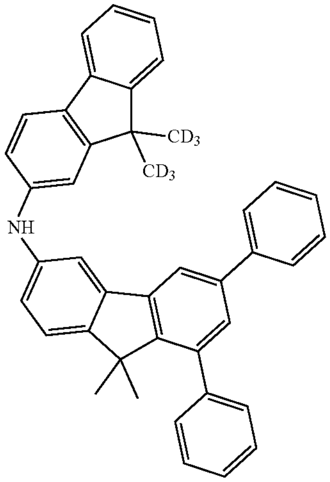

Sub 1-151

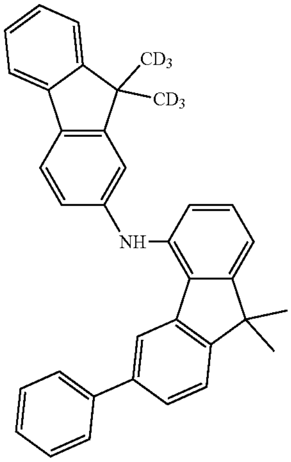

Sub 1-152

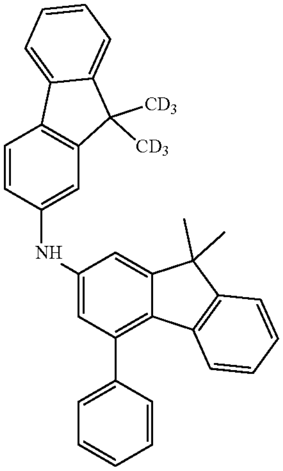

TABLE 1

| Compound | FD-MS |
|---|---|
| Sub 1-1 | m/z = 291.19($C_{21}H_{13}D_6N$ = 291.43) |
| Sub 1-2 | m/z = 367.22($C_{27}H_{17}D_6N$ = 367.52) |
| Sub 1-3 | m/z = 391.22($C_{29}H_{17}D_6N$ = 391.55) |
| Sub 1-4 | m/z = 417.24($C_{31}H_{19}D_6N$ = 417.58) |

TABLE 1-continued

| Compound | FD-MS |
|---|---|
| Sub 1-5 | m/z = 417.24($C_{31}H_{19}D_6N$ = 417.58) |
| Sub 1-6 | m/z = 493.27($C_{37}H_{23}D_6N$ = 493.68) |
| Sub 1-7 | m/z = 397.18($C_{27}H_{15}D_6NS$ = 397.57) |
| Sub 1-8 | m/z = 457.23($C_{33}H_{19}D_6NO$ = 457.61) |
| Sub 1-9 | m/z = 423.28($C_{31}H_{25}D_6N$ = 423.63) |
| Sub 1-10 | m/z = 456.25($C_{33}H_{20}D_6N_2$ = 456.62) |
| Sub 1-11 | m/z = 483.28($C_{36}H_{25}D_6N$ = 483.69) |
| Sub 1-12 | m/z = 549.24($C_{39}H_{23}D_6NS$ = 549.76) |
| Sub 1-13 | m/z = 489.32($C_{36}H_{19}D_{12}N$ = 489.72) |
| Sub 1-14 | m/z = 533.26($C_{39}H_{23}D_6NO$ = 533.7) |
| Sub 1-15 | m/z = 493.27($C_{37}H_{23}D_6N$ = 493.68) |
| Sub 1-16 | m/z = 417.24($C_{31}H_{19}D_6N$ = 417.58) |
| Sub 1-17 | m/z = 473.30($C_{35}H_{27}D_6N$ = 473.69) |
| Sub 1-18 | m/z = 467.25($C_{35}H_{21}D_6N$ = 467.64) |
| Sub 1-19 | m/z = 559.31($C_{42}H_{29}D_6N$ = 559.79) |
| Sub 1-20 | m/z = 473.21($C_{33}H_{19}D_6NS$ = 473.67) |
| Sub 1-21 | m/z = 456.25($C_{33}H_{20}D_6N_2$ = 456.62) |
| Sub 1-22 | m/z = 341.21($C_{25}H_{15}D_6N$ = 341.49) |
| Sub 1-23 | m/z = 341.21($C_{25}H_{15}D_6N$ = 341.49) |
| Sub 1-24 | m/z = 341.21($C_{25}H_{15}D_6N$ = 341.49) |
| Sub 1-25 | m/z = 417.24($C_{31}H_{19}D_6N$ = 417.58) |
| Sub 1-26 | m/z = 346.24($C_{25}H_{10}D_{11}N$ = 346.52) |
| Sub 1-27 | m/z = 417.24($C_{31}H_{19}D_6N$ = 417.58) |
| Sub 1-28 | m/z = 367.22($C_{27}H_{17}D_6N$ = 367.52) |
| Sub 1-29 | m/z = 507.25($C_{37}H_{21}D_6NO$ = 507.67) |
| Sub 1-30 | m/z = 513.32($C_{38}H_{19}D_{12}N$ = 513.75) |
| Sub 1-31 | m/z = 523.22($C_{37}H_{21}D_6NS$ = 523.73) |
| Sub 1-32 | m/z = 472.28($C_{35}H_{16}D_{11}N$ = 472.68) |
| Sub 1-33 | m/z = 296.22($C_{21}H_8D_{11}N$ = 296.46) |
| Sub 1-34 | m/z = 457.23($C_{33}H_{19}D_6NO$ = 457.61) |
| Sub 1-35 | m/z = 479.35($C_{35}H_{33}D_6N$ = 479.74) |
| Sub 1-36 | m/z = 367.22($C_{27}H_{17}D_6N$ = 367.52) |
| Sub 1-37 | m/z = 421.27($C_{31}H_{23}D_6N$ = 421.62) |
| Sub 1-38 | m/z = 341.21($C_{25}H_{15}D_6N$ = 341.49) |
| Sub 1-39 | m/z = 417.24($C_{31}H_{19}D_6N$ = 417.58) |
| Sub 1-40 | m/z = 395.25($C_{29}H_{21}D_6N$ = 395.58) |
| Sub 1-41 | m/z = 493.27($C_{37}H_{23}D_6N$ = 493.68) |
| Sub 1-42 | m/z = 529.27($C_{40}H_{23}D_6N$ = 529.72) |
| Sub 1-43 | m/z = 473.21($C_{33}H_{19}D_6NS$ = 473.67) |
| Sub 1-44 | m/z = 531.28($C_{40}H_{25}D_6N$ = 531.73) |
| Sub 1-45 | m/z = 525.33($C_{39}H_{31}D_6N$ = 525.77) |
| Sub 1-46 | m/z = 532.28($C_{39}H_{24}D_6N_2$ = 532.72) |
| Sub 1-47 | m/z = 483.28($C_{36}H_{25}D_6N$ = 483.69) |
| Sub 1-48 | m/z = 533.26($C_{39}H_{23}D_6NO$ = 533.70) |
| Sub 1-49 | m/z = 489.32($C_{36}H_{19}D_{12}N$ = 489.72) |
| Sub 1-50 | m/z = 533.26($C_{39}H_{23}D_6NO$ = 533.70) |
| Sub 1-51 | m/z = 467.25($C_{35}H_{21}D_6N$ = 467.64) |
| Sub 1-52 | m/z = 417.24($C_{31}H_{19}D_6N$ = 417.58) |
| Sub 1-53 | m/z = 473.30($C_{35}H_{27}D_6N$ = 473.69) |
| Sub 1-54 | m/z = 467.25($C_{35}H_{21}D_6N$ = 467.64) |
| Sub 1-55 | m/z = 559.31($C_{42}H_{29}D_6N$ = 559.79) |
| Sub 1-56 | m/z = 457.23($C_{33}H_{19}D_6NO$ = 457.61) |
| Sub 1-57 | m/z = 532.28($C_{39}H_{24}D_6N_2$ = 532.72) |
| Sub 1-58 | m/z = 341.21($C_{25}H_{15}D_6N$ = 341.49) |
| Sub 1-59 | m/z = 341.21($C_{25}H_{15}D_6N$ = 341.49) |
| Sub 1-60 | m/z = 341.21($C_{25}H_{15}D_6N$ = 341.49) |
| Sub 1-61 | m/z = 417.24($C_{31}H_{19}D_6N$ = 417.58) |
| Sub 1-62 | m/z = 346.24($C_{25}H_{10}D_{11}N$ = 346.52) |
| Sub 1-63 | m/z = 417.24($C_{31}H_{19}D_6N$ = 417.58) |
| Sub 1-64 | m/z = 607.31($C_{46}H_{29}D_6N$ = 607.83) |
| Sub 1-65 | m/z = 523.22($C_{37}H_{21}D_6NS$ = 523.73) |
| Sub 1-66 | m/z = 513.32($C_{38}H_{19}D_{12}N$ = 513.75) |
| Sub 1-67 | m/z = 523.22($C_{37}H_{21}D_6NS$ = 523.73) |
| Sub 1-68 | m/z = 499.31($C_{37}H_{29}D_6N$ = 499.73) |
| Sub 1-69 | m/z = 296.22($C_{21}H_8D_{11}N$ = 296.46) |
| Sub 1-70 | m/z = 457.23($C_{33}H_{19}D_6NO$ = 457.61) |
| Sub 1-71 | m/z = 381.24($C_{28}H_{19}D_6N$ = 381.55) |
| Sub 1-72 | m/z = 750.47($C_{56}H_{18}D_{23}N$ = 751.09) |
| Sub 1-73 | m/z = 407.25($C_{30}H_{21}D_6N$ = 407.59) |
| Sub 1-74 | m/z = 559.31($C_{42}H_{29}D_6N$ = 559.79) |
| Sub 1-75 | m/z = 473.3($C_{35}H_{27}D_6N$ = 473.69) |
| Sub 1-76 | m/z = 457.23($C_{33}H_{19}D_6NO$ = 457.61) |
| Sub 1-77 | m/z = 473.21($C_{33}H_{19}D_6NS$ = 473.67) |
| Sub 1-78 | m/z = 532.28($C_{39}H_{24}D_6N_2$ = 532.72) |
| Sub 1-79 | m/z = 559.31($C_{42}H_{29}D_6N$ = 559.79) |
| Sub 1-80 | m/z = 483.28($C_{36}H_{25}D_6N$ = 483.69) |
| Sub 1-81 | m/z = 483.28($C_{36}H_{25}D_6N$ = 483.69) |
| Sub 1-82 | m/z = 473.21($C_{33}H_{19}D_6NS$ = 473.67) |

TABLE 1-continued

| Compound | FD-MS |
|---|---|
| Sub 1-83 | m/z = 533.26($C_{39}H_{23}D_6NO$ = 533.70) |
| Sub 1-84 | m/z = 397.18($C_{27}H_{15}D_6NS$ = 397.57) |
| Sub 1-85 | m/z = 381.2($C_{27}H_{15}D_6NO$ = 381.51) |
| Sub 1-86 | m/z = 456.25($C_{33}H_{20}D_6N_2$ = 456.62) |
| Sub 1-87 | m/z = 443.25($C_{33}H_{21}D_6N$ = 443.62) |
| Sub 1-88 | m/z = 531.28($C_{40}H_{25}D_6N$ = 531.73) |
| Sub 1-89 | m/z = 367.22($C_{27}H_{17}D_6N$ = 367.52) |
| Sub 1-90 | m/z = 417.24($C_{31}H_{19}D_6N$ = 417.58) |
| Sub 1-91 | m/z = 473.21($C_{33}H_{19}D_6NS$ = 473.67) |
| Sub 1-92 | m/z = 443.25($C_{33}H_{21}D_6N$ = 443.62) |
| Sub 1-93 | m/z = 443.25($C_{33}H_{21}D_6N$ = 443.62) |
| Sub 1-94 | m/z = 417.24($C_{31}H_{19}D_6N$ = 417.58) |
| Sub 1-95 | m/z = 499.31($C_{37}H_{29}D_6N$ = 499.73) |
| Sub 1-96 | m/z = 458.23($C_{32}H_{18}D_6N_2O$ = 458.59) |
| Sub 1-97 | m/z = 417.24($C_{31}H_{19}D_6N$ = 417.58) |
| Sub 1-98 | m/z = 346.24($C_{25}H_{10}D_{11}N$ = 346.52) |
| Sub 1-99 | m/z = 421.27($C_{31}H_{23}D_6N$ = 421.62) |
| Sub 1-100 | m/z = 441.24($C_{33}H_{19}D_6N$ = 441.61) |
| Sub 1-101 | m/z = 341.21($C_{25}H_{15}D_6N$ = 341.49) |
| Sub 1-102 | m/z = 341.21($C_{25}H_{15}D_6N$ = 341.49) |
| Sub 1-103 | m/z = 431.25($C_{32}H_{21}D_6N$ = 431.61) |
| Sub 1-104 | m/z = 573.24($C_{41}H_{23}D_6NS$ = 573.79) |
| Sub 1-105 | m/z = 513.32($C_{38}H_{19}D_{12}N$ = 513.75) |
| Sub 1-106 | m/z = 453.24($C_{31}H_{23}D_6NS$ = 453.68) |
| Sub 1-107 | m/z = 499.31($C_{37}H_{29}D_6N$ = 499.73) |
| Sub 1-108 | m/z = 376.28($C_{27}H_8D_{15}N$ = 376.58) |
| Sub 1-109 | m/z = 456.25($C_{33}H_{20}D_6N_2$ = 456.62) |
| Sub 1-110 | m/z = 493.27($C_{37}H_{23}D_6N$ = 493.68) |
| Sub 1-111 | m/z = 548.32($C_{41}H_{24}D_9N$ = 548.78) |
| Sub 1-112 | m/z = 291.19($C_{21}H_{13}D_6N$ = 291.43) |
| Sub 1-113 | m/z = 507.28($C_{38}H_{25}D_6N$ = 507.71) |
| Sub 1-114 | m/z = 493.27($C_{37}H_{23}D_6N$ = 493.68) |
| Sub 1-115 | m/z = 417.24($C_{31}H_{19}D_6N$ = 417.58) |
| Sub 1-116 | m/z = 397.18($C_{27}H_{15}D_6NS$ = 397.57) |
| Sub 1-117 | m/z = 531.28($C_{40}H_{25}D_6N$ = 531.73) |
| Sub 1-118 | m/z = 381.20($C_{27}H_{15}D_6NO$ = 381.51) |
| Sub 1-119 | m/z = 563.22($C_{39}H_{21}D_6NOS$ = 563.75) |
| Sub 1-120 | m/z = 397.27($C_{29}H_{23}D_6N$ = 397.59) |
| Sub 1-121 | m/z = 341.21($C_{25}H_{15}D_6N$ = 341.49) |
| Sub 1-122 | m/z = 341.21($C_{25}H_{15}D_6N$ = 341.49) |
| Sub 1-123 | m/z = 355.22($C_{26}H_{17}D_6N$ = 355.51) |
| Sub 1-124 | m/z = 431.22($C_{31}H_{17}D_6NO$ = 431.57) |
| Sub 1-125 | m/z = 447.19($C_{31}H_{17}D_6NS$ = 447.63) |
| Sub 1-126 | m/z = 506.26($C_{37}H_{22}D_6N_2$ = 506.68) |
| Sub 1-127 | m/z = 523.22($C_{37}H_{21}D_6NS$ = 523.73) |
| Sub 1-128 | m/z = 298.23($C_{21}H_6D_{13}N$ = 298.47) |
| Sub 1-129 | m/z = 296.22($C_{21}H_8D_{11}N$ = 296.46) |
| Sub 1-130 | m/z = 388.24($C_{27}H_8D_{13}NO$ = 388.55) |
| Sub 1-131 | m/z = 473.23($C_{33}H_{19}D_6NO_2$ = 473.6) |
| Sub 1-132 | m/z = 449.3($C_{33}H_{27}D_6N$ = 449.67) |
| Sub 1-133 | m/z = 483.28($C_{36}H_{25}D_6N$ = 483.69) |
| Sub 1-134 | m/z = 421.27($C_{31}H_{23}D_6N$ = 421.62) |
| Sub 1-135 | m/z = 559.31($C_{42}H_{29}D_6N$ = 559.79) |
| Sub 1-136 | m/z = 483.28($C_{36}H_{25}D_6N$ = 483.69) |
| Sub 1-137 | m/z = 531.28($C_{40}H_{25}D_6N$ = 531.73) |
| Sub 1-138 | m/z = 545.3($C_{41}H_{27}D_6N$ = 545.76) |
| Sub 1-139 | m/z = 427.31($C_{31}H_{17}D_{12}N$ = 427.65) |
| Sub 1-140 | m/z = 427.31($C_{31}H_{17}D_{12}N$ = 427.65) |
| Sub 1-141 | m/z = 483.28($C_{36}H_{25}D_6N$ = 483.69) |
| Sub 1-142 | m/z = 483.28($C_{36}H_{25}D_6N$ = 483.69) |
| Sub 1-143 | m/z = 483.28($C_{36}H_{25}D_6N$ = 483.69) |
| Sub 1-144 | m/z = 483.28($C_{36}H_{25}D_6N$ = 483.69) |
| Sub 1-145 | m/z = 457.27($C_{34}H_{23}D_6N$ = 457.65) |
| Sub 1-146 | m/z = 483.28($C_{36}H_{25}D_6N$ = 483.69) |
| Sub 1-147 | m/z = 469.27($C_{35}H_{23}D_6N$ = 469.66) |
| Sub 1-148 | m/z = 531.28($C_{40}H_{25}D_6N$ = 531.73) |
| Sub 1-149 | m/z = 457.27($C_{34}H_{23}D_6N$ = 457.65) |
| Sub 1-150 | m/z = 559.31($C_{42}H_{29}D_6N$ = 559.79) |
| Sub 1-151 | m/z = 483.28($C_{36}H_{25}D_6N$ = 483.69) |
| Sub 1-152 | m/z = 483.28($C_{36}H_{25}D_6N$ = 483.69) |

Sub 2 of the reaction scheme 1 may be, but is not limited to, the compounds below, and the FD-MS (Field Desorption-Mass Spectrometry) values of compounds belonging to Sub 2 are as shown in Table 2.

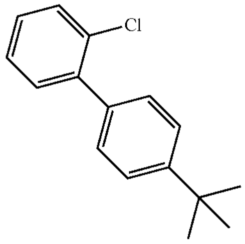

Sub 2-1

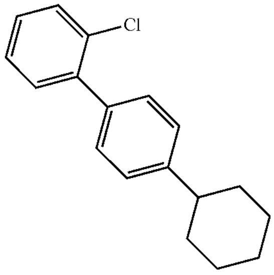

Sub 2-2

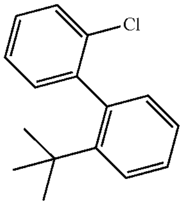

Sub 2-3

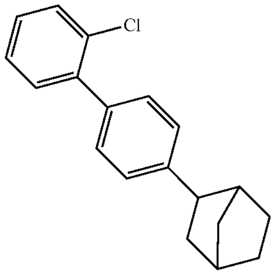

Sub 2-4

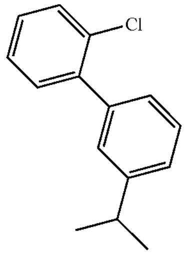

Sub 2-5

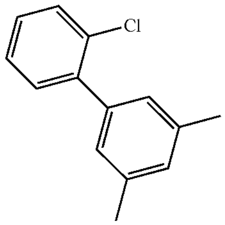

Sub 2-6

-continued
Sub 2-7
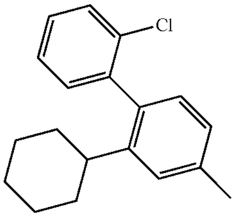
Sub 2-8
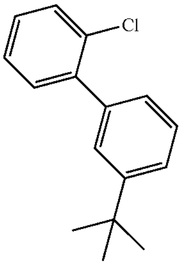
Sub 2-9
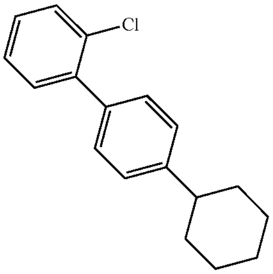
Sub 2-10
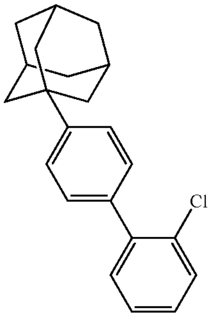
Sub 2-11
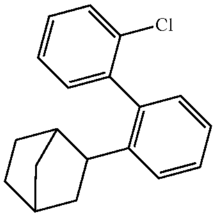
-continued
Sub 2-12
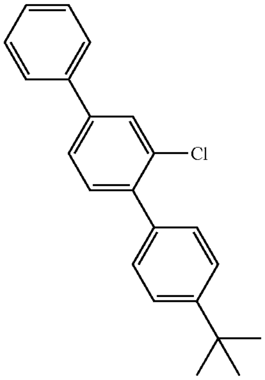
Sub 2-13
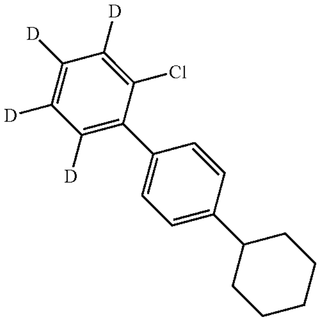
Sub 2-14
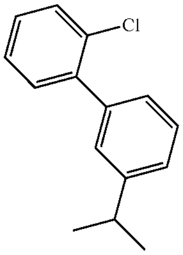
Sub 2-15
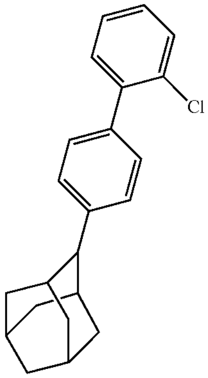
Sub 2-16
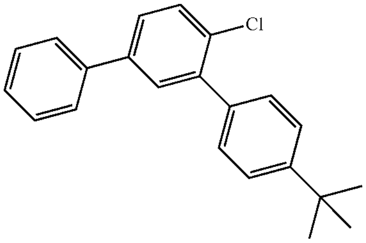

-continued
Sub 2-17
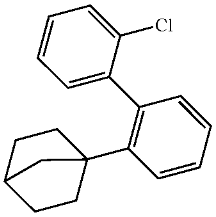
Sub 2-18
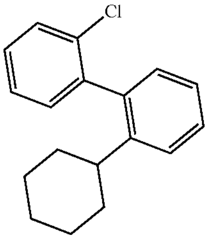
Sub 2-19
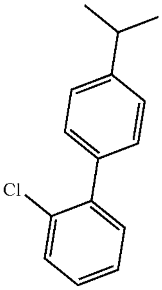
Sub 2-20
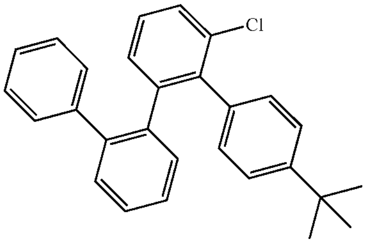
Sub 2-21
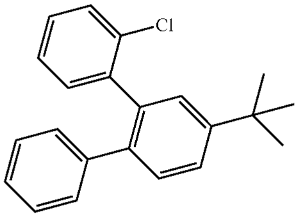
Sub 2-22
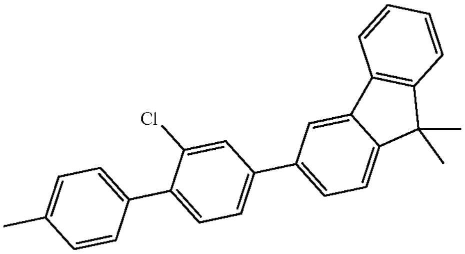
-continued
Sub 2-23
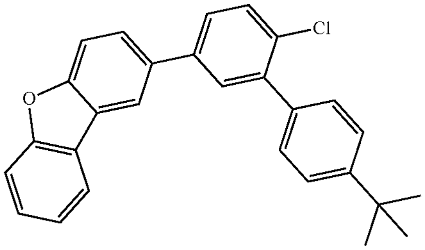
Sub 2-24
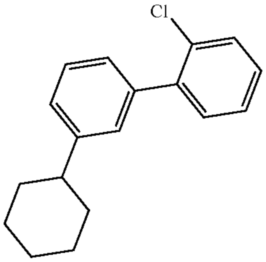
Sub 2-25
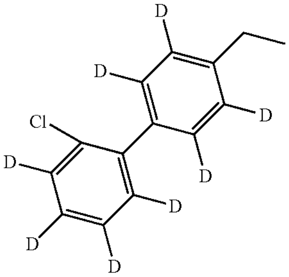
Sub 2-26
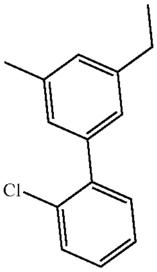
Sub 2-27
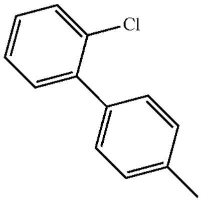
Sub 2-28
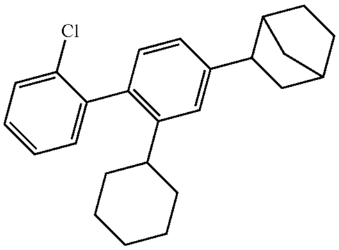

-continued
Sub 2-29
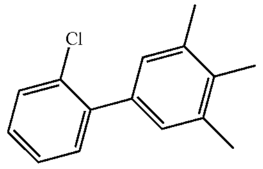
Sub 2-30
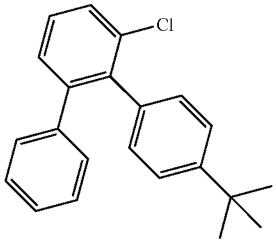
Sub 2-31
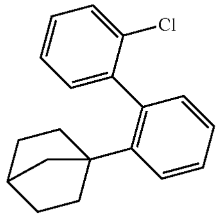
Sub 2-32
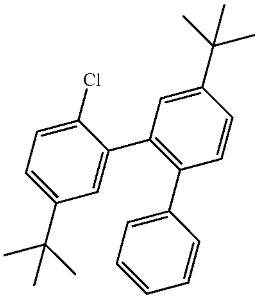
Sub 2-33
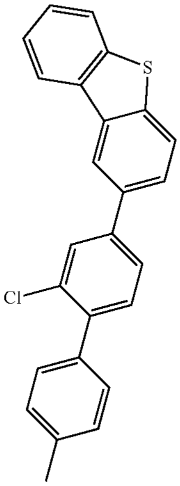
-continued
Sub 2-34
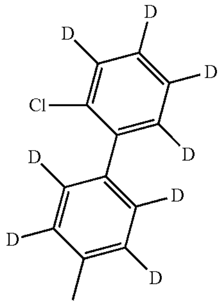
Sub 2-35
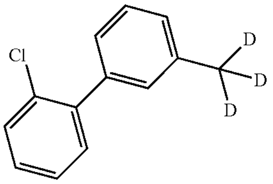
Sub 2-36
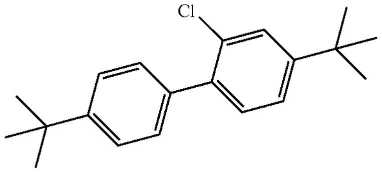
Sub 2-37
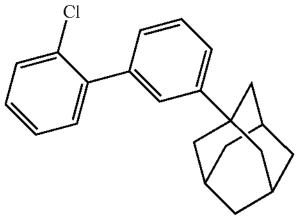
Sub 2-38
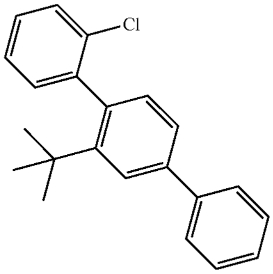
Sub 2-39
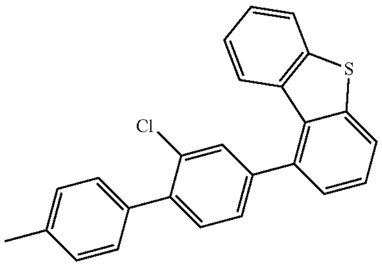

-continued
Sub 2-40
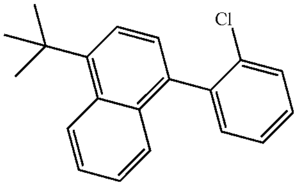
Sub 2-41
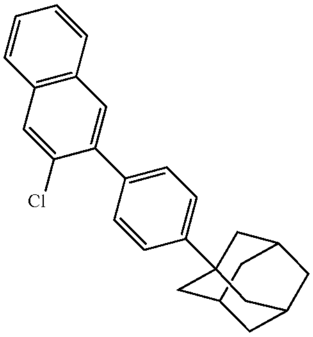
Sub 2-42
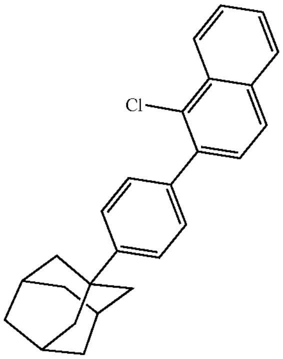
Sub 2-43
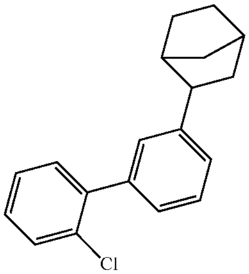
Sub 2-44
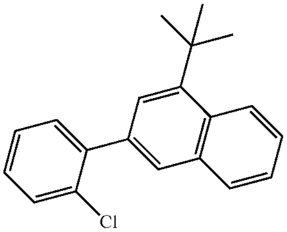
-continued
Sub 2-45
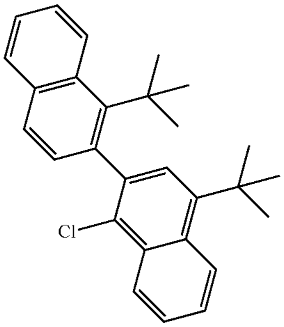
Sub 2-46
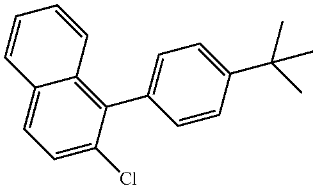
Sub 2-47
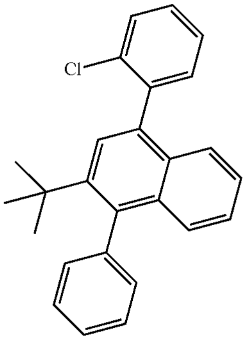
Sub 2-48
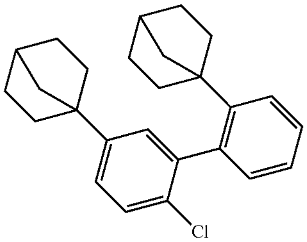
Sub 2-49
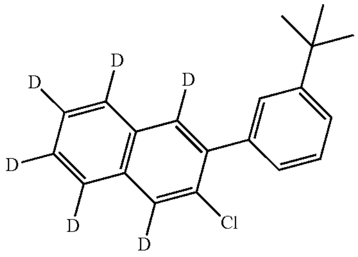
TABLE 2
| Compound | FD-MS |
| --- | --- |
| Sub 2-1 | m/z = 244.10($C_{16}H_{17}Cl$ = 244.76) |
| Sub 2-2 | m/z = 270.12($C_{18}H_{19}Cl$ = 270.80) |
| Sub 2-3 | m/z = 244.10($C_{16}H_{17}Cl$ = 244.76) |
| Sub 2-4 | m/z = 282.12($C_{19}H_{19}Cl$ = 282.81) |
| Sub 2-5 | m/z = 230.09($C_{15}H_{15}Cl$ = 230.74) |

TABLE 2-continued

| Compound | FD-MS |
|---|---|
| Sub 2-6 | m/z = 216.07($C_{14}H_{13}Cl$ = 216.71) |
| Sub 2-7 | m/z = 284.13($C_{19}H_{21}Cl$ = 284.83) |
| Sub 2-8 | m/z = 244.10($C_{16}H_{17}Cl$ = 244.76) |
| Sub 2-9 | m/z = 270.12($C_{18}H_{19}Cl$ = 270.80) |
| Sub 2-10 | m/z = 322.15($C_{22}H_{23}Cl$ = 322.88) |
| Sub 2-11 | m/z = 282.12($C_{19}H_{19}Cl$ = 282.81) |
| Sub 2-12 | m/z = 320.13($C_{22}H_{21}Cl$ = 320.86) |
| Sub 2-13 | m/z = 320.13($C_{22}H_{21}Cl$ = 320.86) |
| Sub 2-14 | m/z = 230.09($C_{15}H_{15}Cl$ = 230.74) |
| Sub 2-15 | m/z = 322.15($C_{22}H_{23}Cl$ = 322.88) |
| Sub 2-16 | m/z = 320.13($C_{22}H_{21}Cl$ = 320.86) |
| Sub 2-17 | m/z = 282.12($C_{19}H_{19}Cl$ = 282.81) |
| Sub 2-18 | m/z = 270.12($C_{18}H_{19}Cl$ = 270.80) |
| Sub 2-19 | m/z = 230.09($C_{15}H_{15}Cl$ = 230.74) |
| Sub 2-20 | m/z = 396.16($C_{28}H_{25}Cl$ = 396.96) |
| Sub 2-21 | m/z = 320.13($C_{22}H_{21}Cl$ = 320.86) |
| Sub 2-22 | m/z = 394.15($C_{28}H_{23}Cl$ = 394.94) |
| Sub 2-23 | m/z = 410.14($C_{28}H_{23}ClO$ = 410.94) |
| Sub 2-24 | m/z = 270.12($C_{18}H_{19}Cl$ = 270.80) |
| Sub 2-25 | m/z = 224.12($C_{14}H_5D_8Cl$ = 224.76) |
| Sub 2-26 | m/z = 230.09($C_{15}H_{15}Cl$ = 230.74) |
| Sub 2-27 | m/z = 202.05($C_{13}H_{11}Cl$ = 202.68) |
| Sub 2-28 | m/z = 364.20($C_{25}H_{29}Cl$ = 364.96) |
| Sub 2-29 | m/z = 230.09($C_{15}H_{15}Cl$ = 230.74) |
| Sub 2-30 | m/z = 320.13($C_{22}H_{21}Cl$ = 320.86) |
| Sub 2-31 | m/z = 282.12($C_{19}H_{19}Cl$ = 282.81) |
| Sub 2-32 | m/z = 376.20($C_{26}H_{29}Cl$ = 376.97) |
| Sub 2-33 | m/z = 384.07($C_{25}H_{17}ClS$ = 384.92) |
| Sub 2-34 | m/z = 210.11($C_{13}H_3D_8Cl$ = 210.73) |
| Sub 2-35 | m/z = 205.07($C_{13}H_8D_3Cl$ = 205.70) |
| Sub 2-36 | m/z = 300.16($C_{20}H_{25}Cl$ = 300.87) |
| Sub 2-37 | m/z = 322.15($C_{22}H_{23}Cl$ = 322.88) |
| Sub 2-38 | m/z = 320.13($C_{22}H_{21}Cl$ = 320.86) |
| Sub 2-39 | m/z = 384.07($C_{25}H_{17}ClS$ = 384.92) |
| Sub 2-40 | m/z = 294.12($C_{20}H_{19}Cl$ = 294.82) |
| Sub 2-41 | m/z = 372.16($C_{26}H_{25}Cl$ = 372.94) |
| Sub 2-42 | m/z = 372.16($C_{26}H_{25}Cl$ = 372.94) |
| Sub 2-43 | m/z = 282.12($C_{19}H_{19}Cl$ = 282.81) |
| Sub 2-44 | m/z = 294.12($C_{20}H_{19}Cl$ = 294.82) |
| Sub 2-45 | m/z = 400.20($C_{28}H_{29}Cl$ = 400.99) |
| Sub 2-46 | m/z = 294.12($C_{20}H_{19}Cl$ = 294.82) |
| Sub 2-47 | m/z = 370.15($C_{26}H_{23}Cl$ = 370.92) |
| Sub 2-48 | m/z = 376.20($C_{26}H_{29}Cl$ = 376.97) |
| Sub 2-49 | m/z = 300.16($C_{20}H_{13}D_6Cl$ = 300.86) |

The FD-MS (Field Desorption-Mass Spectrometry) values of compounds P-1 to P-160 of the present invention manufactured according to the above synthetic examples are as shown in Table 3.

TABLE 3

| Compound | FD-MS |
|---|---|
| P-1 | m/z = 499.31($C_{37}H_{29}D_6N$ = 499.73) |
| P-2 | m/z = 601.36($C_{45}H_{35}D_6N$ = 601.87) |
| P-3 | m/z = 599.35($C_{45}H_{33}D_6N$ = 599.85) |
| P-4 | m/z = 663.38($C_{50}H_{37}D_6N$ = 663.94) |
| P-5 | m/z = 611.35($C_{46}H_{33}D_6N$ = 611.86) |
| P-6 | m/z = 673.36($C_{51}H_{35}D_6N$ = 673.93) |
| P-7 | m/z = 645.33($C_{46}H_{35}D_6NS$ = 645.94) |
| P-8 | m/z = 665.36($C_{49}H_{35}D_6NO$ = 665.91) |
| P-9 | m/z = 631.41($C_{47}H_{41}D_6N$ = 631.94) |
| P-10 | m/z = 683.44($C_{51}H_{45}D_6N$ = 684.01) |
| P-11 | m/z = 742.42($C_{55}H_{42}D_6N_2$ = 743.04) |
| P-12 | m/z = 729.42($C_{55}H_{43}D_6N$ = 730.04) |
| P-13 | m/z = 835.41($C_{61}H_{45}D_6NS$ = 836.18) |
| P-14 | m/z = 697.45($C_{52}H_{35}D_{12}N$ = 698.03) |
| P-15 | m/z = 817.42($C_{61}H_{43}D_6NO$ = 818.11) |
| P-16 | m/z = 731.43($C_{55}H_{37}D_{10}N$ = 732.05) |
| P-17 | m/z = 611.35($C_{46}H_{33}D_6N$ = 611.86) |
| P-18 | m/z = 681.42($C_{51}H_{43}D_6N$ = 682.00) |
| P-19 | m/z = 753.42($C_{57}H_{43}D_6N$ = 754.06) |
| P-20 | m/z = 767.44($C_{58}H_{45}D_6N$ = 768.09) |
| P-21 | m/z = 757.36($C_{55}H_{39}D_6NS$ = 758.07) |
| P-22 | m/z = 702.39($C_{52}H_{38}D_6N_2$ = 702.97) |

TABLE 3-continued

| Compound | FD-MS |
|---|---|
| P-23 | m/z = 549.33($C_{41}H_{31}D_6N$ = 549.79) |
| P-24 | m/z = 549.33($C_{41}H_{31}D_6N$ = 549.79) |
| P-25 | m/z = 575.35($C_{43}H_{33}D_6N$ = 575.83) |
| P-26 | m/z = 625.36($C_{47}H_{35}D_6N$ = 625.89) |
| P-27 | m/z = 540.35($C_{40}H_{24}D_{11}N$ = 540.79) |
| P-28 | m/z = 703.41($C_{53}H_{41}D_6N$ = 704.00) |
| P-29 | m/z = 651.38($C_{49}H_{37}D_6N$ = 651.93) |
| P-30 | m/z = 651.38($C_{49}H_{37}D_6N$ = 651.93) |
| P-31 | m/z = 649.36($C_{49}H_{35}D_6N$ = 649.91) |
| P-32 | m/z = 741.39($C_{55}H_{39}D_6NO$ = 742.01) |
| P-33 | m/z = 715.37($C_{53}H_{37}D_6NO$ = 715.97) |
| P-34 | m/z = 747.46($C_{56}H_{37}D_{12}N$ = 748.09) |
| P-35 | m/z = 731.35($C_{53}H_{37}D_6NS$ = 732.03) |
| P-36 | m/z = 758.46($C_{57}H_{38}D_{11}N$ = 759.09) |
| P-37 | m/z = 484.36($C_{35}H_{12}D_{19}N$ = 484.76) |
| P-38 | m/z = 651.34($C_{48}H_{33}D_6NO$ = 651.88) |
| P-39 | m/z = 687.47($C_{51}H_{49}D_6N$ = 688.04) |
| P-40 | m/z = 563.26($C_{40}H_{25}D_6NS$ = 563.79) |
| P-41 | m/z = 575.35($C_{43}H_{33}D_6N$ = 575.83) |
| P-42 | m/z = 655.41($C_{49}H_{41}D_6N$ = 655.96) |
| P-43 | m/z = 549.33($C_{41}H_{31}D_6N$ = 549.79) |
| P-44 | m/z = 745.46($C_{56}H_{47}D_6N$ = 746.08) |
| P-45 | m/z = 589.36($C_{44}H_{35}D_6N$ = 589.86) |
| P-46 | m/z = 687.38($C_{52}H_{37}D_6N$ = 687.96) |
| P-47 | m/z = 763.41($C_{58}H_{41}D_6N$ = 764.06) |
| P-48 | m/z = 681.33($C_{49}H_{35}D_6NS$ = 681.97) |
| P-49 | m/z = 739.41($C_{56}H_{41}D_6N$ = 740.04) |
| P-50 | m/z = 691.41($C_{52}H_{41}D_6N$ = 691.99) |
| P-51 | m/z = 818.45($C_{61}H_{46}D_6N_2$ = 819.14) |
| P-52 | m/z = 729.42($C_{55}H_{43}D_6N$ = 730.04) |
| P-53 | m/z = 819.43($C_{61}H_{45}D_6NO$ = 820.12) |
| P-54 | m/z = 697.45($C_{52}H_{35}D_{12}N$ = 698.03) |
| P-55 | m/z = 741.39($C_{55}H_{39}D_6NO$ = 742.01) |
| P-56 | m/z = 705.42($C_{53}H_{35}D_{10}N$ = 706.01) |
| P-57 | m/z = 611.35($C_{46}H_{33}D_6N$ = 611.86) |
| P-58 | m/z = 681.42($C_{51}H_{43}D_6N$ = 682.00) |
| P-59 | m/z = 753.42($C_{57}H_{43}D_6N$ = 754.06) |
| P-60 | m/z = 767.44($C_{58}H_{45}D_6N$ = 768.09) |
| P-61 | m/z = 741.39($C_{55}H_{39}D_6NO$ = 742.01) |
| P-62 | m/z = 778.42($C_{58}H_{42}D_6N_2$ = 779.07) |
| P-63 | m/z = 549.33($C_{41}H_{31}D_6N$ = 549.79) |
| P-64 | m/z = 549.33($C_{41}H_{31}D_6N$ = 549.79) |
| P-65 | m/z = 575.35($C_{43}H_{33}D_6N$ = 575.83) |
| P-66 | m/z = 625.36($C_{47}H_{35}D_6N$ = 625.89) |
| P-67 | m/z = 580.38($C_{43}H_{28}D_{11}N$ = 580.86) |
| P-68 | m/z = 703.41($C_{53}H_{41}D_6N$ = 704.00) |
| P-69 | m/z = 651.38($C_{49}H_{37}D_6N$ = 651.93) |
| P-70 | m/z = 631.41($C_{47}H_{41}D_6N$ = 631.94) |
| P-71 | m/z = 639.29($C_{46}H_{29}D_6NS$ = 639.89) |
| P-72 | m/z = 815.44($C_{62}H_{45}D_6N$ = 816.13) |
| P-73 | m/z = 731.35($C_{53}H_{37}D_6NS$ = 732.03) |
| P-74 | m/z = 747.46($C_{56}H_{37}D_{12}N$ = 748.09) |
| P-75 | m/z = 731.35($C_{53}H_{37}D_6NS$ = 732.03) |
| P-76 | m/z = 785.49($C_{59}H_{51}D_6N$ = 786.15) |
| P-77 | m/z = 470.35($C_{34}H_{10}D_{19}N$ = 470.73) |
| P-78 | m/z = 626.33($C_{46}H_{26}D_9NO$ = 626.85) |
| P-79 | m/z = 589.36($C_{44}H_{35}D_6N$ = 589.86) |
| P-80 | m/z = 958.59($C_{72}H_{34}D_{23}N$ = 959.4) |
| P-81 | m/z = 575.35($C_{43}H_{33}D_6N$ = 575.83) |
| P-82 | m/z = 641.39($C_{48}H_{39}D_6N$ = 641.93) |
| P-83 | m/z = 767.44($C_{58}H_{45}D_6N$ = 768.09) |
| P-84 | m/z = 759.47($C_{57}H_{49}D_6N$ = 760.11) |
| P-85 | m/z = 703.37($C_{52}H_{37}D_6NO$ = 703.96) |
| P-86 | m/z = 681.33($C_{49}H_{35}D_6NS$ = 681.97) |
| P-87 | m/z = 740.40($C_{55}H_{40}D_6N_2$ = 741.02) |
| P-88 | m/z = 725.39($C_{55}H_{39}D_6N$ = 726.01) |
| P-89 | m/z = 691.41($C_{52}H_{41}D_6N$ = 691.99) |
| P-90 | m/z = 769.46($C_{58}H_{47}D_6N$ = 770.11) |
| P-91 | m/z = 719.35($C_{52}H_{37}D_6NS$ = 720.02) |
| P-92 | m/z = 713.36($C_{53}H_{35}D_6NO$ = 713.95) |
| P-93 | m/z = 605.30($C_{43}H_{31}D_6NS$ = 605.87) |
| P-94 | m/z = 665.36($C_{49}H_{35}D_6NO$ = 665.91) |
| P-95 | m/z = 720.44($C_{53}H_{44}D_6N_2$ = 721.03) |
| P-96 | m/z = 623.35($C_{47}H_{33}D_6N$ = 623.87) |
| P-97 | m/z = 765.42($C_{58}H_{43}D_6N$ = 766.07) |
| P-98 | m/z = 533.30($C_{40}H_{27}D_6N$ = 533.75) |
| P-99 | m/z = 703.41($C_{53}H_{41}D_6N$ = 704.00) |
| P-100 | m/z = 639.29($C_{46}H_{29}D_6NS$ = 639.89) |

TABLE 3-continued

| Compound | FD-MS |
|---|---|
| P-101 | m/z = 727.41($C_{55}H_{41}D_6N$ = 728.02) |
| P-102 | m/z = 651.38($C_{49}H_{37}D_6N$ = 651.93) |
| P-103 | m/z = 625.36($C_{47}H_{35}D_6N$ = 625.89) |
| P-104 | m/z = 707.44($C_{53}H_{45}D_6N$ = 708.03) |
| P-105 | m/z = 692.37($C_{50}H_{36}D_6N_2O$ = 692.94) |
| P-106 | m/z = 625.36($C_{47}H_{35}D_6N$ = 625.89) |
| P-107 | m/z = 580.38($C_{43}H_{28}D_{11}N$ = 580.86) |
| P-108 | m/z = 707.44($C_{53}H_{45}D_6N$ = 708.03) |
| P-109 | m/z = 649.36($C_{49}H_{35}D_6N$ = 649.91) |
| P-110 | m/z = 681.42($C_{51}H_{43}D_6N$ = 682.00) |
| P-111 | m/z = 689.30($C_{50}H_{31}D_6NS$ = 689.95) |
| P-112 | m/z = 639.38($C_{48}H_{37}D_6N$ = 639.92) |
| P-113 | m/z = 781.36($C_{57}H_{39}D_6NS$ = 782.09) |
| P-114 | m/z = 747.46($C_{56}H_{37}D_{12}N$ = 748.09) |
| P-115 | m/z = 711.38($C_{51}H_{41}D_6NS$ = 712.04) |
| P-116 | m/z = 835.5($C_{63}H_{53}D_6N$ = 836.21) |
| P-117 | m/z = 550.41($C_{40}H_{10}D_{23}N$ = 550.85) |
| P-118 | m/z = 625.34($C_{46}H_{27}D_9N_2$ = 625.86) |
| P-119 | m/z = 701.39($C_{53}H_{39}D_6N$ = 701.99) |
| P-120 | m/z = 756.44($C_{57}H_{40}D_9N$ = 757.08) |
| P-121 | m/z = 499.31($C_{37}H_{29}D_6N$ = 499.73) |
| P-122 | m/z = 715.41($C_{54}H_{41}D_6N$ = 716.01) |
| P-123 | m/z = 727.41($C_{55}H_{41}D_6N$ = 728.02) |
| P-124 | m/z = 753.42($C_{57}H_{43}D_6N$ = 754.06) |
| P-125 | m/z = 643.32($C_{46}H_{33}D_6NS$ = 643.92) |
| P-126 | m/z = 789.42($C_{60}H_{43}D_6N$ = 790.10) |
| P-127 | m/z = 745.42($C_{55}H_{43}D_6NO$ = 746.04) |
| P-128 | m/z = 797.36($C_{57}H_{39}D_6NOS$ = 798.09) |
| P-129 | m/z = 563.35($C_{42}H_{33}D_6N$ = 563.82) |
| P-130 | m/z = 599.35($C_{45}H_{33}D_6N$ = 599.85) |
| P-131 | m/z = 675.38($C_{51}H_{37}D_6N$ = 675.95) |
| P-132 | m/z = 641.39($C_{48}H_{39}D_6N$ = 641.93) |
| P-133 | m/z = 639.34($C_{47}H_{33}D_6NO$ = 639.87) |
| P-134 | m/z = 681.33($C_{49}H_{35}D_6NS$ = 681.97) |
| P-135 | m/z = 740.40($C_{55}H_{40}D_6N_2$ = 741.02) |
| P-136 | m/z = 863.44($C_{63}H_{49}D_6NS$ = 864.24) |
| P-137 | m/z = 506.36($C_{37}H_{22}D_{13}N$ = 506.77) |
| P-138 | m/z = 560.40($C_{41}H_{20}D_{17}N$ = 560.86) |
| P-139 | m/z = 674.42($C_{49}H_{30}D_{13}NO$ = 674.97) |
| P-140 | m/z = 681.35($C_{49}H_{35}D_6NO_2$ = 681.91) |
| P-141 | m/z = 717.42($C_{54}H_{43}D_6N$ = 718.03) |
| P-142 | m/z = 587.35($C_{44}H_{33}D_6N$ = 587.84) |
| P-143 | m/z = 767.44($C_{58}H_{45}D_6N$ = 768.09) |
| P-144 | m/z = 769.46($C_{58}H_{47}D_6N$ = 770.11) |
| P-145 | m/z = 739.41($C_{56}H_{41}D_6N$ = 740.04) |
| P-146 | m/z = 711.38($C_{54}H_{37}D_6N$ = 711.98) |
| P-147 | m/z = 593.38($C_{44}H_{27}D_{12}N$ = 593.88) |
| P-148 | m/z = 593.38($C_{44}H_{27}D_{12}N$ = 593.88) |
| P-149 | m/z = 691.41 ($C_{52}H_{41}D_6N$ = 691.99) |
| P-150 | m/z = 652.38($C_{49}H_{32}D_9N$ = 652.93) |
| P-151 | m/z = 691.41($C_{52}H_{41}D_6N$ = 691.99) |
| P-152 | m/z = 649.36($C_{49}H_{35}D_6N$ = 649.91) |
| P-153 | m/z = 743.44($C_{56}H_{45}D_6N$ = 744.07) |
| P-154 | m/z = 691.41($C_{52}H_{41}D_6N$ = 691.99) |
| P-155 | m/z = 703.41 ($C_{53}H_{41}D_6N$ = 704) |
| P-156 | m/z = 725.39($C_{55}H_{39}D_6N$ = 726.01) |
| P-157 | m/z = 691.41($C_{52}H_{41}D_6N$ = 691.99) |
| P-158 | m/z = 793.46($C_{60}H_{47}D_6N$ = 794.13) |
| P-159 | m/z = 649.36($C_{49}H_{35}D_6N$ = 649.91) |
| P-160 | m/z = 677.39($C_{51}H_{39}D_6N$ = 677.96) |

In the above, exemplary synthesis examples of the present invention represented by Formula 1 have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095.), Pd(II)-catalyzed oxidative cyclization reaction (*Org. Lett.* 2011, 13, 5504), and $PPh_3$-mediated reductive cyclization reaction (*J. Org. Chem.* 2005, 70, 5014.), and it will be easily understood by those skilled in the art that the reaction proceeds even when other substituents defined in Formula 1 are bonded in addition to the substituents specified in the specific synthesis examples.

Manufacturing Evaluation of Organic Electroluminescent Devices

[Example 1] Red Organic Light Emitting Device (Emitting-Auxiliary Layer)

Compound A and Compound B were used on an ITO layer (anode) formed on a glass substrate, and Compound B was doped at a weight ratio of 98:2 to form a hole injection layer with a thickness of 10 nm. Then, Compound A was vacuum-deposited on the hole injection layer with a thickness of 110 nm to form a hole transport layer.

Next, the compound P-1 of the present invention was vacuum-deposited to a thickness of 10 nm on the hole transport layer to form an emitting auxiliary layer. Afterwards, compound D-R was used as the host material of the emitting layer, and bis-(1-phenylisoquinolyl)iridium(III) acetylacetonate (hereinafter abbreviated by '$(piq)_2Ir(acac)$') was used as the dopant material, and the dopant was doped so that the weight ratio of the host and dopant was 95:5 to form an emitting layer with a thickness of 30 nm.

Next, compound E was vacuum-deposited on the emitting layer to form a hole blocking layer with a thickness of 10 nm, and a mixture of compound F and compound G at a weight ratio of 5:5 was used to form an electron transport layer with a thickness of 30 nm on the hole-blocking layer. Afterwards, compound G was deposited on the electron transport layer to form an electron injection layer with a thickness of 0.2 nm, and then Al was deposited to form a cathode with a thickness of 150 nm.

compound A: N-([1,1'-biphenyl]-4-yl)-9,9-dimethyl-N-(4-(9-phenyl-9H-carbazol-3-yl)phenyl)-9H-fluoren-2-amine compound B: 4,4',4"-((1E,1'E,1"E)-cyclopropane-1,2,3-triylidenetris(cyanomethaneylylidene))tris(2,3,5,6-tetrafluorobenzonitrile)

compound D-R 14-(4-phenylquinazolin-2-yl)-14H-benzo[c]benzo[4,5]thieno[2,3-a]carbazole compound E: 2-(4'-(9,9-dimethyl-9H-fluoren-2-yl)-[1,1'-biphenyl]-3-yl)-4,6-diphenyl-1,3,5-triazine compound F: 2,7-bis(4-(4,6-diphenyl-1,3,5-triazin-2-yl)phenyl)naphthalene compound G: (8-quinolinolato)lithium

[Example 2] to [Example 35]

An organic light emitting device was manufactured in the same manner as in Example 1, except that the compound of the present invention described in Table 4 was used instead of the compound P-1 of the present invention as an emitting auxiliary layer material.

[Comparative Example 1] and [Comparative Example 7]

An organic light emitting device was manufactured in the same manner as in Example 1, except that the comparative compounds A to G were used instead of the compound P-1 of the present invention as an emitting auxiliary layer material.

[comparative compound A]
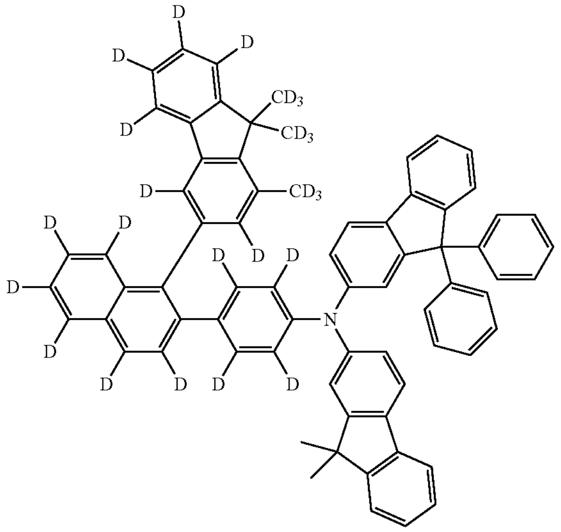
[comparative compound B]
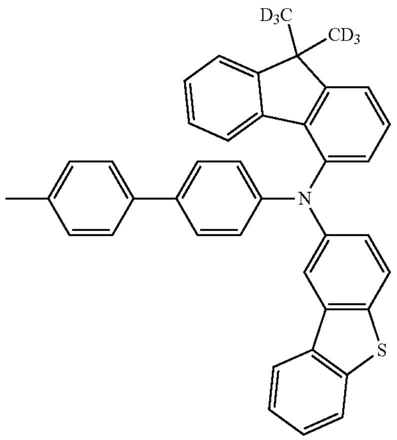
[comparative compound C]
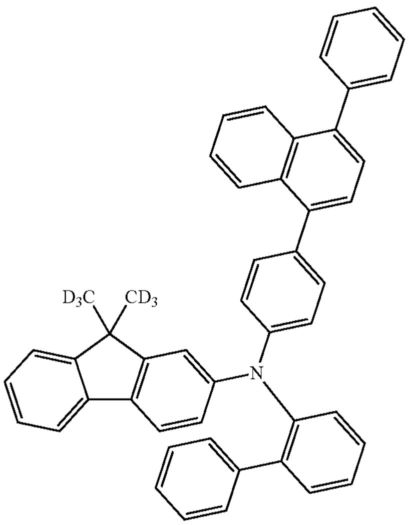
-continued
[comparative compound D]
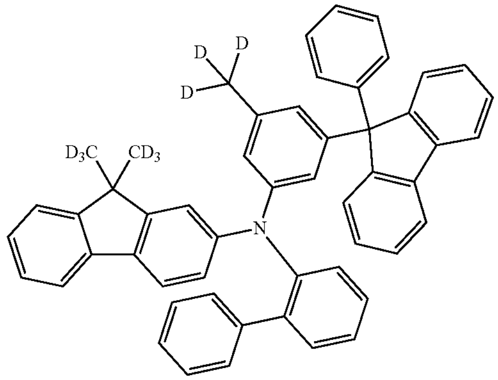
[comparative compound E]
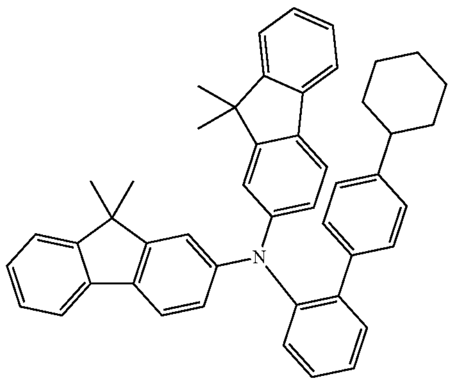
[comparative compound F]
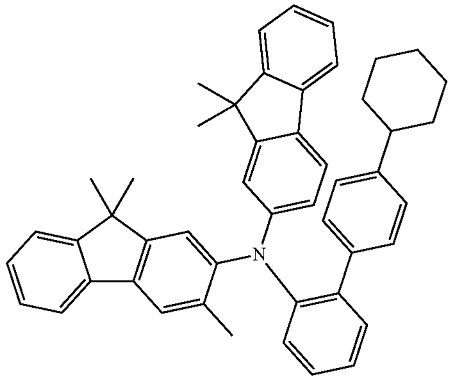

-continued

[comparative compound G]

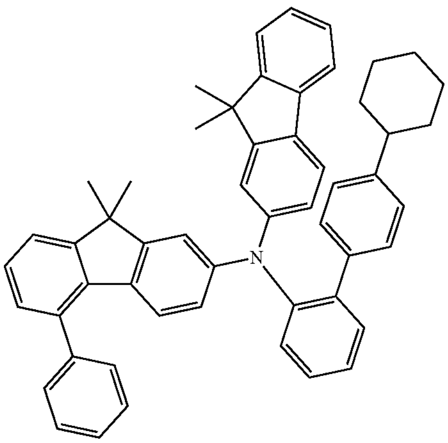

The electroluminescence (EL) characteristics were measured using PR-650 from Photoresearch by applying a forward bias DC voltage to the organic electroluminescence devices manufactured by Examples 1 to 35 and Comparative Examples 1 to 7 of the present invention. As a result of the measurement, the T95 lifespan was measured using a lifespan measuring device manufactured by Max Science at a standard brightness of 2,500 cd/m$^2$. Table 4 shows the results of the device fabrication and evaluation.

The measuring apparatus can evaluate the performance of new materials compared to comparative compounds under identical conditions, without being affected by possible daily fluctuations in deposition rate, vacuum quality or other parameters.

During the evaluation, one batch contains 4 identically prepared OLEDs including a comparative compound, and the performance of a total of 12 OLEDs is evaluated in 3 batches, so the value of the experimental results obtained in this way indicates statistical significance.

TABLE 4

| | compound | Driving voltage | Current Density (mA/cm$^2$) | Brightness (cd/m$^2$) | Efficiency (cd/A) | T(95) |
|---|---|---|---|---|---|---|
| comparative example 1 | comparative compound A | 5.4 | 16.2 | 2500.0 | 15.4 | 87.7 |
| comparative example 2 | comparative compound B | 5.3 | 15.3 | 2500.0 | 16.3 | 90.9 |
| comparative example 3 | comparative compound C | 5.2 | 13.7 | 2500.0 | 18.2 | 98.6 |
| comparative example 4 | comparative compound D | 5.3 | 14.3 | 2500.0 | 17.5 | 94.8 |
| comparative example 5 | comparative compound E | 5.3 | 15.7 | 2500.0 | 15.9 | 95.3 |
| comparative example 6 | comparative compound F | 5.4 | 13.5 | 2500.0 | 18.5 | 96.5 |
| comparative example 7 | comparative compound G | 5.4 | 14.0 | 2500.0 | 17.8 | 94.2 |
| example 1 | P-1 | 4.3 | 7.2 | 2500.0 | 34.7 | 121.2 |
| example 2 | P-12 | 4.2 | 7.0 | 2500.0 | 35.9 | 120.9 |
| example 3 | P-15 | 4.3 | 7.4 | 2500.0 | 33.8 | 120.0 |
| example 4 | P-25 | 4.2 | 7.1 | 2500.0 | 35.0 | 121.2 |
| example 5 | P-36 | 4.3 | 7.2 | 2500.0 | 34.9 | 123.7 |
| example 6 | P-40 | 4.3 | 7.3 | 2500.0 | 34.3 | 119.7 |
| example 7 | P-47 | 4.3 | 7.9 | 2500.0 | 31.7 | 117.4 |
| example 8 | P-60 | 4.4 | 7.6 | 2500.0 | 32.8 | 115.8 |
| example 9 | P-64 | 4.4 | 7.7 | 2500.0 | 32.6 | 111.1 |
| example 10 | P-68 | 4.4 | 7.8 | 2500.0 | 32.1 | 114.1 |

TABLE 4-continued

| | compound | Driving voltage | Current Density (mA/cm$^2$) | Brightness (cd/m$^2$) | Efficiency (cd/A) | T(95) |
|---|---|---|---|---|---|---|
| example 11 | P-75 | 4.4 | 8.3 | 2500.0 | 30.2 | 110.6 |
| example 12 | P-80 | 4.4 | 7.5 | 2500.0 | 33.5 | 116.8 |
| example 13 | P-81 | 4.1 | 6.7 | 2500.0 | 37.3 | 124.8 |
| example 14 | P-84 | 4.1 | 6.8 | 2500.0 | 36.7 | 127.2 |
| example 15 | P-85 | 4.2 | 6.9 | 2500.0 | 36.3 | 124.5 |
| example 16 | P-89 | 4.1 | 6.3 | 2500.0 | 40.0 | 129.7 |
| example 17 | P-92 | 4.1 | 6.9 | 2500.0 | 36.1 | 124.9 |
| example 18 | P-102 | 4.3 | 6.7 | 2500.0 | 37.1 | 125.3 |
| example 19 | P-114 | 4.2 | 6.6 | 2500.0 | 38.0 | 124.6 |
| example 20 | P-117 | 4.2 | 6.5 | 2500.0 | 38.6 | 124.7 |
| example 21 | P-119 | 4.2 | 6.4 | 2500.0 | 39.2 | 125.5 |
| example 22 | P-120 | 4.2 | 6.9 | 2500.0 | 36.1 | 128.5 |
| example 23 | P-128 | 4.4 | 8.2 | 2500.0 | 30.5 | 110.9 |
| example 24 | P-131 | 4.3 | 8.0 | 2500.0 | 31.2 | 111.4 |
| example 25 | P-137 | 4.3 | 7.8 | 2500.0 | 32.0 | 118.6 |
| example 26 | P-138 | 4.4 | 8.2 | 2500.0 | 30.6 | 116.9 |
| example 27 | P-141 | 4.1 | 6.3 | 2500.0 | 39.9 | 130.1 |
| example 28 | P-142 | 4.2 | 6.7 | 2500.0 | 37.5 | 125.8 |
| example 29 | P-143 | 4.8 | 8.5 | 2500.0 | 29.3 | 109.6 |
| example 30 | P-144 | 4.3 | 6.9 | 2500.0 | 36.3 | 124.2 |
| example 31 | P-148 | 4.7 | 8.4 | 2500.0 | 29.9 | 108.7 |
| example 32 | P-152 | 4.2 | 7.0 | 2500.0 | 35.6 | 120.4 |
| example 33 | P-154 | 4.5 | 8.1 | 2500.0 | 30.9 | 111.5 |
| example 34 | P-158 | 4.4 | 7.7 | 2500.0 | 32.4 | 114.9 |
| example 35 | P-160 | 4.2 | 6.5 | 2500.0 | 38.4 | 126.3 |

Comparative compounds A to D are similar to the compound of the present invention in that they are tertiary amine compounds comprising a structure in which $CD_3$ is disubstituted at position 9 of fluorene (hereinafter, parent nucleus), but the compound of the present invention is different from the comparative compounds in that it necessarily comprises a substituent comprising an o-biphenyl skeleton substituted with an alkyl group or an aliphatic ring group. Comparative compounds E to G comprise a substituent comprising an o-biphenyl skeleton substituted with an alkyl group or an aliphatic ring group, and are similar to the compounds of the present invention in that fluorene is disubstituted, but differ from the compounds of the present invention in that $CD_3$ is not substituted at position 9 of fluorene.

In the case of comparative compound A, it is similar to the compound of the present invention in that one of the substituents of the remaining amine other than the parent nucleus contains an alkyl group (9, 9'-dimethylfluorene), but the compound of the present invention is different from comparative compound A in that an alkyl group is substituted at the terminal of the substituent. In order to confirm the energy level difference of the compound due to such structural difference, data measured using the DFT method (B3LYP/6-31g(D)) of the Gaussian program for the comparative compound A and the compound P-80 of the present invention having the most similar structure thereto are as shown in Table 5.

TABLE 5

| compound | Comparative compound A | P-80 |
|---|---|---|
| HOMO(eV) | −4.701 | −4.769 |

As can be seen from the results in Table 5, it can be confirmed that the HOMO Energy Level (hereinafter, HOMO) value of compound P-80 of the present invention is deeper than that of comparative compound A. As a result, when the compound of the present invention is applied to a device, it is thought that hole transfer from the emitting auxiliary layer to the emitting layer becomes easier than with the comparative compound A, so that the hole accumulation in the device decreases and the charge balance increases, thereby significantly improving the efficiency and lifespan of the device.

Next, in the case of comparative compounds B to D, they are similar to the compounds of the present invention in that one of the substituents of the remaining amine other than the parent nucleus includes a biphenyl moiety, but comparative compound B differs from the compound of the present invention in that it contains p-biphenyl rather than o-biphenyl, and comparative compound c and comparative compound D differ from the compound of the present invention in that they contain an o-biphenyl skeleton, but the alkyl or aliphatic ring group is unsubstituted. In order to confirm the influence due to the difference in these substituents, the data for measuring the Reorganization Energy (unit: eV, hereinafter $RE_{hole}$) of compounds of the present invention similar to Compounds B to D using molecular simulation (Schrodinger Materials Science Suite 4.9.128) are as shown in Table 6.

TABLE 6

| compound | $RE_{hole}$(eV) |
|---|---|
| comparative compound B | 0.1900 |
| comparative compound C | 0.1603 |
| comparative compound D | 0.1636 |
| P-40 | 0.1500 |
| P-119 | 0.1546 |
| P-120 | 0.1597 |

As can be seen from the results in Table 6, it can be confirmed that the $RE_{hole}$ values of the compounds of the present invention are significantly lower than the $RE_{hole}$ values of comparative compounds B to D. As a result, when the compound of the present invention is applied to a device, hole hopping occurs more quickly within the material than in comparative compounds, thereby improving hole mobility, allowing holes to be transferred to the emitting layer more quickly, reducing electron quenching in the emitting layer, and improving charge balance in the emitting layer as exciton formation becomes easier, resulting in significant improvements in the lifespan, operation, and efficiency of the device.

In the case of comparative compounds E to G, the presence or absence of the substitution of $CD_3$ at position 9 of fluorene is different from that of the compound of the present invention. In the case of the compound of the present invention, it is judged that the compound exhibited superior performance in the device compared to the comparative compounds because the structural stability increased as $CD_3$ was substituted at position 9, which is relatively weak in bonding in the fluorenyl group. From another aspect, based on the device measurement results, in the case where $Ar^1$ is substituted with fluorene in the compound of the present invention, the device performance was measured to be better when an additional substituent was further substituted on the fluorene skeleton, and in particular, compounds having an additional substituent on the ring bonded to the amine in the fluorene skeleton showed better device results than other cases.

In other words, as can be seen from the results in Tables 4 to 6, it can be confirmed that the compound satisfying both the structural features and the configuration disclosed in the present invention exhibits a remarkable effect in the organic electronic element, compared to the comparative compounds A to G having a structurally similar configuration to the compound of the present invention. This means that the compound of the present invention satisfying all the specific configurations exhibits a remarkable effect, compared to other comparative compounds not described in the present specification.

These results suggest that even for compounds with similar molecular components, the properties of the compound, such as hole characteristics, luminous efficiency characteristics, energy levels, hole injection and mobility characteristics, charge balance of holes and electrons, volume density, and intermolecular distance, can differ significantly to an extent that is difficult to predict depending on the type and position of the substituted substituent, and that the performance of an element may vary due to complex factors, rather than a single configuration affecting the outcome of the entire device.

In the case of an emitting auxiliary layer, the relationship between the hole transport layer and the emitting layer (host) must be understood. Therefore, even if a similar core is used, it would be very difficult for even a person skilled in the art to infer the characteristics exhibited in the emitting auxiliary layer in which the compound of the present invention is used.

Additionally, the evaluation results of the described device fabrication explained the device characteristics in which the compound of the present invention was applied only to the emitting auxiliary layer, but the compound of the present invention can be used by applying it to the hole transport layer or by applying it to both the hole transport layer and the emitting auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. A compound represented by Formula 1-2:

Formula 1-2

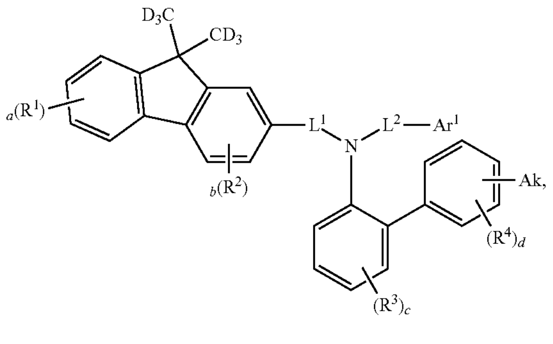

wherein:

$R^1$, $R^2$, $R^3$ and $R^4$ are independently the same or different from each other and are independently selected from the group consisting of hydrogen; deuterium; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; and a $C_3$-$C_{30}$ aliphatic ring, and a plurality of adjacent groups thereof may be bonded to each other to form a ring, wherein the ring formed by adjacent $R^3$ groups is a $C_6$ ring, $L^1$ and $L^2$ are independently a single bond, or selected from the group consisting of Formulae L-1 to L-27:

[Formula L-1]

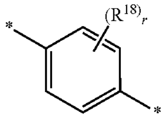

[Formula L-2]

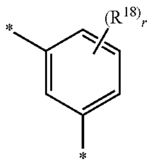

[Formula L-3]

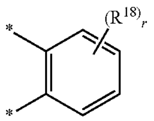

[Formula L-4]

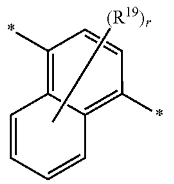

[Formula L-5]

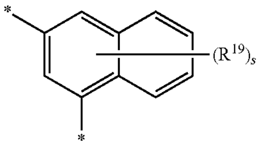

[Formula L-6]

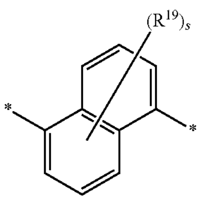

[Formula L-7]

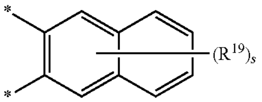

[Formula L-8]

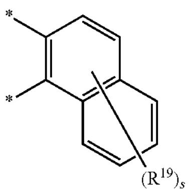

-continued

[Formula L-9]

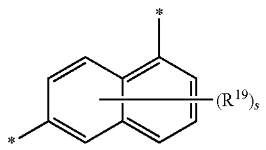

[Formula L-10]

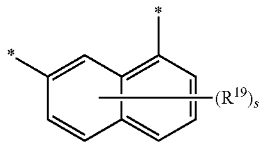

[Formula L-11]

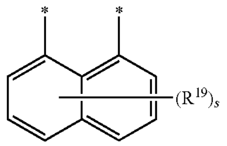

[Formula L-12]

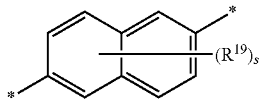

[Formula L-13]

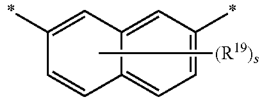

[Formula L-14]

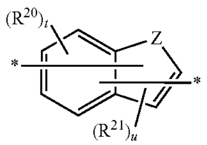

[Formula L-15]

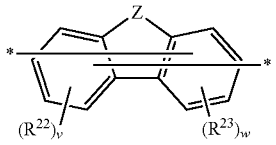

[Formula L-16]

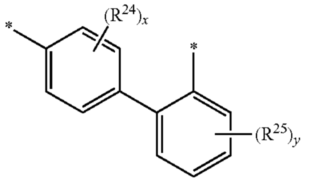

[Formula L-17]

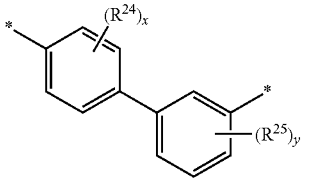

[Formula L-18]

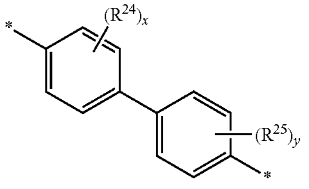

-continued

[Formula L-19]

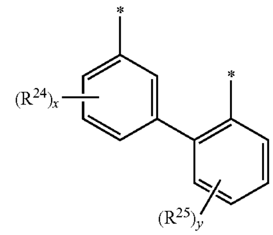

[Formula L-20]

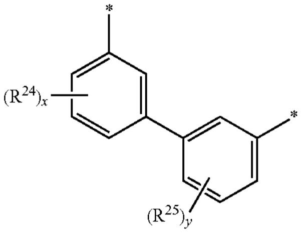

[Formula L-21]

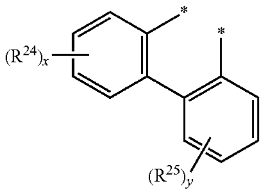

[Formula L-22]

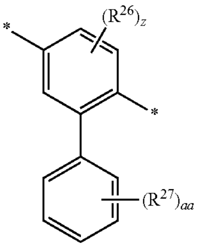

[Formula L-23]

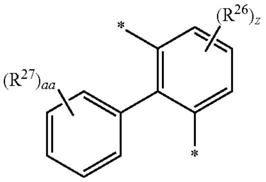

[Formula L-24]

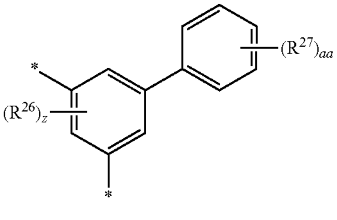

[Formula L-25]

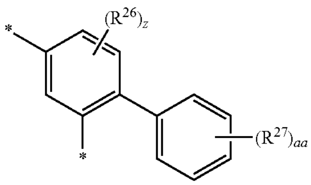

-continued

[Formula L-26]

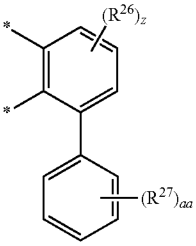

[Formula L-27]

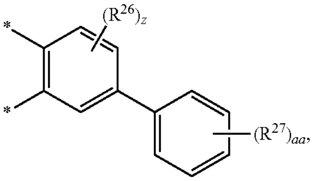

wherein Z is O or S, $R^{18}$, $R^{19}$, $R^{20}$, $R^{21}$, $R^{22}$, $R^{23}$, $R^{24}$, $R^{25}$, $R^{26}$ and $R^{27}$ are independently the same or different from each other and are independently selected from the group consisting of hydrogen; deuterium; a $C_1$-$C_{20}$ alkyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ aliphatic group; a $C_7$-$C_{20}$ arylalkyl group; and a $C_7$-$C_{20}$ alkylaryl group, and a plurality of adjacent groups thereof may be bonded to each other to form a ring, r, t, v, w, x, y and z are independently an integer of 0 to 4, s is an integer of 0 to 6, u is an integer of 0 to 2, aa is an integer of 0 to 5, $Ar^1$ is represented by any one of Formulas Ar-1 to Ar-13:

Ar-1

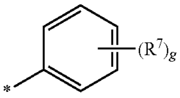

Ar-2

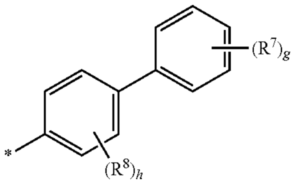

Ar-3

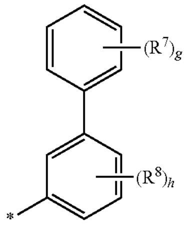

Ar-4

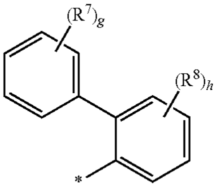

-continued

Ar-5

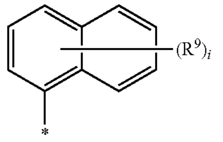

Ar-6

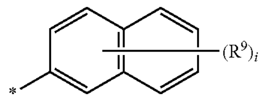

Ar-7

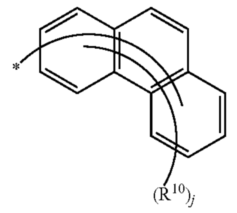

Ar-8

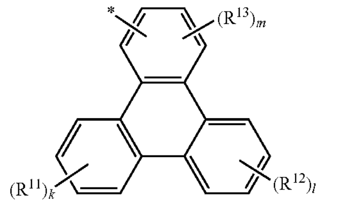

Ar-9

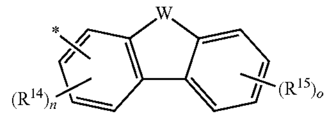

Ar-10

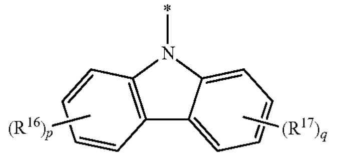

Ar-11

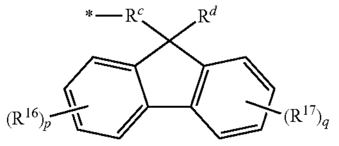

Ar-12

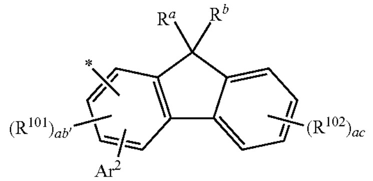

Ar-13

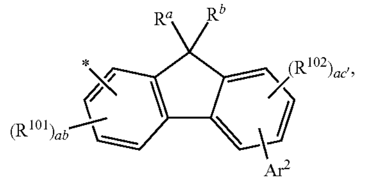

wherein $R^7$, $R^8$, $R^9$, $R^{10}$, $R^{11}$, $R^{12}$, $R^{13}$, $R^{14}$, $R^{15}$, $R^{16}$ and $R^{17}$ are independently the same or different from each other and are independently selected from the group consisting of hydrogen; deuterium; halogen; a cyano group; a nitro group; a $C_1$-$C_{20}$ alkyl group; a $C_2$-$C_{20}$ alkenyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ aliphatic group; $C_7$-$C_{20}$ arylalkyl group; and a $C_7$-$C_{20}$ alkylaryl group, and a plurality of adjacent groups thereof may be bonded to each other to form a ring, $R^c$ is selected from the group consisting of a $C_1$-$C_{20}$ alkyl group; a $C_6$-$C_{20}$ aryl group; and a $C_2$-$C_{20}$ heterocyclic group including at least one heteroatom of O, N, S, Si or P;

$R^d$ is selected from the group consisting of hydrogen; deuterium; a $C_1$-$C_{20}$ alkyl group; a $C_6$-$C_{20}$ aryl group; and a $C_2$-$C_{20}$ heterocyclic group including at least one heteroatom of O, N, S, Si or P;

$R^c$ and $R^d$ may be bonded to each other to form a spiro, g is an integer of 0 to 5, h, k, l, o, p and q are independently an integer of 0 to 4, i is an integer of 0 to 7, j is an integer of 0 to 9, m and n are independently an integer of 0 to 3, W is O, S or $NR^{30}$, wherein $R^{30}$ are selected from a group consisting of a $C_1$-$C_{20}$ alkyl group; a $C_2$-$C_{20}$ alkenyl group; $C_6$-$C_{20}$ aryl group; $C_6$-$C_{20}$ aryl group substituted with deuterium; a fluorenyl group; a $C_2$-$C_{20}$ heterocyclic group including at least one heteroatom of O, N, S, Si or P; $C_3$-$C_{20}$ aliphatic group; $C_7$-$C_{20}$ arylalkyl group; $C_8$-$C_{20}$ arylalkenyl group; and a $C_7$-$C_{20}$ alkylaryl group; or, $R^{27}$ and $R^{28}$ may be bonded to each other to form a ring, $R^a$ and $R^b$ are independently selected from the group consisting of a $C_1$-$C_{20}$ alkyl group; a $C_1$-$C_{20}$ alkyl group substituted with deuterium; a $C_2$-$C_{20}$ alkenyl group; a $C_6$-$C_{20}$ aryl group; a $C_6$-$C_{20}$ aryl group substituted with deuterium; a fluorenyl group; a $C_2$-$C_{20}$ heterocyclic group including at least one heteroatom of O, N, S, Si or P; a $C_3$-$C_{20}$ aliphatic group; a $C_7$-$C_{20}$ arylalkyl group; and a $C_7$-$C_{20}$ alkylaryl group, and $R^a$ and $R^b$ may be bonded to each other to form a spiro, $R^{101}$ and $R^{102}$ are the same as the definition of $R^7$, or adjacent groups thereof may be bonded to each other to form a ring, $Ar^2$ is selected from the group consisting of a $C_1$-$C_{20}$ alkyl group substituted or unsubstituted with deuterium; a $C_6$-$C_{20}$ aryl group substituted or unsubstituted with deuterium; and a $C_2$-$C_{20}$ heterocyclic group including at least one heteroatom of O, N, S, Si and P;

ab' is an integer of 0 to 2, ac is an integer of 0 to 4, and ab and ac' are independently an integer of 0 to 3, Ak is a $C_1$-$C_{50}$ alkyl group; or a $C_3$-$C_{30}$ aliphatic ring group;

a, c and d are independently an integer of 0 to 4, b is an integer of 0 to 3,

* indicates a position to be bonded, wherein the aryl group, heterocyclic group, fluorenyl group, aliphatic ring group, fused ring group, alkyl group, alkenyl group and the ring formed by the adjacent groups may be substituted with one or more substituents selected from the group consisting of deuterium; halogen; a cyano group; a nitro group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ aliphatic ring; a $C_7$-$C_{20}$ arylalkyl group; a $C_8$-$C_{20}$ arylalkenyl group; and a $C_7$-$C_{20}$ alkylaryl group, and the hydrogen of these substituents may be further substituted with one or more deuterium.

2. The compound according to claim 1, wherein Ak is represented by any one of Formulas Ak-1 to Ak-8:

Formula Ak-1

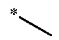

Formula Ak-2

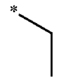

Formula Ak-3

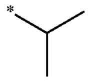

Formula Ak-4

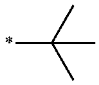

Formula Ak-5

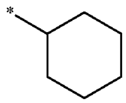

Formula Ak-6

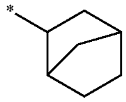

Formula Ak-7

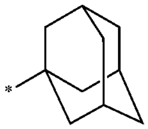

Formula Ak-8

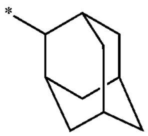

wherein:

* indicates a position to be bonded, and each of Formulas Ak-1 to Ak-8 may be substituted with one or more deuterium.

3. The compound according to claim 1, wherein the compound represented by Formula 1-2 is any one of the following compounds:

P-77

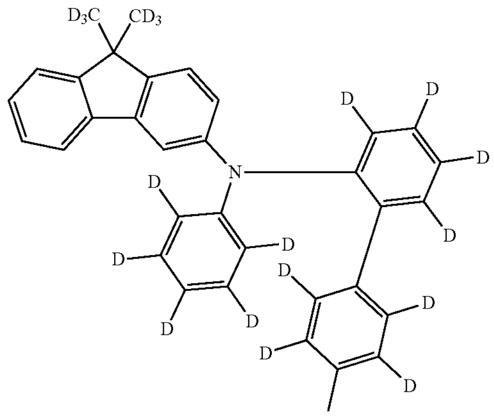

P-78

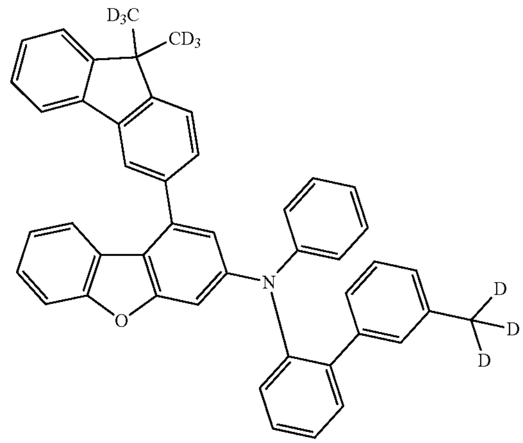

P-79

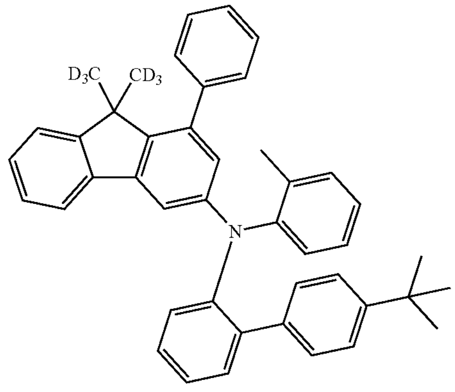

-continued
P-80
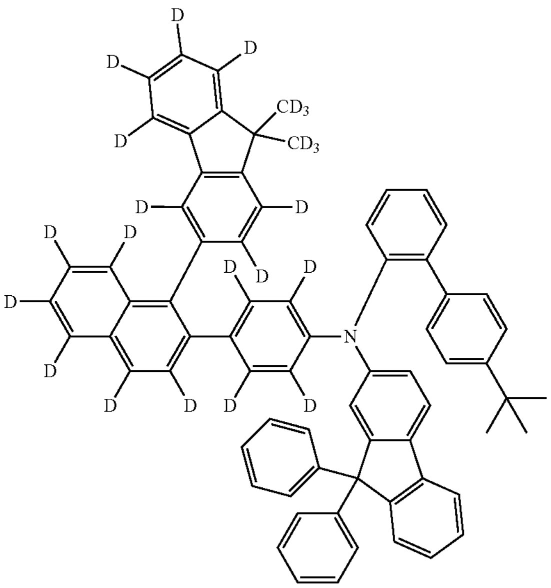
P-81
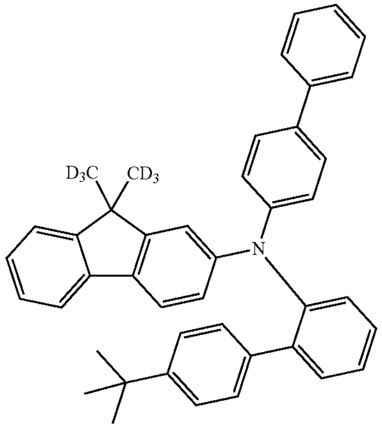
P-82
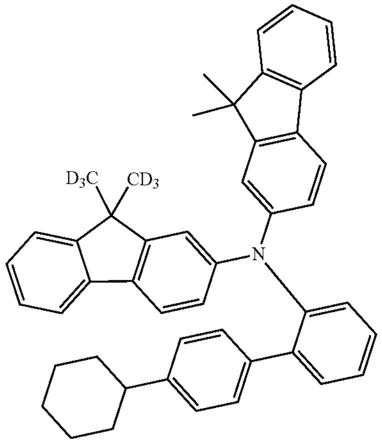
-continued
P-83
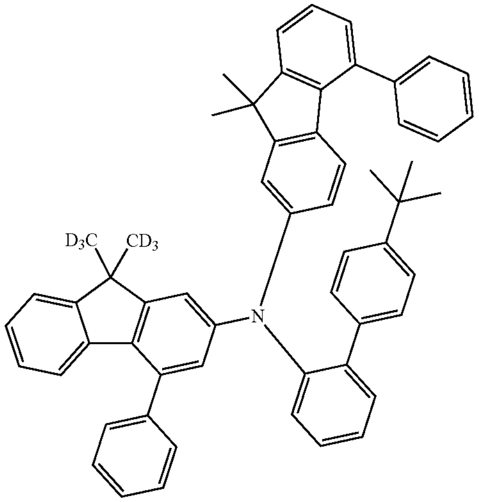
P-84
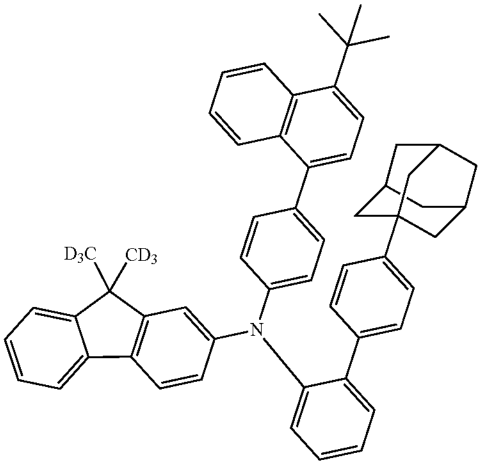
P-85
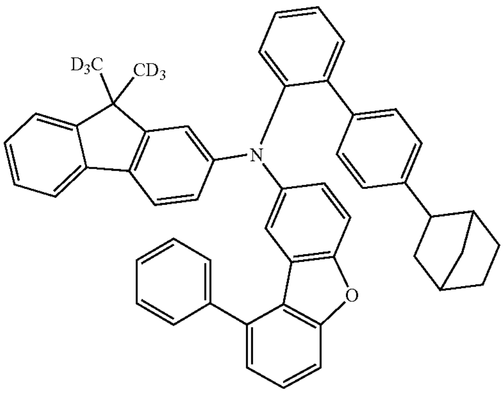

-continued
P-86
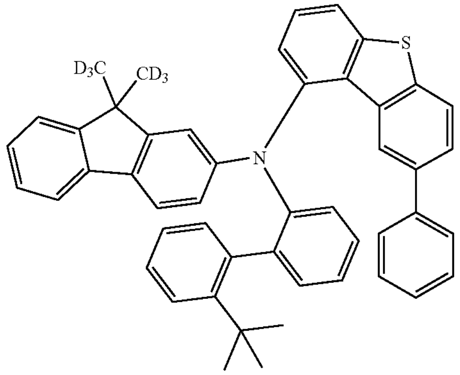
P-87
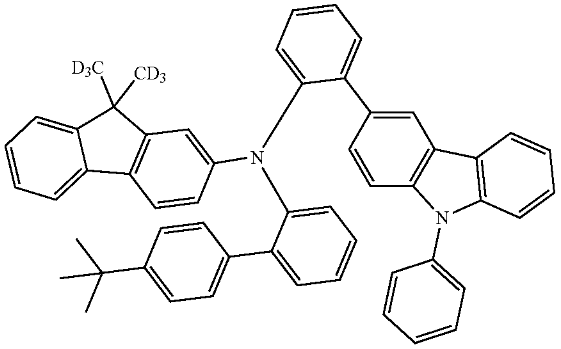
P-88
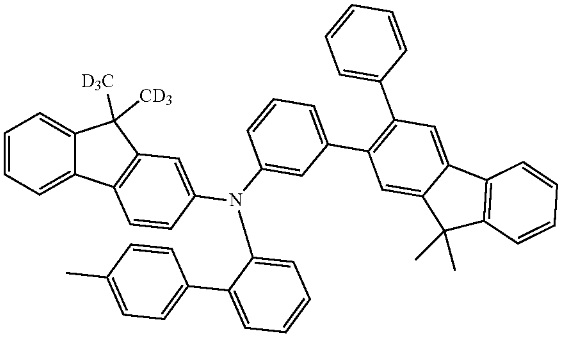
P-89
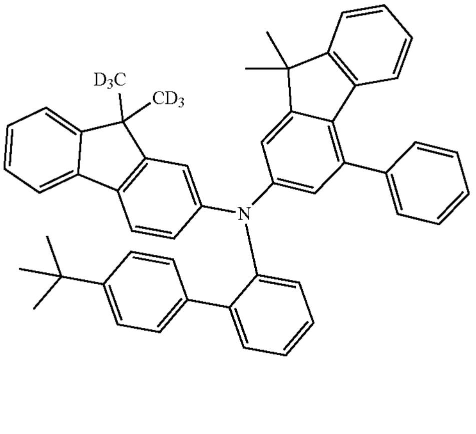
-continued
P-90
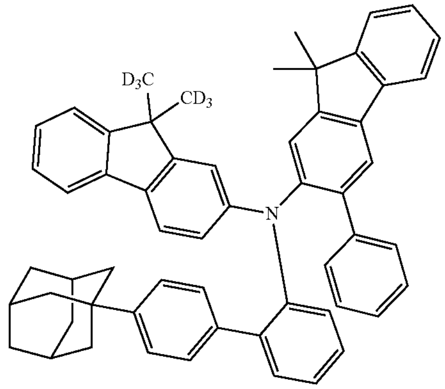
P-91
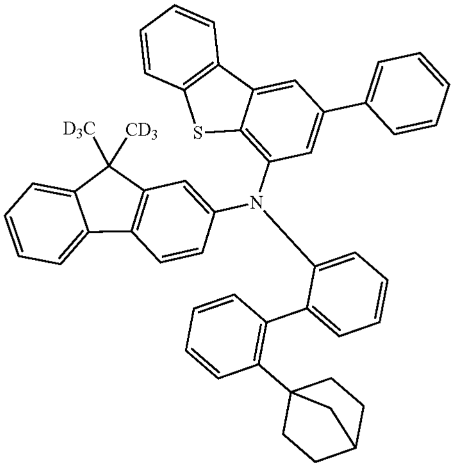
P-92
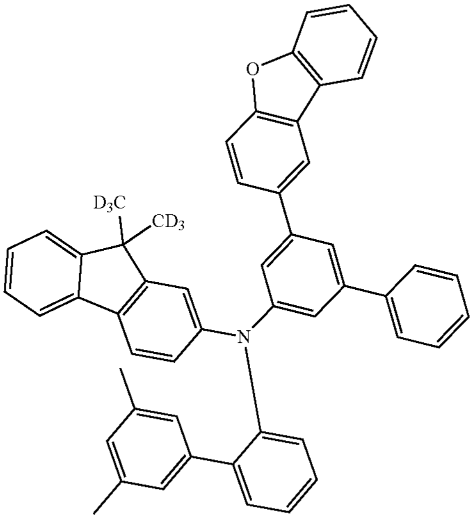

-continued
P-93
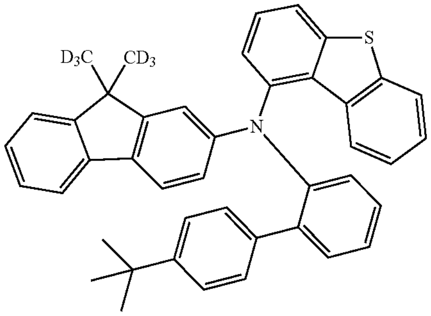
P-94
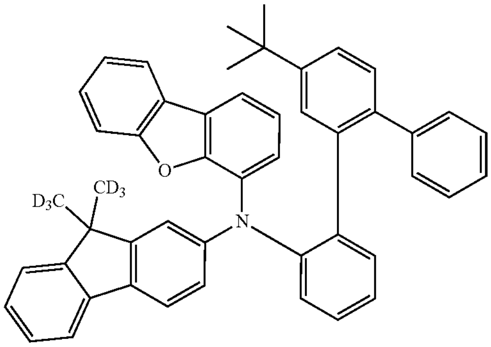
P-95
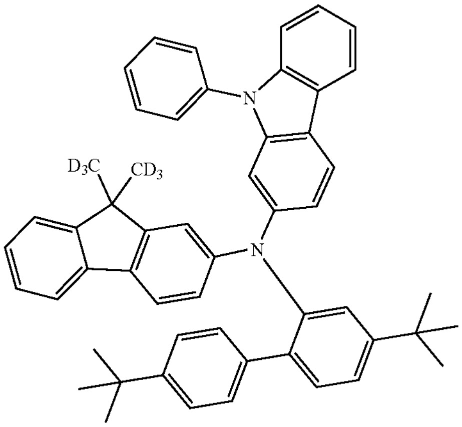
P-96
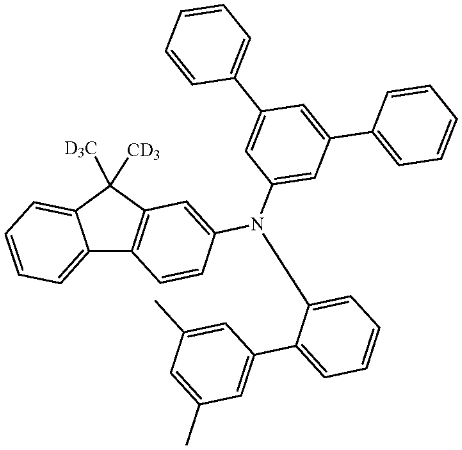
-continued
P-97
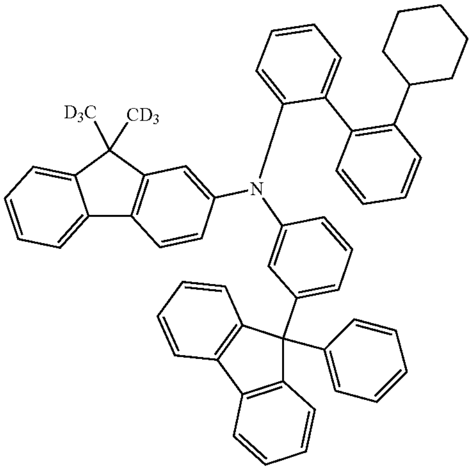
P-98
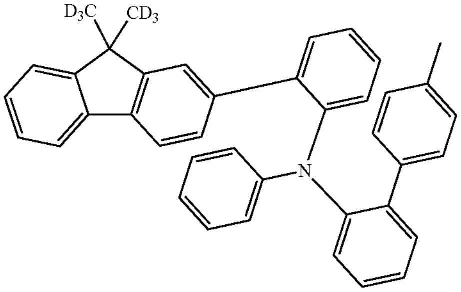
P-99
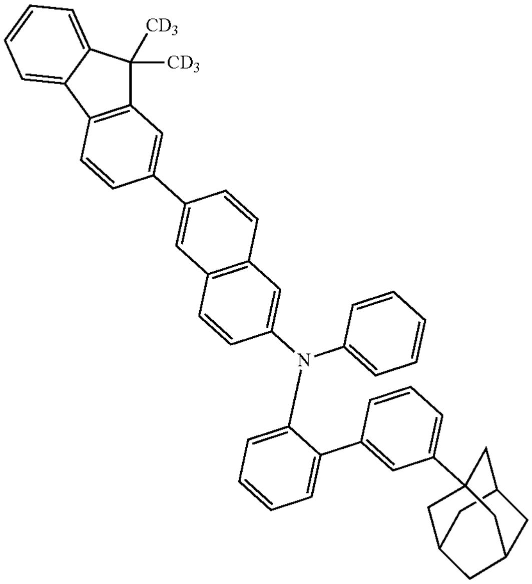

-continued
P-100
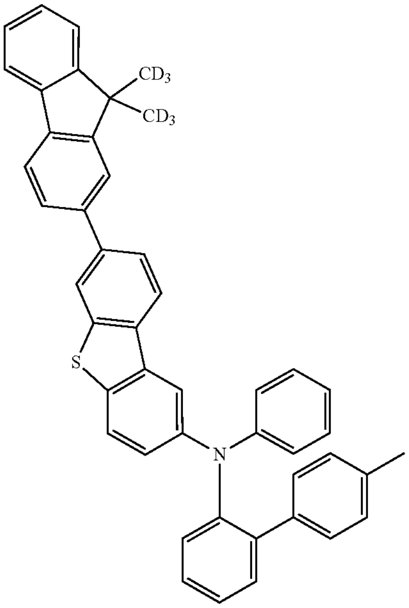
P-101
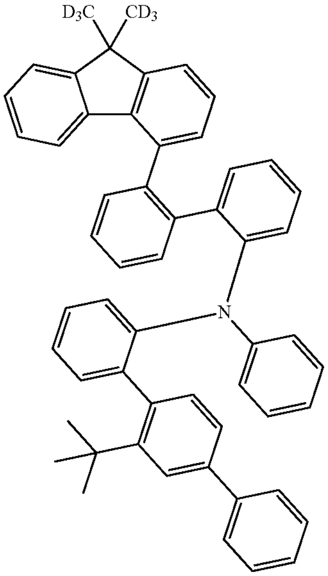
P-102
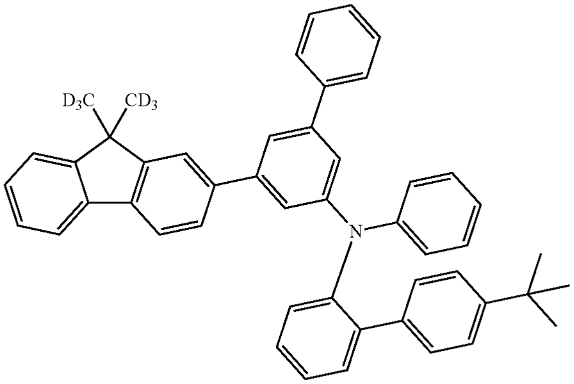
-continued
P-103
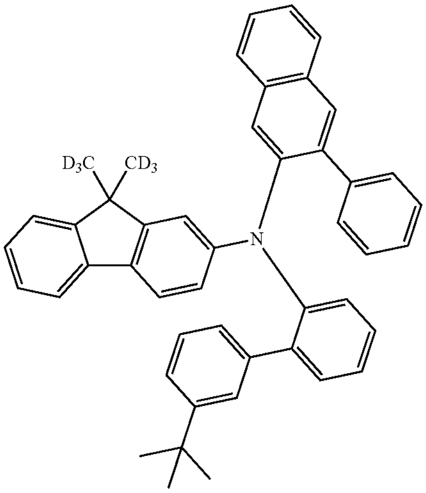
P-104
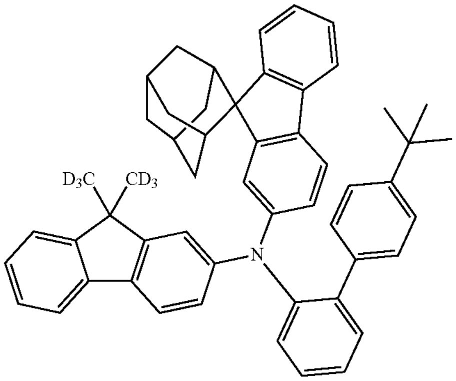
P-105
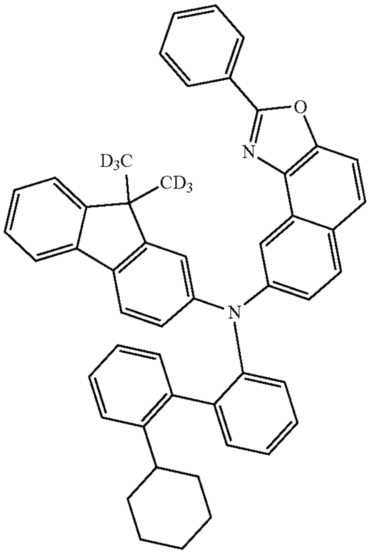

-continued
P-106
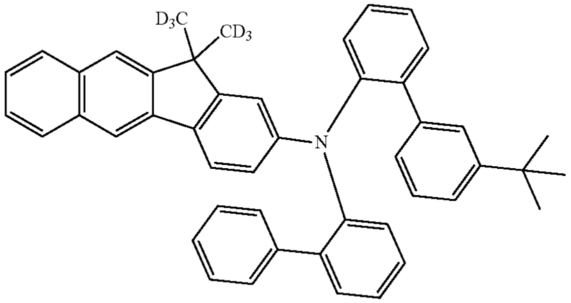
P-107
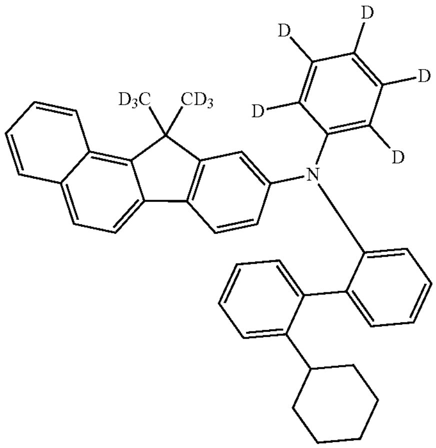
P-108
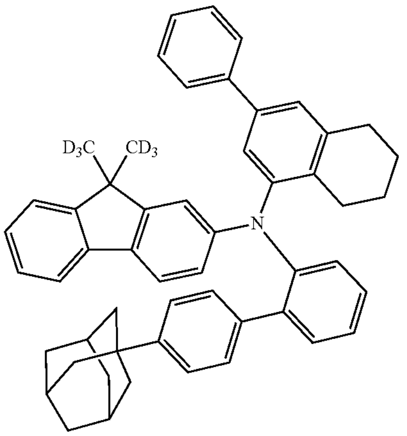
-continued
P-109
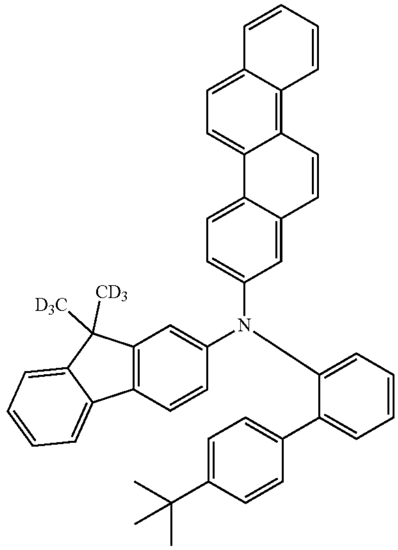
P-110
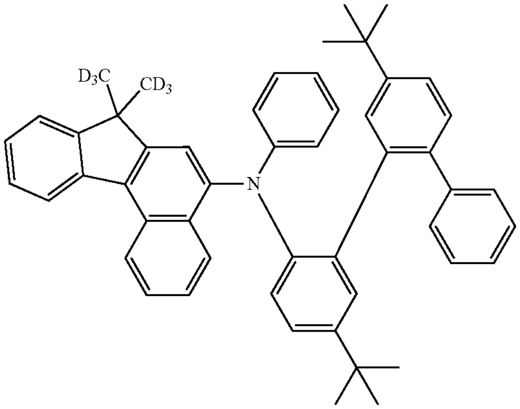
P-111
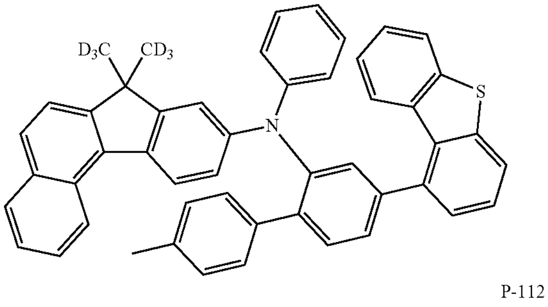
P-112
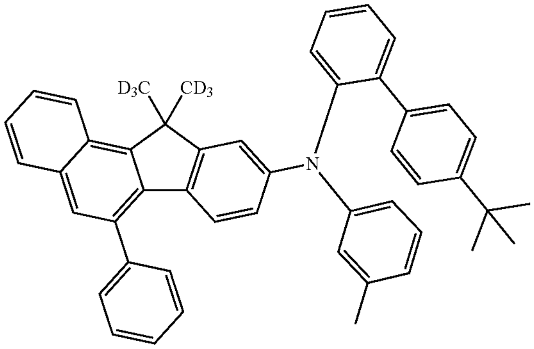

P-113
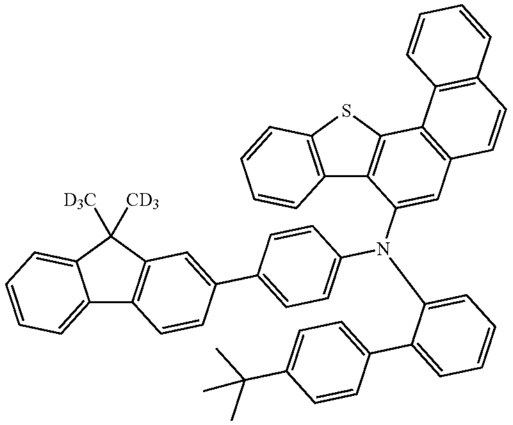
P-114
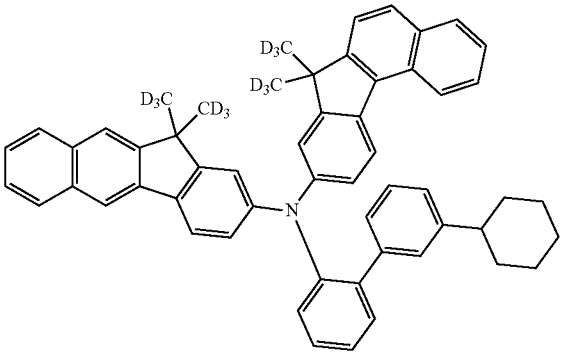
P-115
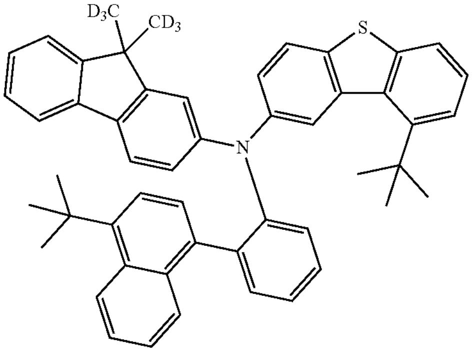
P-116
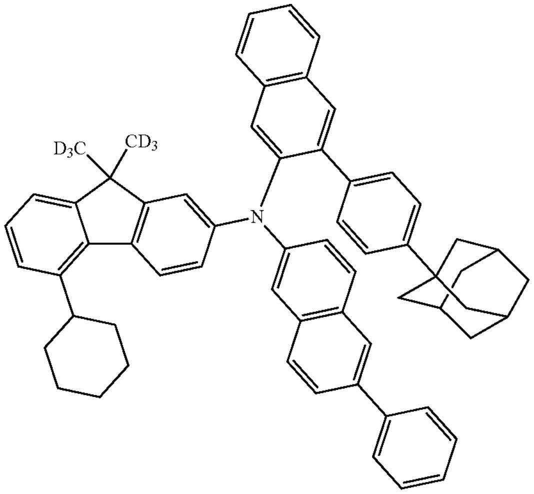
P-117
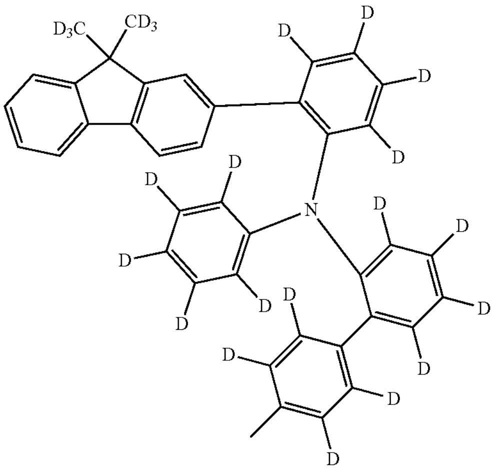
P-118
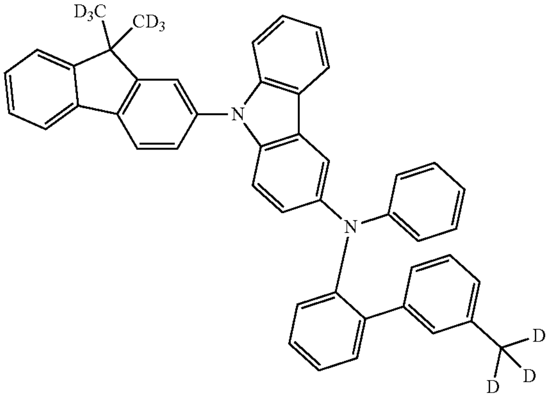

-continued
P-119
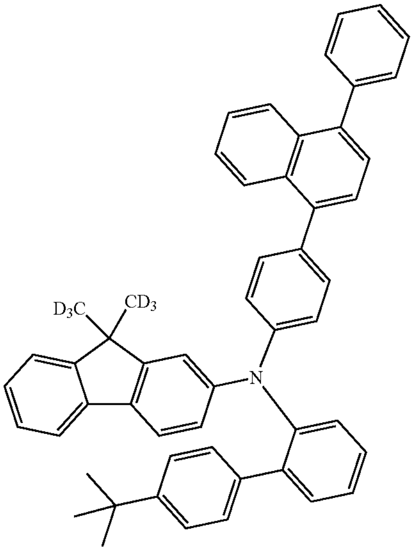
P-120
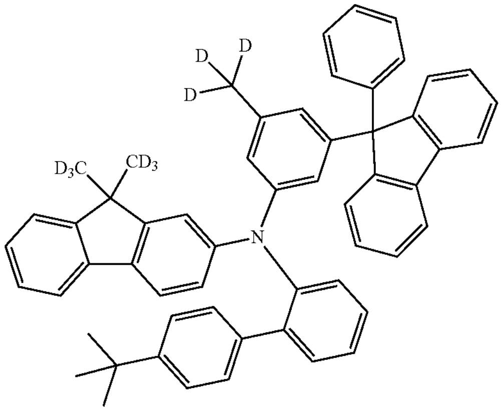
P-141
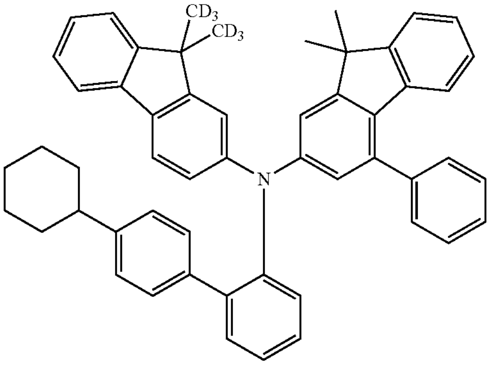
-continued
P-142
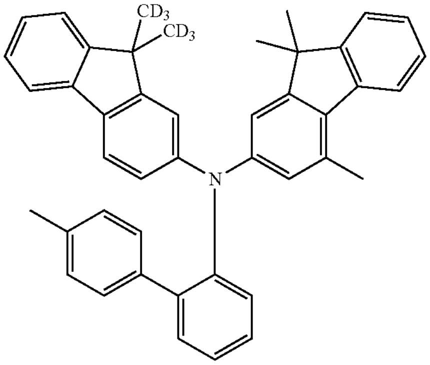
P-143
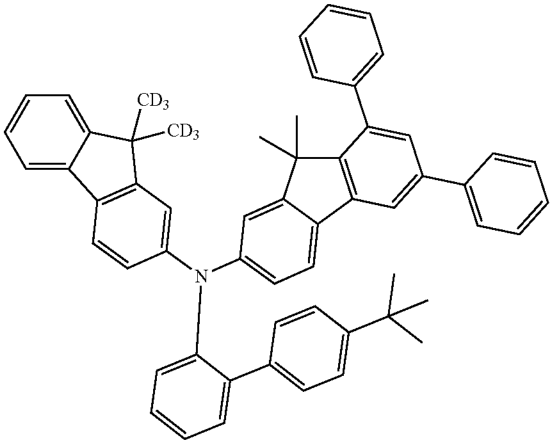
P-144
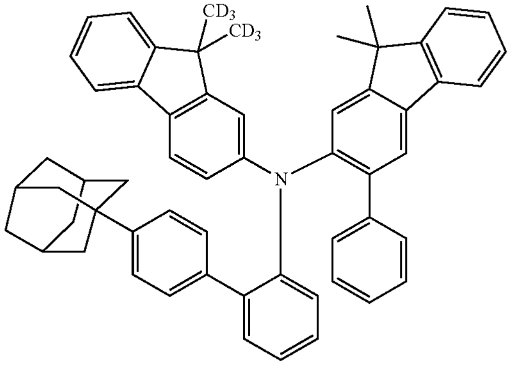

-continued
P-145
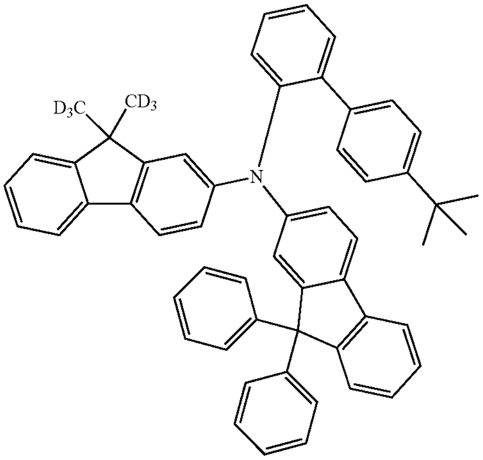
P-146
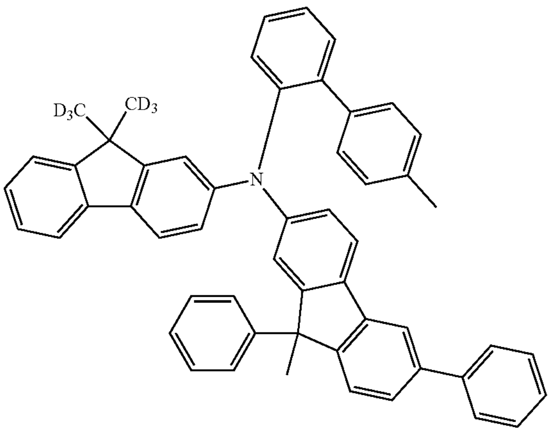
P-147
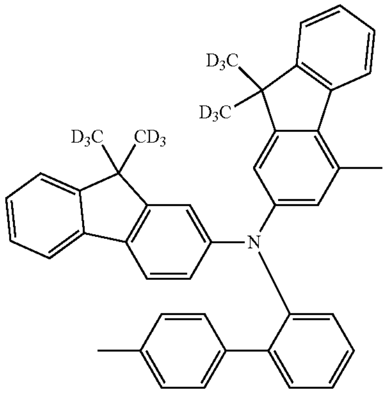
-continued
P-148
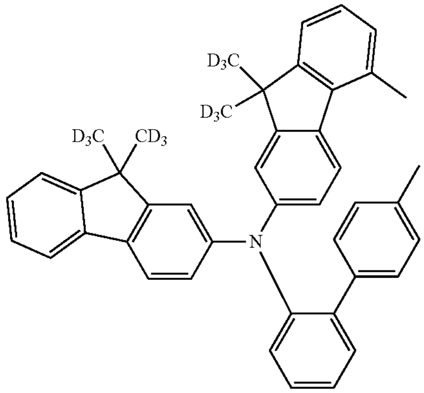
P-149
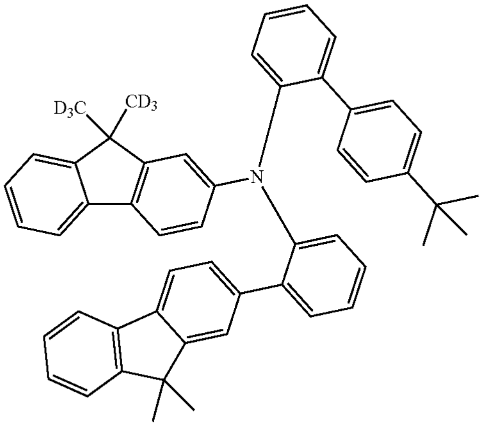
P-150
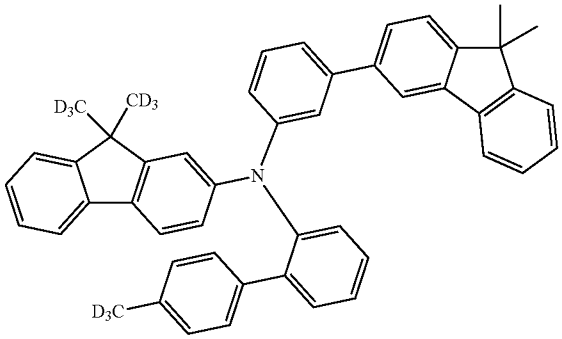
P-151
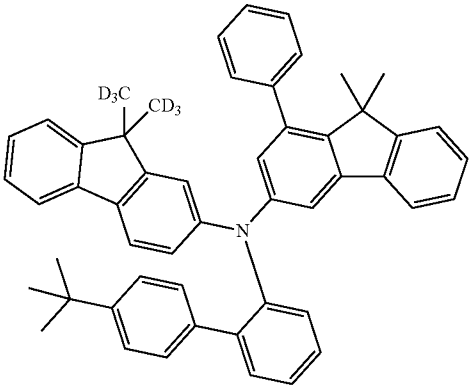

-continued
P-152
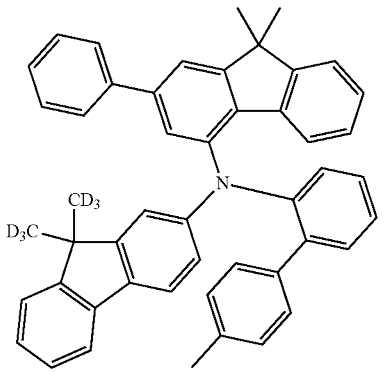
P-153
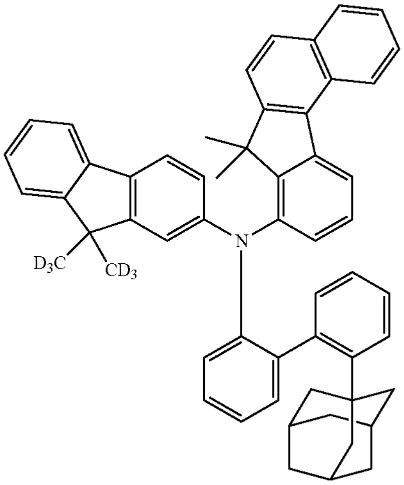
P-154
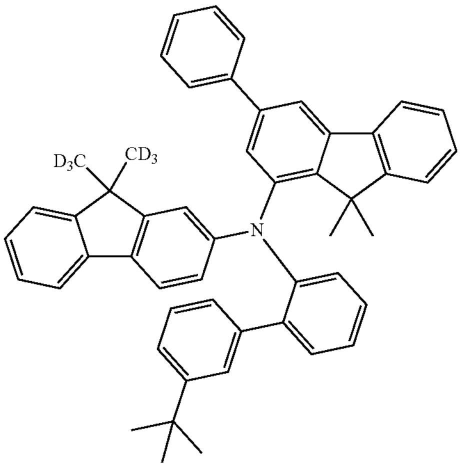
-continued
P-155
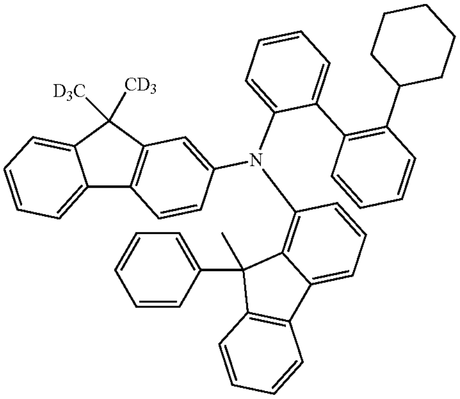
P-156
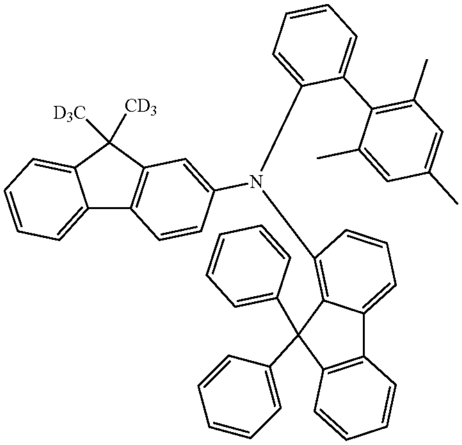
P-157
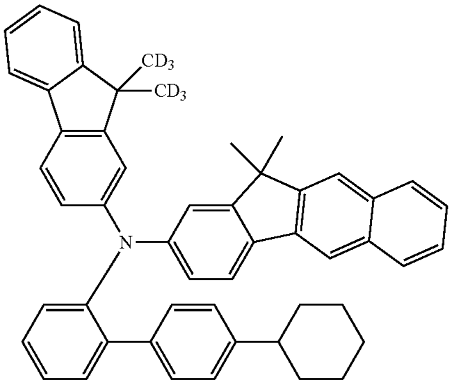

-continued

P-158

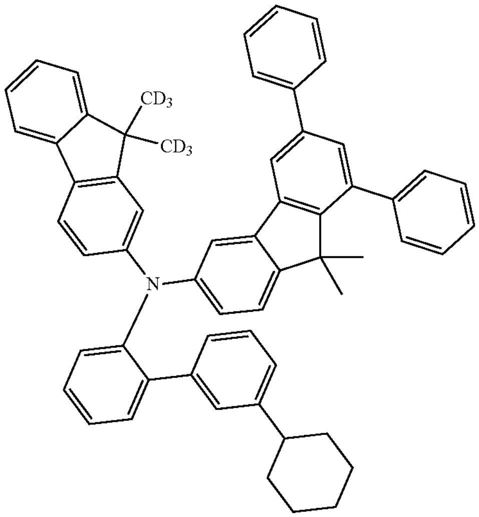

P-159

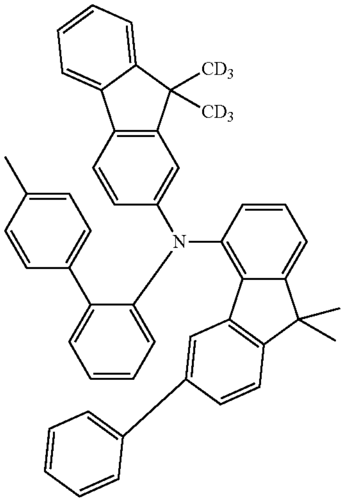

-continued

P-160

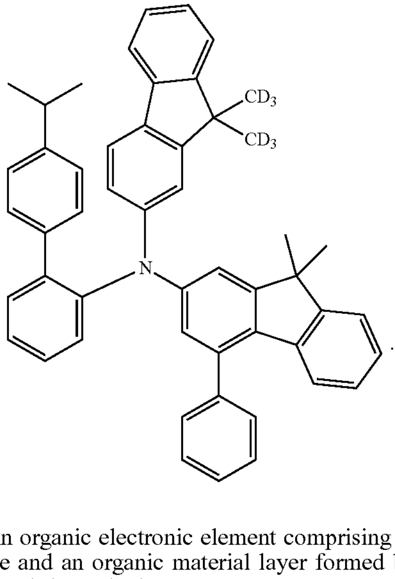

.

4. An organic electronic element comprising an anode, a cathode and an organic material layer formed between the anode and the cathode;

wherein the organic material layer comprises a compound of Formula 1-2 of claim 1.

5. The organic electronic element according to claim 4, wherein the organic material layer comprises at least one of a hole injection layer, a hole transport layer, an emitting auxiliary layer, an emitting layer, an electron transport auxiliary layer, an electron transport layer, and an electron injection layer.

6. The organic electronic element according to claim 4, wherein the organic material layer comprises an emitting auxiliary layer.

7. The organic electronic element according to claim 4, further comprising a light efficiency enhancing layer formed on at least one surface of the anode and the cathode, the surface being opposite to the organic material layer.

8. The organic electronic element according to claim 4, wherein the organic material layer comprises 2 or more stacks, each stack comprising a hole transport layer, an emitting layer, and an electron transport layer, sequentially formed on an anode.

9. The organic electronic element according to claim 4, wherein the organic material layer further comprises a charge generation layer formed between the 2 or more stacks.

10. An electronic device comprising a display device comprising the organic electronic element of claim 4; and a control unit for driving the display device.

11. The electronic device according to claim 10, wherein the organic electronic element is at least one of an OLED, an organic solar cell, an organic photo conductor (OPC), organic transistor (organic TFT) and an element for monochromic or white illumination.

* * * * *